United States Patent
Hunter et al.

(10) Patent No.: US 7,030,218 B2
(45) Date of Patent: Apr. 18, 2006

(54) PSEUDO NATIVE CHEMICAL LIGATION

(75) Inventors: Christie L. Hunter, San Mateo, CA (US); Paolo Botti, Piacenza (IT); James A. Bradburne, Redwood City, CA (US); Shiah-yun Chen, Mountain View, CA (US); Sonya Cressman, Ladysmith (CA); Stephen B. H. Kent, San Francisco, CA (US); Gerd G. Kochendoerfer, Oakland, CA (US); Donald W. Low, Burlingame, CA (US)

(73) Assignee: Gryphon Therapeutics, South San Francisco, CA (US)

( * ) Notice: Subject to any disclaimer, the term of this patent is extended or adjusted under 35 U.S.C. 154(b) by 0 days.

(21) Appl. No.: 10/332,386

(22) PCT Filed: Jul. 12, 2001

(86) PCT No.: PCT/US01/21935

§ 371 (c)(1),
(2), (4) Date: Jan. 8, 2003

(87) PCT Pub. No.: WO02/20034

PCT Pub. Date: Mar. 14, 2002

(65) Prior Publication Data

US 2003/0208046 A1 Nov. 6, 2003

Related U.S. Application Data

(60) Provisional application No. 60/236,377, filed on Sep. 29, 2000, provisional application No. 60/231,339, filed on Sep. 8, 2000.

(51) Int. Cl.
*C07K 1/02* (2006.01)
*C07K 1/07* (2006.01)

(52) U.S. Cl. .................. 530/339; 530/300; 530/345; 530/350; 530/351; 530/399

(58) Field of Classification Search ............... 424/85.1, 424/85.2, 85.4; 514/2, 12, 21; 530/300, 530/339, 345, 350, 351, 399
See application file for complete search history.

(56) References Cited

U.S. PATENT DOCUMENTS

| 3,853,832 | A | * | 12/1974 | Li ................... 530/399 |
| 4,565,785 | A | | 1/1986 | Gilbert et al. ............. 435/317 |
| 4,659,558 | A | | 4/1987 | Urquhart et al. ............ 424/470 |
| 4,673,641 | A | | 6/1987 | George et al. ............... 435/68 |
| 4,710,473 | A | | 12/1987 | Morris ....................... 435/320 |
| 4,738,921 | A | | 4/1988 | Belagaje et al. ............. 435/68 |
| 4,795,706 | A | | 1/1989 | Hsiung et al. ........... 435/172.3 |
| 4,810,499 | A | | 3/1989 | Nuwayser .................. 424/448 |
| 5,079,230 | A | * | 1/1992 | Randawa et al. ............. 514/12 |
| 5,438,040 | A | | 8/1995 | Ekwuribe ...................... 514/3 |
| 5,589,356 | A | | 12/1996 | Tam ........................ 435/68.1 |
| 5,641,511 | A | | 6/1997 | Kuhrts ....................... 424/451 |
| 5,646,285 | A | | 7/1997 | Baindur et al. ............. 546/298 |
| 5,654,000 | A | | 8/1997 | Poli et al. .................. 424/450 |
| 5,681,811 | A | | 10/1997 | Ekwuribe ...................... 514/8 |
| 5,690,954 | A | | 11/1997 | Illum ........................ 424/434 |
| 5,756,672 | A | | 5/1998 | Builder et al. ............. 530/350 |
| 5,759,566 | A | | 6/1998 | Poli et al. .................. 424/434 |
| 5,766,633 | A | | 6/1998 | Milstein et al. ............. 424/489 |
| 5,783,212 | A | | 7/1998 | Fassihi et al. ............. 424/472 |
| 5,792,451 | A | | 8/1998 | Sarubbi et al. ............. 424/85.4 |
| 5,849,331 | A | | 12/1998 | Ducheyne et al. .......... 424/484 |
| 5,854,389 | A | | 12/1998 | Kent et al. .................. 530/334 |
| 5,879,712 | A | | 3/1999 | Bomberger et al. ......... 424/489 |
| 6,002,961 | A | | 12/1999 | Mitragotri et al. ............ 604/20 |
| 6,013,283 | A | | 1/2000 | Greenwald et al. ......... 424/486 |
| 6,017,318 | A | | 1/2000 | Gauthier et al. ............ 600/578 |
| 6,018,678 | A | | 1/2000 | Mitragotri et al. ............ 604/20 |
| 6,027,720 | A | | 2/2000 | Kuga et al. ................ 424/85.1 |
| 6,041,253 | A | | 3/2000 | Kost et al. .................... 604/20 |
| 6,072,041 | A | | 6/2000 | Davis et al. ................ 530/866 |
| 6,410,708 | B1 | * | 6/2002 | Ashkenazi et al. ......... 536/23.5 |
| 6,552,167 | B1 | | 4/2003 | Rose .......................... 530/326 |
| 6,635,257 | B1 | * | 10/2003 | Depla et al. ............. 424/228.1 |

FOREIGN PATENT DOCUMENTS

EP 0 459 630 4/1991

| | | |
|---|---|---|
| WO | WO 91/19735 | 12/1991 |
| WO | WO 95/00846 | 1/1995 |
| WO | WO 96/17935 | 6/1996 |
| WO | WO 96/34878 | 11/1996 |
| WO | WO 97/44054 | 11/1997 |
| WO | WO 98/28434 | 7/1998 |
| WO | WO 99/11655 | 3/1999 |
| WO | WO 99/11666 | 3/1999 |
| WO | WO 02/04015 | 1/2002 |
| WO | WO 02/20034 | 3/2002 |

OTHER PUBLICATIONS

Gloss et al. Examining the Structural and Chemical Flexibility . . . Biochemistry. vol. 34, pp. 12323-12332 (1995).*

Or et al. Cysteine Alkylation in Unprotected Peptides . . . Journal of Organic Chemistry. vol. 56, pp. 3146-3149 (1991).*

Crow et al. Inhibition Of Early Hematopoietic Progenitors . . . Blood. Nov. 15, 1994. vol. 84, No. 10, Supplement 1, p. 127a, Abstract No. 492.*

Ahuja, Satinder, 'Chiral separations and technology: an overview.' Chiral Sep. (1997), 1-7.

Ahuja, Satinder. 'Chiral separations. An overview.' *ACS Symp. Ser.* (1991), 471 Chiral Sep. Liq. Chromatogr.

Yajima, H. et al., "Solution synthesis of a tetratetracontapeptide amide with growth hormone releasing activity," *Chem Pharm Bull (Tokyo)* (1983) May;31(5): 1800-2.

Akira S, et al: "Interleukin-6 in biology and medicine," *Adv Immunol* (1993) 54:1-78.

Atherton E., et al., "Solid Phase Fragment Condensation—The Problems," *Innovation and Perspectives in Solid Phase Synthesis* 11-25, not dated.

Baca, M. et al., "Chemical Ligation of Cysteine-Containing Peptides: Synthesis of a 22 kDa Tethered Demer of HIV-1 Protease," *J. Amer. Chem Soc.* (1995) 117:1881-1887.

Baggiolini M, et al., "Human chemokines: an update," *Am. Rev. Immunol* (1997) 15:675-705.

Botti, P. et al., "Native Chemical Ligation Using Removable N.alpha -(1-phenyl-2-mercaptoethyl) Auxiliaries," *Tetrahedron Letters* 42, 1831-1833 (2001).

Brems et al., "Equilibrium denaturation of pituitary- and recombinant-derived bovine growth hormone" *Biochemistry* 1985 Dec. 17;24(26):7662-8.

Canne et al., "A General Method for the Synthesis of Thioester Resin Linkers for Use in the Solid Phase Synthesis of Peptide-alpha-Thioacids," *Tetrahedron Lett.* (1995) 36: 1217-1220.

Canne L.E. et al., "Solid Phase Protein Synthesis by Chemical Ligation of Unprotected Peptide Segments in Aqueous Solution," *Peptides: Frontiers of Peptide Science, Proceedings of the American Peptide Symposium,* 15th, Nashville, Tennessee, Jun. 14-19, 1997, 301-302 (1999).

Canne L.E. et al., "The Total Chemical Synthesis of L- and D-superoxide Dismutase," *Protein Engineering*, 10-23 (1997).

Chan, T.-H. et al., "Synthesis of Phosphonic Acid Analogues of Sialic Acids (Neu5Ac and KDN) as Potential Sialidase Inhibitors," *J. Org. Chem.* (1997) 62:3500-3504.

Chen GH, et al, "Effect of granulocyte-macrophage colony-stimulating factor on rat alveolar macrophage anticryptococcal activity in vitro," *J Immunol* 1994 Jan. 15;152(2):724-34.

Chong et al., "Single-column purification of free recombinant proteins using a self-cleavable affinity tag derived from a protein splicing element," *Gene* 1997 Jun. 19;192(2):271-281.

Chong et al., "Utilizing the C-terminal cleavage activity of a protein splicing element to purify recombinant proteins in a single chromatographic step," *Nucleic Acids Res.* 1998 Nov. 15;26(22):5109-5115.

Collet, Andre. "Separation Purification of Enantiomers by Crystallization Methods", *Enantiomer* (1999) 4:157-172.

Cotton et al., "Peptide Ligation and Its application to protein engineering," *Chemistry & Biology* (1999) 6(9):247-256.

Dawson et al., "Synthesis of Chemokines by Native Chemical Ligation," *Methods Enzymol.* (1997) 287:34-45.

Dawson et al., "Synthesis of Native Proteins By Chemical Ligation," *Ann. Rev. Biochem* (2000) 69:923-960.

Dawson, P.E. et al. Synthesis of Proteins by Native Chemical Ligation, Science 266, 776-779 (1994).

Dordal, M.S. et al. "The role of carbohydrate in erythropoietin action," (1985) *Endocrinology* 116:2293.

Englebretsen, et al., "A Novel Thioether Linker: Chemical Synthesis of a HIV-1 Protease Analogue by Thioether Ligation," *Tet. Letts.* (1995) 36(48):8871-8874.

Evans et al., "Semisynthesis of cytotoxic proteins using a modified protein splicing element," *Protein Science* (1998) 7:2256-2264.

Gaertner et al., "Site Specific Attachment of Functionalized Poly(ethylene glycol) to the Amino Terminus of Proteins," *Bioconjug. Chem.* (1996) 7(1):38-44.

Gaertner H.F.G., et al., "Chemical Ligation of Proteins and Other Macromolecules, Peptides: Chemistry, Structure and Biology," *Proceedings of the American Peptide Symposium,* 14th, Columbus, Ohio, Jun. 18-23, 1995, 18-20 (1996).

Gaertner, et al., "Site-specific religation of G-CSF fragments through a thioether bond," *Bioconjug Chem.* 1994 Jul.-Aug.; 5(4):333-338.

Gieselman et al., "Synthesis of a selenocysteine-containing peptide by native chemical ligation," *Org Lett.* May 3, 2001;3(9):1331-1334.

Goldwasser, E. et al. "On the mechanism of erythropoietin-induced differentiation. 13. The role of sialic acid in erythropoietin action," *J Biol Chem.* Jul. 10, 1974;249(13): 4202-6.

Goodson et al. "Site-Directed Pegylation Of Recombinant Interleukin-2 At Its Glycosylation Site," *Biotechnology* Apr. 1990, vol. 8, pp. 343-346.

Hackeng et al., "Protein synthesis by native chemical ligation: expanded scope by using straightforward methodology," *Proc Natl Acad Sci U S A.* Aug. 31, 1999; 96(18):10068-73.

Higuchi, M. et al, "Role of Sugar Chains in the Expression of the Biological Activity of Human Erythropoietin," (1992) *J. Biol. Chem.* 267:7703-7709.

Hojo H, et al., "Polypeptide Synthesis Using the S-Alkyl Thioester of a Partially Protected Peptide Segment. Synthesis of the DNA-Binding Domain of c-Myb Protein (142-193)-NH$_2$" (1991) *Bull Chem Soc Jpn* 64:111-117.

Howard M, et al, "Biological Properties of Interleukin 10," *J. Clin. Immunol.* (1992) 12:239-247.

Ingenito et al., "Solid Phase Synthesis of Peptide C-Terminal Thioesters by Fmoc/t-Bu Chemistry," *JACS* (1999) 121(49):11369-11374.

Jacobs, K.J. et al,. "Isolation and characterization of genomic and cDNA clones of human erythropoietin," *Nature* Feb. 28-Mar. 6, 1985;313(6005):806-10.

Jelkmann, W., "Erythropoietin: structure, control of production, and function," *Physiol Rev.* Apr. 1992;72(2):449-89.

Kaiser et al. "Chemical Mutation Of Enzyme Active Sites," *Science* Nov. 2, 1994, vol. 226, No. 4674, pp. 505-511.

Kent S., et al., "Determining the Structure of HIV-1 Protease," *Science* 288, 1590 (2000).

Kent, S.B.H. "Chemical Synthesis of Peptides And Proteins," (1988) *Ann. Rev. Biochem.* 57, 957-984.

Kochendoerfer G.G. et al., "Total Chemical Synthesis of the Integral Membrane Protein Influenza A Virus M2: Role of Its C-Terminal Domain in Tetramer Assembly," *Biochemistry* 38, 11905-11913 (1999).

Kochendoerfer, G.G. et al. "Chemical Protein Synthesis Methods in Drug Discovery," *Current Opinion in Drug Discovery & Development* 4, 205-214 (2001).

Kochendoerfer, G.G. et al. "Total Chemical Synthesis of a 27 kDa TASP Protein Derived from the MscL Ion Channel of M. Tuberulosis by Ketoxime-forming Ligation," *Bioconjugate Chemistry* 13, 474-480 (2002).

Kochendoerfer, G.G. et al., "Chemical Protein Synthesis," *Current Opinion in Chemical Biology* 3, 665-671 (1999).

Komatsu N, et al., "Establishment and characterization of a human leukemic cell line with megakaryocytic features: dependency on granulocyte-macrophage colony-stimulating factor, interleukin 3, or erythropoietin for growth and survival," *Cancer Res.* Jan. 1, 1991; 51(1):341-8.

Kotecha S., "Cytokines in chronic lung disease of prematurity," *Eur J Pediatr.* Aug. 1996;155 Suppl 2:S14-7.

Krantz, S.B., "Erythropoietin," *Blood* Feb. 1, 1991;77(3): 419-34.

Lin, F-K. et al,. "Cloning and expression of the human erythropoietin gene," *Proc Natl Acad Sci U S A* Nov. 1985;82(22):7580-4.

Liu, C.F. et al., "Chemical Ligation Approach To Form a Peptide Bond between Unprotected Peptide Segments. Concept and Model Study," *J. Amer. Chem Soc.* (1994) 116: 4149-4153.

Liu, C.F. et al., "Orthogonal Ligation of Unprotected Peptide Segments through Pseudoproline Formation for the Synthesis of HIV-1 Protease Analogs," *J. Amer. Chem Soc.* (1996) 118:307-312.

Lopata et al., "Quantitative Approaches to Optical Resolution," *J. Chem. Res. Minipprint* (1984) 10:2930-2962.

Low D.W. et al., "Rational Fine-Tuning of the Redox Potentials in Chemically Synthesized Rubredoxins," *Journal of the American Chemical Society* 120, 11536-11537 (1998).

Low, D.W. et al., "Backbone-engineered High-potential Iron Proteins: Effects of Active-Site Hydrogen Bonding on Reduction Potential," *Journal of the American Chemical Society* 122, 11039-11040 (2000).

Low, D.W. et al., "Total Synthesis of Cytochrome b562 by Native Chemical Ligation Using a Removable Auxiliary," *Proceedings of the National Academy of Sciences of the United States of America* 98, 6554-6559 (2001).

Lowy, P.H. et al., "Inactivation of Erythropoietin by Neuraminidase and by Mild Substitution Reactions," (1960) *Nature* 185:102.

Lu W. et al. "Total Chemical Synthesis of Bovine Pancreatic Trypsin Inhibitor by Native Chemical Ligation," *FEBS Letters* 429, 31-35 (1998).

Lu W. et al., "Probing Intermolecular Backbone H-bonding in Serine Proteinase-Protein Inhibitor Complexes," *Chemistry & Biology* 6, 419-427 (1999).

Lu, W-Y, et al., "Deciphering the Role of the Electrostatic Interactions Involving Gly70 in eglin C by Total Chemical Protein Synthesis," *Biochemistry* 39, 3575-3584 (2000).

Lundblad RL., "Chemical Reagents for Protein Modification," *CRC Press* (1991,)(Table of Contents).

Mandujano J, et al., "Granulocyte-macrophage colony stimulating factor and *Pneumocystis carinii* pneumonia in mice," *Am J Respir Crit Care Med.* Apr. 1995;151(4):1233-8.

Marston et al., "Solubilization of protein aggregates," *Methods Enzymol.* 1990;182:264-76.

Milton, R.C..D. et al. Total Chemical Synthesis of a D-Enzyme: The Enantiomers of HIV-1 Protease Show Reciprocal Chiral Substrate Specificity, *Science* 256, 1445-1448 (1992).

Mitraki and King, "Protein Folding Intermediates and Inclusion Body Formation," *Bio/Technology,* 7: 690 (1989).

Miura Y, et al., "Regulation of Both Erythroid and Megakaryocytic Differentiation of a Human Leukemia Cell Line, UT-7," *Acta Haematol* (1998) 99:180-184.

Muramatsu H. et al., "Localization of heparin-binding, neurite outgrowth and antigenic regions in midkine molecule," *Biochem Biophys Res Commun.* Sep. 15, 1994;203(2)1131-9.

Porter, D.L. et al., "Regulation of Erythropoietin production," (1993) *Exp. Hematol.* 21:399.

Robson B., et al. "Doppelganger Proteins as Drug Leads," *Nature Biotechnology* 14, 892-893 (1996).

Rose et al., "Stepwise Solid-Phase Synthesis of Polyamides As Linkers," *J. Am. Chem. Soc.* Aug. 4, 1999, 121:7034-7038.

Rose, et al., "Facile Synthesis of Homogeneous Artificial Proteins," *J. Amer. Chem. Soc.* (1994) 116:30-33.

Rose, K. et al., "Natural Peptides as Building Blocks for the Synthesis of Large Protein-like Molecules with Hydrazone and Oxime Linkages," *Bioconjugate Chem.* (1996) 7:552-556.

Sasaki, H. et al., "Carbohydrate structure of erythropoietin expressed in Chinese hamster ovary cells by a human erythropoietin cDNA" *J Biol Chem.* Sep. 5, 1987;262(25): 12059-76.

Sawyer, S.T. et al., "Erythropoietin cell biology," *Hematol Oncol Clin North Am.* Oct. 1994;8(5):895-911.

Saxon, E. et al., "A "traceless" Staudinger ligation for the chemoselective synthesis of amide bonds," *Org Lett.* Jul. 13, 2000;2(14):2141-3.

Schnölzer, M. et al,. "Constructing proteins by dovetailing unprotected synthetic peptides: backbone-engineered HIV protease," *Science.* Apr. 10, 1992;256(5054):221-5.

Schnölzer, M., "In situ neutralization in Boc-chemistry solid phase peptide synthesis. Rapid, high yield assembly of difficult sequences," *Int J Pept Protein Res.* Sep.-Oct. 1992; 40(3-4):180-193.

Shao Y. et al., "A Novel Method to Synthesize Cyclic Peptides," *Tetrahedron Letters* 39, 3911-3914 (1998).

Shao Y. et al., "Protein Splicing: Occurrence, Mechanisms, and Related Phenomena," *Chemistry & Biology* 4, 187-194 (1997).

Shin et al., "Fmoc-Based Synthesis of Peptide-Thioesters: Application to the Total Chemical Synthesis of a Glycoprotein by Native Chemical Ligation," (1999) *J. Am. Chem. Soc.,* 121, 11684-11689.

Siani M.A. et al., "Rapid Modular Total Chemical Synthesis of Proteins Based on Genome Sequence Data," *Peptides: Frontiers of Peptide Science, Proceedings of the American Peptide Symposium*, 15th, Nashville, Tennessee, Jun. 14-19, 1997, 643-644 (1999).

Simon R. et al., "Peptoids: A Modular Approach to Drug Discovery," *Proc. Natl. Acad. Sci. U.S.A.* (1992) 89: 9367-71.

Spivak et al., "The in vivo metabolism of recombinant human erythropoietin in the rat," *Blood.* Jan. 1989;73(1):90-9.

Standiford TJ, et al., "Cytokines in host defense against pneumonia," *J Investig Med.* Aug. 1997;45(6):335-45.

Sunder et al., "Chiral Hyperbranched Dendron Analogues," *Macromolecules* (2000) 33:253.

Takeuchi, M. et al., "Relationship between Sugar Chain Structure and Biological Activity of Recombinant Human Erythropoietin in Chinese Hamster Ovary Cells," (1989) *Proc. Natl. Acad. Sci. USA* 86:7819.

Tam et al. "Methionine Ligation Strategy in the Biomimetic Synthesis of Parathyroid Hormones," *Biopolymers,* 1998, vol. 46, pp. 319-327.

Wilken J. et al., "Chemical Protein Synthesis," *Current Opinion in Biotechnology* 9, 412-426 (1998).

Wilken J. et al., "Rational Development of an Anti-HIV Protein Active at Low Picomolar Concentrations," *Peptides for the New Millennium, Proceedings of the American Peptide Symposium,* 16th, Minneapolis, Minnesota, Jun. 26-Jul. 1, 1999, 513-515 (2000).

Wilken J. et al., "Total Chemical Synthesis and High-Resolution Crystal Structure of the Potent Anti-HIV Protein AOP-RANTES," *Chemistry & Biology* 6, 43-51 (1999).

Wojchowski, D.M. et al. "Active human erythropoietin expressed in insect cells using a baculovirus vector: a role for N-linked oligosaccharide," *Biochim Biophys Acta.* Dec. 8, 1987;910(3):224-32.

Xing Z, et al., "IL-6 is an antiinflammatory cytokine required for controlling local or systemic acute inflammatory responses," *J Clin Invest.* Jan. 15, 1998;101(2):311-20.

Yan, L.Z. et al. "Synthesis of peptides and proteins without cysteine residues by native chemical ligation combined with desulfurization," *J Am Chem Soc.* Jan. 31, 2001;123(4):526-33.

Zhang, et al., "Preparation of functionally active cell-permeable peptides by single-step ligation of two peptide modules," *Proc Natl Acad Sci U S A.* Aug. 4, 1998;95(16):9184-9.

\* cited by examiner

*Primary Examiner*—Jeffrey Edwin Russel
(74) *Attorney, Agent, or Firm*—Jeffrey I. Auerbach; Berenato, White & Stavish, LLC

(57) ABSTRACT

The present invention concerns methods and compositions for extending the technique of native chemical ligation of a wider range of peptides, polypeptides, other polymers and other molecules via an amide bond (see FIG. 1). The invention further provides methods and uses for such proteins and derivatized proteins. The invention is particularly suitable for use in the synthesis of optionally polymer-modified, synthetic bioactive proteins, and of pharmaceutical compositions that contain such proteins.

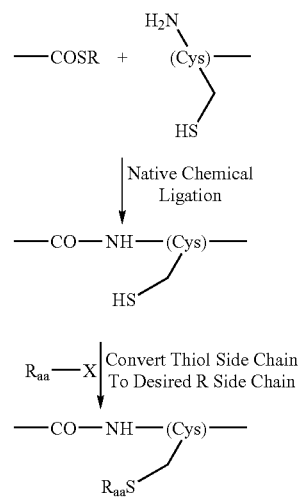

5 Claims, 7 Drawing Sheets

Figure 6

| NNY | RANTES Residues 2-68 | Linker | FA |

| P2 | Y3 | E66X -pPEG | M68X -pPEG |

| One or more N-loop residues 12-20 to X | S67X -pPEG |

Preparation of branched pPEG assemblies

PSEUDO NATIVE CHEMICAL LIGATION

CROSS-REFERENCE TO RELATED APPLICATIONS

This application claims priority to U.S. Patent Applications Ser. Nos. 60/231,339 (filed Sep. 8, 2000) and 60/236,377 (filed Sep. 29, 2000), both of which applications are herein incorporated by reference in their entirety.

FIELD OF THE INVENTION

The present invention relates to methods and compositions for extending the technique of native chemical ligation to permit the ligation of a wider range of peptides, polypeptides, other polymers and other molecules via an amide bond. The invention further provides methods and uses for such proteins and derivatized proteins.

BACKGROUND OF THE INVENTION

Over the past 30 years, medical attention has increasingly turned to the possibility of using naturally produced proteins as therapeutic drugs for the treatment of disease.

Recombinant DNA techniques have become the primary method for commercial production of many polypeptides and proteins because of the large quantities that can be produced in bacteria and other host cells. Recombinant protein production involves transfecting or transforming host cells with DNA encoding the desired exogenous protein and growing the cells under conditions favoring expression of the recombinant protein. *E. coli* and yeast are favored as hosts because they can be made to produce recombinant proteins at high titers (see, U.S. Pat. No. 5,756,672 (Builder et al.).

Numerous U.S. patents have been issued with respect to general bacterial expression of recombinant-DNA-encoded proteins (see, for example, U.S. Pat. Nos. 4,565,785; 4,673, 641; 4,738,921; 4,795,706; 4,710,473). Unfortunately, the use of recombinant DNA techniques has not been universally successful. Under some conditions, certain heterologous proteins expressed in large quantities from bacterial hosts are precipitated within the cells in dense aggregates, recognized as bright spots visible within the enclosure of the cells under a phase-contrast microscope. These aggregates of precipitated proteins are referred to as "refractile bodies," and can constitute a significant portion of the total cell protein (Brems et al., Biochemistry (1985) 24: 7662.

Recovery of protein from these bodies has presented numerous problems, such as how to separate the protein encased within the cell from the cellular material and proteins harboring it, and how to recover the inclusion body protein in biologically active form. For general review articles on retractile bodies, see Marston, supra; Mitraki and King, Bio/Technology, 7: 690 (1989); Marston and Hartley, Methods in Enzymol., 182: 264–276 (1990); Wetzel, "Protein Aggregation In Vivo: Bacterial Inclusion Bodies and Mammalian Amyloid," in Stability of Protein Pharmaceuticals: In Vivo Pathways of Degradation and Strategies for Protein Stabilization, Ahern and Manning (eds.) (Plenum Press, 1991); and Wetzel, "Enhanced Folding and Stabilization of Proteins by Suppression of Aggregation In Vitro and In Vivo," in Protein Engineering—A Practical Approach, Rees, A. R. et al. (eds.) (IRL Press at Oxford University Press, Oxford, 1991). A need therefore exists for an alternative way of producing bioactive proteins.

One alternative to recombinant production of proteins involves the use of the principles of organic chemistry to synthesize proteins. Existing methods for the chemical synthesis of proteins include stepwise solid phase synthesis, and fragment condensation either in solution or on solid phase. The classic stepwise solid phase synthesis of Merrifield involves covalently linking an amino acid corresponding to the carboxy-terminal amino acid of the desired peptide chain to a solid support and extending the polypeptide chain toward the amino end by stepwise coupling of activated amino acid derivatives having activated carboxyl groups. After completion of the assembly of the fully protected solid phase bound peptide chain, the peptide-solid phase covalent attachment is cleaved by suitable chemistry and the protecting groups removed to give the product polypeptide.

There are unfortunately multiple disadvantages to the stepwise solid phase synthesis method, including the formation of solid-phase bound by products that result from incomplete reaction at the coupling and deprotection steps in each cycle. The longer the peptide chain, the more challenging it is to obtain high-purity well-defined products. The synthesis of proteins and large polypeptides by this route is a time-consuming and laborious task.

The solid phase fragment condensation approach (also known as segment condensation) was designed to overcome the difficulties in obtaining long polypeptides via the solid phase stepwise synthesis method. The segment condensation method involves preparation of several peptide segments by the solid phase stepwise method, followed by cleavage from the solid phase and purification of these maximally protected segments. The protected segments are condensed one-by-one to the first segment, which is bound to the solid phase. Often, however, technical difficulties are encountered in many of the steps of solid phase segment condensation. See E. Atherton, et al., "Solid Phase Fragment Condensation— The Problems," in Innovation and Perspectives in Solid Phase Synthesis 11–25 (R. Epton, et al. 1990). For example, the use of protecting groups on segments to block undesired ligating reactions can frequently render the protected segments sparingly soluble, interfering in efficient activation of the carboxyl group. Limited solubility of protected segments also can interfere with purification of protected segments. See K. Akaji et al., Chem. Pharm. Bull.(Tokyo) 33:184–102 (1985). Protected segments are difficult to characterize with respect to purity, covalent structure, and are not amenable to high resolution analytical ESMS (electrospray mass spectrometry) (based on charge). Racemization of the C-terminal residue of each activated peptide segment is also a problem, except if ligating is performed at Glycine residues. Moreover, cleavage of the fully assembled, solid-phase bound polypeptide from the solid phase and removal of the protecting groups frequently can require harsh chemical procedures and long reaction times that result in degradation of the fully assembled polypeptide.

Segment condensation can be done in solution rather than on solid phase. See H. Muramatsu et al., Biochem. and Biophys. Res. Commn. 203(2):1131–1139 (1994). However, segment condensation in solution requires purification of segments prior to ligation as well as use of protecting groups on a range of different side chain functional groups to prevent multiple undesired side reactions. Moreover, the ligation in solution does not permit easy purification and wash steps afforded by solid phase ligations. Furthermore, the limitations with respect to solubility of protected peptide segments and protected peptide intermediate reaction products are exacerbated.

Chemical ligation of peptide segments has been explored in order to overcome the solubility problems frequently encountered with maximally protected peptide. Chemical ligation involves the formation of a selective covalent linkage between a first chemical component and a second chemical component. Unique, mutually reactive, functional groups present on the first and second components can be used to render the ligation reaction chemoselective. For example, the chemical ligation of peptides and polypeptides involves the chemoselective reaction of peptide or polypeptide segments bearing compatible Unique, mutually-reactive, C-terminal and N-terminal amino acid residues. Several different chemistries have been utilized for this purpose, examples of which include native chemical ligation (Dawson, et al., *Science* (1994) 266:776–779; Kent, et al., WO 96/34878; Kent, et al., WO 98/28434), oxime forming chemical ligation (Rose, et al., *J. Amer. Chem. Soc.* (1994) 116:30–34), thioester forming ligation (Schnölzer, et al., Science (1992) 256:221–225), thioether forming ligation (Englebretsen, et al., *Tet. Letts.* (1995) 36(48):8871–8874), hydrazone forming ligation (Gaertner, et al., *Bioconj. Chem.* (1994) 5(4):333–338), and thiazolidine forming ligation and oxazolidine forming ligation (Zhang, et al., *Proc. Natl. Acad. Sci.* (1998) 95(16):9184–9189; Tam et al., WO 95/00846; U.S. Pat. No. 5,589,356) or by other methods (Yan, L. Z. and Dawson, P. E., "Synthesis of Peptides and Proteins without Cysteine Residues by Native Chemical Ligation Combined with Desulfurization," *J. Am. Chem. Soc.* 2001; 123, 526–533, herein incorporated by reference; Gieselnan et al., Org. Lett. 2001 3(9):1331–1334; Saxon, E. et al., "Traceless" Staudinger Ligation for the Chemoselective Synthesis of Amide Bonds. Org. Lett. 2000, 2, 2141–2143).

Of these methods, only the native chemical ligation approach yields a ligation product having a native amide (i.e. peptide) bond at the ligation site. The original native chemical ligation methodology (Dawson et al., supra; and WO 96/34878) has proven a robust methodology for generating a native amide bond at the ligation site. Native chemical ligation involves a chemoselective reaction between a first peptide or polypeptide segment having a C-terminal α-carboxythioester moiety and a second peptide or polypeptide having an N-terminal cysteine residue. A thiol exchange reaction yields an initial thioester-linked intermediate, which spontaneously rearranges to give a native amide bond at the ligation site while regenerating the cysteine side chain thiol. The primary drawback of the original native chemical ligation approach is that it requires an N-terminal cysteine, i.e., it only permits the joining of peptides and polypeptide segments possessing an N-terminal cysteine.

Notwithstanding this drawback, native chemical ligation of peptides with N-terminal amino acids other than cysteine has been reported (WO98/28434). In this approach, the ligation is performed using a first peptide or polypeptide segment having a C-terminal α-carboxythioester and a second peptide or polypeptide segment having an N-terminal N-{thiol-substituted auxiliary} group represented by the formula HS—$CH_2$—$CH_2$—O—NH-[peptide]. Following ligation, the N-{thiol substituted auxiliary} group is removed by cleaving the HS—$CH_2$—$CH_2$—O-auxiliary group to generate a native amide bond at the ligation site. One limitation of this method is that the use of a mercaptoethoxy auxiliary group can successfully lead to amide bond formation only at a glycine residue. This produces a ligation product that upon cleavage generates a glycine residue at the position of the N-substituted amino acid of the second peptide or polypeptide segment. As such, this embodiment of the method is only suitable if one desires the ligation product of the reaction to contain a glycine residue at this position, and in any event can be problematic with respect to ligation yields, stability of precursors, and the ability to remove the O-linked auxiliary group. Although other auxiliary groups may be used, for example the $HSCH_2CH_2NH$-[peptide], without limiting the reaction to ligation at a glycine residue, such auxiliary groups cannot be removed from the ligated product.

Accordingly, what is needed is a broadly applicable and robust chemical ligation system that extends native chemical ligation to a wide variety of different amino acid residues, peptides, polypeptides, polymers and other molecules by means of an effective, readily removable thiol-containing auxiliary group, and that joins such molecules together with a native amide bond at the ligation site. The present invention addresses these and other needs.

BRIEF DESCRIPTION OF THE FIGURES

FIG. 6 shows the structure of preferred synthetic RANTES analogs. In the Figure, NNY=nonanoyl, X=non-naturally encoded amino acid having a hydrophobic side chain, pPEG and FA=fatty acid

SUMMARY OF THE INVENTION

Figure 1:
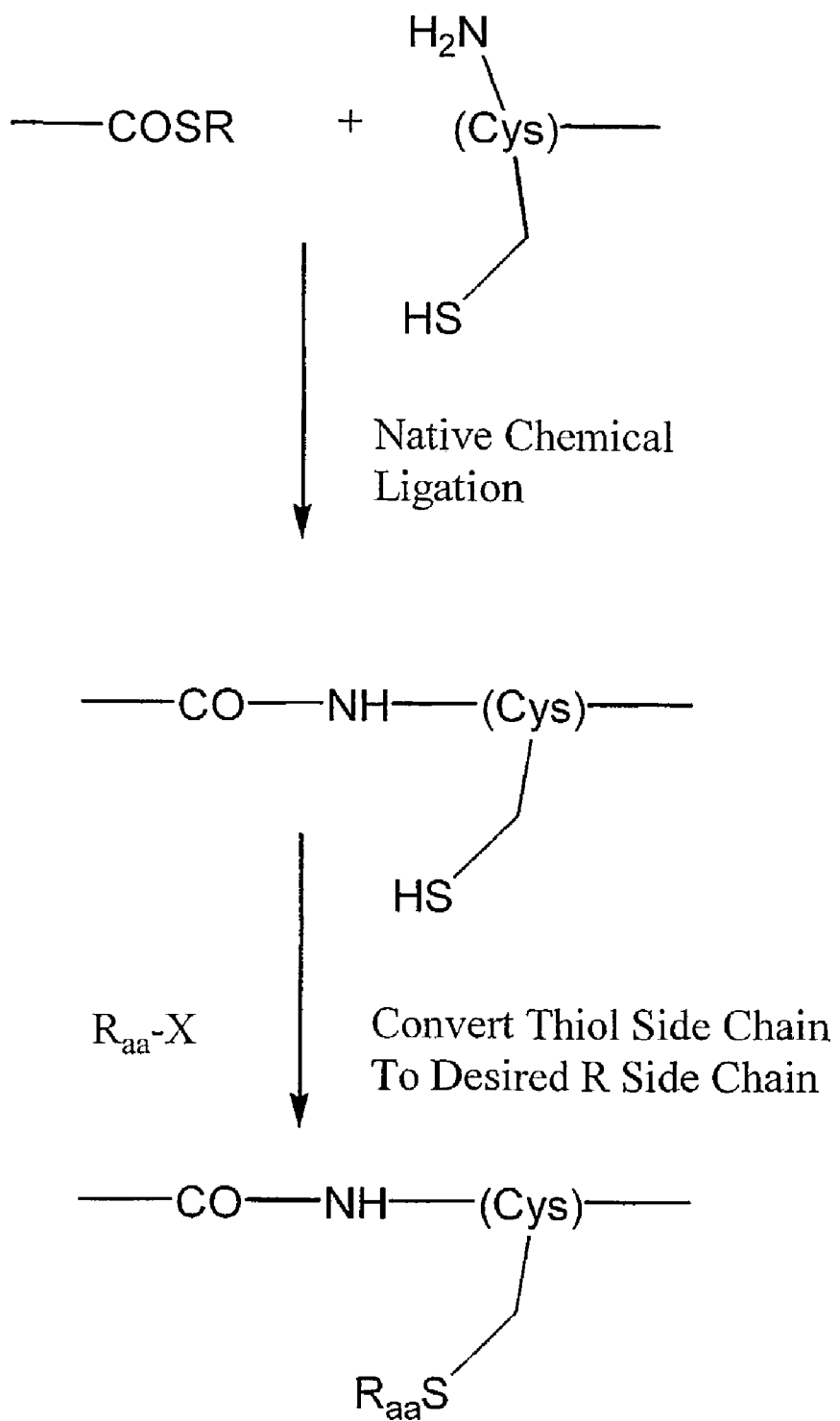
FIG. 1 illustrates the overall reactions of pseudo native chemical ligation.

The present invention concerns methods and compositions for extending the technique of native chemical ligation to permit the ligation of a wider range of peptides, polypeptides, other polymers and other molecules via an amide bond. The invention further provides methods and uses for such proteins and derivatized proteins. The invention is particularly suitable for use in the synthesis of optionally polymer-modified, synthetic bioactive proteins, and of pharmaceutical compositions that contain such proteins.

In detail, the invention provides a synthetic protein (especially a protein having a monomer molecular weight greater than about 25 kDa) containing a pseudo-amino acid residue whose side chain has the formula: —S—$R_{aa}$, where $R_{aa}$ is an optionally substituted terminal portion of a ribosomally-specified amino acid side chain, or an analog of the terminal portion of a ribosomally-specified amino acid side chain.

The invention particularly provides the embodiment of such a synthetic protein wherein the protein has a biological activity possessed by a ribosomally-produced bioactive protein.

The invention further concerns such synthetic proteins wherein a plurality of amino acid residues of the protein are bound to adjacent amino acid residues by an amide bond, and such synthetic proteins wherein a plurality of amino acid residues wherein at least one of such amino acid residues is bonded to an adjacent amino acid residue by a non-amide bond (e.g., a thioester bond, a thioether bond, and an oxime bond).

The invention further concerns such synthetic proteins wherein the pseudo-amino acid residue is a D-configuration amino acid residue or is an L-configuration amino acid residue, or wherein such synthetic proteins contain both pseudo-amino acid residue(s) in the D-configuration and pseudo-amino acid residue(s) in the L-configuration.

The invention further concerns such synthetic proteins wherein the pseudo-amino residue is selected from the group consisting of a pseudo-arginine; a pseudo-asparagine; a pseudo-aspartate; a pseudo-dopamine; a pseudo-glutamate; a pseudo-glutamine; a pseudo-histidine; a pseudo-isoleucine; a pseudo-leucine; a pseudo-lysine; a pseudo-methionine; a pseudo-phenylalanine; a pseudo-serine; a pseudo-threonine; a pseudo-tryptophan; a pseudo-tyrosine; and a pseudo-valine.

The invention further concerns such synthetic proteins wherein the ribosomally-specified bioactive protein is a mammalian protein (e.g., a human, simian, bovine, murine, porcine, ovine, or equine protein).

The invention further concerns such synthetic proteins wherein the protein has a bioactivity selected of a protein receptor or fragment thereof, of a protein receptor ligand or fragment thereof, or of a cytokine (especially wherein the cytokine is selected from the group consisting of an interleukin, a lymphokine, a RANTES protein, an erythropoiesis stimulating protein, tumor necrosis factor (TNF), an interferon, a growth factors and a single peptide hormone).

The invention further concerns the synthetic proteins SEP-0, SEP-1, and SEP-3.

The invention further concerns all such synthetic proteins wherein one or more of their amino acid residues are modified by one or more polymer adducts, and particularly wherein the synthetic protein comprises one or more amino acid residues that are modified by one or more polymer adducts at amino acid residue(s) that correspond to at least one of the glycosylation sites of a ribosomally-encoded bioactive protein.

The invention also provides a molecularly homogeneous pharmaceutical composition comprising a synthetic protein, wherein the protein possesses a biological activity that mimics a biological activity associated with a ribosomally-specified bioactive mammalian protein, and has a monomer molecular weight greater than about 25 kDa, and contains a pseudo-amino acid residue whose side chain has the formula: —S—$R_{aa}$, where $R_{aa}$ is selected from the group consisting of an optionally substituted terminal portion of a ribosomally-specified amino acid side chain, or an analog thereof.

The invention also provides a method of treating a human disease or condition that comprises administering to an individual in need of such treatment an effective amount of a pharmaceutical composition comprising one or more molecularly homogeneous pharmaceutical compositions each comprising a synthetic protein, wherein the synthetic protein has a monomer molecular weight greater than about 25 kDa, and contains a pseudo-amino acid residue whose side chain has the formula: —S—$R_{aa}$, where $R_{aa}$ is selected from the group consisting of an optionally substituted terminal portion of a ribosomally-specified amino acid side chain, or an analog thereof; the synthetic protein possessing a biological activity that mimics a biological activity of a ribosomally-specified bioactive human protein receptor or fragment thereof, protein receptor ligand or fragment thereof, or a cytokine.

The invention also provides a method for synthesizing a desired polypeptide, and the desired polypeptide made through such method, wherein the desired polypeptide has the formula:

$$aa_{NH_2}\text{-Q-}aa_x\text{-}aa_y\text{-W-}aa_{COOH}$$

where Q and W each denote the optional presence of one or more additional amino acid residues, $aa_{NH_2}$ denotes the N-terminal amino acid residue of the polypeptide; $aa_x$ and $aa_y$ denote internal adjacent amino acid residues, having side chains x and y, respectively, and $aa_{COOH}$ denotes the C-terminal amino acid residue of the polypeptide; the method comprising:

(A) ligating a first peptide having the formula: $aa_{NH_2}$-Q-$aa_x$-COSR, wherein R is any group compatible with the thioester group, including, but not limited to, aryl, benzyl, and alkyl groups, to a second peptide having the formula: Cys-W-$aa_{COOH}$ to thereby form the polypeptide: $aa_{NH_2}$-Q-$aa_x$-Cys-W-$aa_{COOH}$; and (B) incubating the polypeptide in the presence of a reagent $R_{aa}$—X, where $R_{aa}$ is a group whose structure mimics the terminal portion of the side chain of amino acid residue $aa_y$; and X is a good leaving group (especially a halogen, such as F, I, or Br); the incubation being under conditions sufficient to form the desired polypeptide.

The invention further provides the embodiment of such method and polypeptide wherein the amino acid residue $aa_y$ is selected from the group consisting of a pseudo-arginine; a pseudo-asparagine; a pseudo-aspartate; a pseudo-dopamine; a pseudo-glutamate; a pseudo-glutamine; a pseudo-histidine; a pseudo-isoleucine; a pseudo-leucine; a pseudo-lysine; a pseudo-methionine; a pseudo-phenylalanine; a pseudo-serine; a pseudo-threonine; a pseudo-tryptophan; a pseudo-tyrosine; and a pseudo-valine.

DESCRIPTION OF THE PREFERRED EMBODIMENTS

The present invention concerns methods and compositions for extending the technique of native chemical ligation to permit the ligation of a wider range of peptides, polypeptides, other polymers and other molecules via an amide bond, thus facilitating the chemical synthesis of such molecules. The invention further provides methods and uses for such proteins and derivatized proteins. The invention is particularly suitable for use in the synthesis of optionally polymer-modified, synthetic bioactive proteins, preferably having a monomer molecular weight of greater than about 25 kDa, and of pharmaceutical compositions that contain such proteins.

I. The Chemical Synthesis of Bioactive Peptides and Proteins

Typically, the synthesis of bioactive peptides and proteins employs the "Merrifield"-chemistry stepwise solid phase peptide synthesis protocol developed in the early 1960's, using standard automated peptide synthesizers. Such synthesis may employ solid or solution phase ligation strategies. While such chemistry may be readily employed to produce many polypeptides, it is unsuitable for the production of proteins or large polypeptides due to associated yield losses, by-product production, and incomplete reactions. To address these limitations, techniques of chemical ligation have been developed that permit one to ligate together preformed peptide fragments in order to achieve the synthesis of larger polypeptides and proteins.

Chemical ligation involves the formation of a selective covalent linkage between a first chemical component and a second chemical component. Unique, mutually reactive, functional groups present on the first and second components can be used to render the ligation reaction chemoselective. For example, the chemical ligation of peptides and polypeptides involves the chemoselective reaction of peptide or polypeptide segments bearing compatible Unique, mutually reactive, C-terminal and N-terminal amino acid residues. Several different chemistries have been utilized for this purpose, examples of which include native chemical ligation (Dawson, et al., *Science* (1994) 266:776–779; Kent, et al., WO 96/34878; Kent, et al., WO 98/28434), oxime forming chemical ligation (Rose, et al., *J. Amer. Chem. Soc.* (1994) 116:30–34), thioester forming ligation (Schnölzer, et al., *Science* (1992) 256:221–225), thioether forming ligation (Englebretsen, et al., *Tet. Letts.* (1995) 36(48):8871–8874), hydrazone forming ligation (Gaertner, et al., *Bioconj. Chem.* (1994) 5(4):333–338), and thiazolidine forming ligation and oxazolidine forming ligation (Zhang, et al., *Proc. Natl. Acad. Sci.* (1998) 95(16):9184–9189; Tam, et al., WO 95/00846; U.S. Pat. No. 5,589,356) or by other methods (Yan, L. Z. and Dawson, P. E., "Synthesis of Peptides and Proteins without Cysteine Residues by Native Chemical Ligation Combined with Desulfurization," *J. Am. Chem. Soc.* 2001, 123, 526–533, herein incorporated by reference; Gieselnan et al., Org. Lett. 2001 3(9):1331–1334; Saxon, E. et al., "Traceless" Staudinger Ligation for the Chemoselective Synthesis of Amide Bonds. Org. Lett. 2000, 2, 2141–2143).

Where the ligation involves the joining of a polypeptide that possesses an N-terminal cysteine residue, the procedure of native chemical ligation is preferably employed (Dawson, et al., *Science* (1994) 266:776–779; Kent, et al., WO 96/34878; Kent, et al., WO 98/28434; U.S. Pat. No. 6,326,468 all herein incorporated by reference). Native chemical ligation involves a chemoselective reaction between a first peptide or polypeptide segment having a C-terminal α-carboxythioester moiety and a second peptide or polypeptide having an N-terminal cysteine residue. A thiol exchange reaction yields an initial thioester-linked intermediate, which spontaneously rearranges to give a native amide bond at the ligation site while regenerating the cysteine side chain thiol. In many instances, the sequence of the natural protein will comprise suitably placed cysteine residues such that polypeptide fragments having an N-terminal cysteine residue may be synthesized and used in a native chemical ligation reaction.

Although this methodology has proven to be practical, robust and useful for the synthesis of large polypeptides and proteins, its requirements for a cysteine residue at the site of ligation limits its applicability. Cysteine is one of the least common amino acids. A typical protein domain comprises 150–200 amino acids; many proteins contain regions of greater than 60 amino acids in length that contain no cysteine residues. One solution to this problem involves designing a non-naturally occurring protein in which one or more of the protein's naturally occurring amino acid residues have been replaced with cysteine residues, thus permitting the native chemical ligation method to be employed. This solution is often complicated by the unpredictable effects that the introduction of a cysteine residue may have on protein structure or function. Such cysteine residues may be used to covalently immobilize the synthesized protein.

The present invention provides two alternative solutions to this problem that may be employed separately or conjunctively. The first such solution (termed herein "Pseudo-Native Chemical Ligation") involves the use of non-naturally occurring pseudo-amino acid residues at preselected positions in the peptides employed in the protein synthesis. The structures of such pseudo-amino acids mimic both the structures of cysteine and the structures of the amino acids that are naturally found at such preselected positions in the protein being synthesized. The second such solution (termed herein "Extended Native Chemical Ligation") is described in U.S. patent application Ser. No. 60/231,339 (Kent, et al., filed: Sep. 8, 2000), herein incorporated by reference, and involves ligating a first component comprising a carboxyl thioester, and more preferably, an α-carboxyl thioester with a second component comprising an acid stable N-substituted, and preferably, Nα-substituted, 2 or 3 carbon chain amino alkyl or aryl thiol. Each of these solutions is discussed in detail below.

A. Pseudo-Native Chemical Ligation

Pseudo-native chemical ligation is directed to the thioalkylation of cysteine side chains generated at ligation sites from native chemical ligation. A preferred aspect is thioalkylation of cysteine ligation sites wherein at least one peptide contains a native cysteine having its thiol side chain protected with a suitable protecting group.

In a preferred embodiment of the invention, the thiol moiety of a cysteine group is modified into a desired side chain, for example, into the side chain of a ribosomally-specified amino acid, an analog of such an amino acid, or into a non-ribosomally-specified amino acid. As used herein, a ribosomally-specified amino acid is an amino acid that is recognized by ribosomes in the process of protein translation and can be incorporated into a ribosomally produced protein. Considerable published literature exists describing chemical modifications of the cysteine side chain thiol moiety (see, e.g., "Current Protocols in Protein Science," Edited by: John E. Coligan et at., John Wiley & Sons, NY (2000)). Kaiser, E. T. has described the conversion of cysteine residue side chains to mimic the chemical properties of a naturally occurring amino acid side chain (see, e.g., Kaiser, E. T. et al., "Chemical Mutation Of Enzyme Active Sites," Science. Nov. 2, 1984;226(4674):505–11). Additionally, the use of a cysteine side chain to introduce a label into a peptide or protein has been described. Cysteine side chain modifications are reviewed in Chemistry of Protein Conjugation and Crosslinking, S. S. Wong, (1991, CRC Press); Chemical Modification of Proteins, Gary E. Means et al., (1971, Holden-Day), Chemical Modification of Proteins: Selected methods and analytical procedures, Glazer, A. N. et al. (1975, Elsevier); Chemical Reagents for Protein Modification, R L Lundblad (1991, CRC Press). Tam et al. (Biopolymers (1998) 46:319–327) have disclosed the use of homocysteine ($-CH_2-CH_2-SH$) for non-cys native chemical ligation, followed by thioalkylation using methyl p-nitrobenzenesulfonate (methylating reagent) to convert the homocysteine side chain to a native methionine side chain ($-CH_2-CH_2-S-CH_3$). The present invention also can be used for converting homocysteines to pseudo amino acids as well, i.e., to amino acids other than methionine. However, as with the conversion of cysteines described herein, in accordance with the present invention it is necessary to use protecting groups to avoid destruction of native cysteines involved in disulfide pairing for peptides that contain at least one native cysteine that one does not wish to convert. Suitable protecting groups are described below.

While the method of pseudo-native chemical ligation does not facilitate the mimicking of the side chains of certain ribosomally-specified amino acids (e.g., the side chains of glycine, alanine, valine, and proline) (alanine's side chain can, however, be formed through a desulfurization reaction (Yan, L. Z. and Dawson, P. E., "Synthesis of Peptides and Proteins without Cysteine Residues by Native Chemical Ligation Combined with Desulfurization," *J. Am. Chem. Soc.* 2001, 123, 526–533, herein incorporated by reference), it may be used to form side chains that mimic many ribosomally-specified or non-encoded amino acids. Amino acids produced in accordance with the pseudo-native chemical ligation method of the present invention will contain a thioether linkage, and will have no beta-branching (in that they will all include a methyl group at the beta position, i.e., aa-$\beta CH_2$—S—. Thus, the pseudo-amino acid versions of the beta-branched amino acids, isoleucine and threonine can be made to have the pendant side chain structure, without having the beta geometry and its attendant constraints.

Significantly, the methods of the present invention may be used to form amino acid side chains that are the same length as that of ribosomally-specified amino acids, or are longer or shorter than such length. Such alteration in side chain length can be used to stabilize (or destabilize) the three-dimensional conformation to increase protein stability (or to enhance the ability of the protein to alter its conformation and thereby accept a different range of substrates, inhibitors, receptors, ligands, etc. relative to those accepted by the naturally occurring protein. For example, Cys-$CH_2$—SH+Br—$CH_2$—COOH yields Cys-$CH_2$—S—$CH_2$—COOH (such "pseudo-glutamic acid" has one additional side chain atom, namely the —S— group; alternatively, if used in the place of aspartic acid, it will possess two additional side chain atoms, namely a —$CH_2$—S— group). Other side chains have the same number of atoms in the side chain, but differ by inclusion of the thioether linkage (—S—). For example, Cys-$CH_2$—SH+Br—$CH_2$—$CH_2$—NH-PG, followed by removal of PG yields Cys-$CH_2$—S—$CH_2$—$CH_2$—$NH_2$. The resulting structure has no additional atoms in the side chain, but one —$CH_2$— group is replaced with —S—. Methionine is another example here, Cys-$CH_2$—SH+I—$CH_2$—$CH_3$ yields Cys-$CH_2$—S—$CH_2$—$CH_3$ (versus native met structure of Met-$CH_2$—$CH_2$—S—$CH_3$); thus the thioether is relocated. Arginine also: Cys-$CH_2$—SH+Br—$CH_2$—NH—CH((—$NH_2$)(=$NH_2^+$)) yields Cys-$CH_2$—S—$CH_2$—NH—CH((—$NH_2$)(=$NH_2^+$)). Preferably, protection of reactive amino groups, particularly for the constructing pseudo lysine can be employed to avoid unwanted side reactions. Once the thioalkylation reaction is performed, the protecting group can be removed.

In general, where the desire is to mimic a naturally occurring protein as closely as possible, it is most preferred to employ a pseudo amino acid molecule having a side chain length that is the same length as that of the ribosomally-specified amino acid normally present at such position in the protein; it is less preferred to employ a pseudo amino acid molecule having a side chain length that is one atom longer than that of the ribosomally-specified amino acid, and still less preferred to employ a pseudo amino acid molecule having a side chain length that is two atoms longer than that of the ribosomally-specified amino acid. Moreover, its is preferred to select a cysteine ligation site that is in a location where genetic changes are not likely to disrupt function or where amino acids at that site in related proteins are conserved. Such sites can be identified by alanine scanning, homology modeling, and other methods.

In pseudo-native chemical ligation, a peptide containing an amino terminal cysteine residue is ligated to a peptide having a carboxy terminal thioester, as in native chemical ligation. The thiol side chain of the cysteine is then reacted with a compound of the formula $R_{aa}$—X, where X is a good leaving group, and $R_{aa}$ is a group whose structure mimics the terminal portion of the side chain of an ribosomally-specified or synthetic amino acid.

Significantly, the reactions of pseudo-native chemical ligation work with either the natural L-configuration of cysteine side chain, or the D-configuration. Use of the D-configuration can impart protease resistance at that ligation site, and thus may be desired when increased stability to proteolysis is desired. However, in using the D-cysteine, the backbone structure at that side will be altered. Such alteration, in addition to protease resistance, may be desired to alter bioactivity. However, to minimize impact on bioactivity, it is preferred to locate the D-cysteine at a site of high flexibility, such as a disorded region, such as at a disorded loop that will be located on the surface of the resulting folded molecule, on at a disorded terminus of the molecule. Desirably, the reactions of pseudo-native chemical ligation may be used to place large, charged side chains (e.g., the side chains of Lys, Arg, Asp or Glu) on the surface of the synthesized molecule.

Examples of suitable good leaving groups, X, include halogens, especially Iodine and Bromine. Examples of $R_{aa}$ groups include $PO_4$, COOH, COO, $CONH_2$, guanidinium, amine, alkyl, substituted alkyl, aryl, substituted aryl, imidazole, alkylated imidazole, indole, or alkylated indole groups.

The selection of which $R_{aa}$ to employ will depend upon the amino acid side.

Thus, for example, a desired polypeptide or protein having the amino acid sequence:

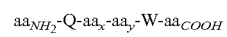

$$aa_{NH_2}\text{-Q-}aa_x\text{-}aa_y\text{-W-}aa_{COOH}$$

where Q and W each denote the optional presence or absence of additional amino acid residues, and $aa_x$ and $aa_y$ denote internal adjacent residues (having side chains x and y, respectively), and $aa_{NH_2}$ and respectively denote the amino (N-) terminal residue and the carboxy (C-) terminal residue of the polypeptide or protein and be synthesized by preparing two peptide fragments.

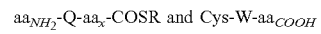

$$aa_{NH_2}\text{-Q-}aa_x\text{-COSR and Cys-W-}aa_{COOH}$$

where Cys denote the replacement of $aa_y$ with cysteine, and R is any group compatible with the thioester group, including, but not limited to, aryl, benzyl, and alkyl groups. Examples of R include 3-carboxy-4-nitrophenyl thioesters, benzyl esters, and mercaptoproprionic acid leucine esters (See, e.g., Dawson et al., Science (1994) 266:776–779; Canne et al. Tetrahedron Lett. (1995) 36:1217–1220; Kent, et al., WO 96/34878; Kent, et al., WO 98/28434; Ingenito et al., JACS (1999) 121(49):11369–11374; and Hackeng et al., Proc. Natl. Acad. Sci. U.S.A. (1999) 96:10068–10073). Other examples include dithiothreitol, or alkyl or aryl thioesters, which can be produced by intein-mediated biological techniques, which also are well Known (See, e.g., Chong et al., Gene (1997) 192:277–281; Chong et al., Nucl. Acids Res. (1998) 26:5109–5115; Evans et al., Protein Science (1998) 7:2256–2264; and Cotton et al., Chemistry &

Biology (1999) 6(9):247–256); and then ligating the fragments together to form:

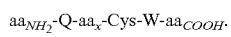

The ligated fragment is then reacted with $R_y$—X, where $R_y$ is a side group that mimics the structure of the y side chain). The reaction is conducted under conditions sufficient to convert the thiol group of the cysteine into a "pseudo-y" side chain. For example, if $R_{aa}$ is selected to be $CH_2$—COOH or $(CH_2)_2$—COOH, then the reaction will lead to the formation an amino acid residue that mimics the structure and function of aspartic acid ("pseudo-Asp") or glutamic acid ("pseudo-Glu"). As will be appreciated, in light of the above description, more complicated synthesis can be conducted employing more than two peptide fragments.

Native chemical ligation involving "pseudo amino acids" according to the present invention significantly expands the applicability of the native chemical ligation method for the chemical synthesis of proteins. Native chemical ligation involving "pseudo amino acids" uses the same chemistry in the ligation step, forming a peptide bond at the Cys residue with a native thiol-containing side chain functionality; in a unique second step, the native thiol-containing side chain of the Cys at the site of ligation is converted by chemoselective reaction to yield a non-native side chain that contains the same functional group as a genetically-encoded amino acid, but a non-native side chain.

For example, the cysteine at the ligation site can be reacted with bromoacetic acid (or other haloacetic acid) at neutral pH in water; only the unprotected thiol of the Cys at the ligation site reacts under these conditions to give a polypeptide containing an S-carboxymethylated residue at the ligation site, viz:

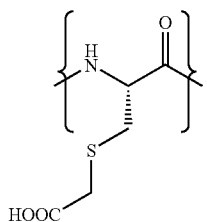

This non-native amino acid contains a carboxyl moiety on the side chain, the same functional group as a glutamic acid or an aspartic acid residue. The S-carboxymethylated Cys is referred to herein as a "pseudo glutamic acid" ("pseudo-glutamate," "pseudo-Glu") (where one extra side chain atom is present and is the —S— group forming a thioether linkage) (it also may be referred to as a "pseudo-aspartic acid" where two extra side chain atoms are present, one of which is the —S— group forming a thioether linkage). For many proteins, the simple preservation of the charged carboxylate side chain even in this "pseudo amino acid" will be sufficient to retain or impart desired properties to the protein. A key difference is that it functions as a native chemical ligation site at a position devoid of a suitable cysteine.

Use of other reagents to modify the side chain thiol in Cys residues at the ligation site(s) can give other "pseudo amino acid" residues. For example, reaction of the thiol with a haloacetamide, e.g. bromoacetamide, will give a "pseudo glutamine" at the ligation site, viz:

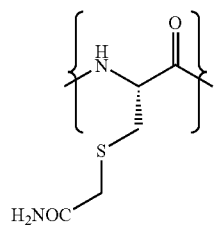

Similarly, reaction with an N-protected haloalkylamine, e.g.

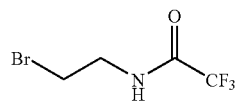

followed by removal of the amino protecting group will give a 'pseudo-lysine' residue, viz:

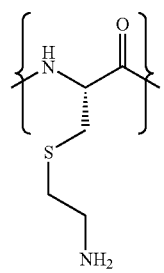

Reaction of the Cys residue(s) at the ligation site(s) with a suitable haloalkane, e.g.

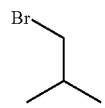

will yield a 'pseudo leucine' amino acid, viz:

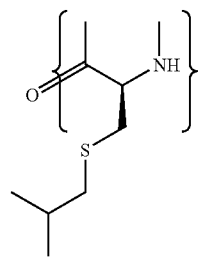

Other suitably chosen aryl-containing halides, where R can be H, OH, aryl etc., e.g.

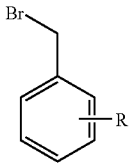

can be used similarly to generate pseudo amino acids corresponding to Phe, Tyr, or Trp residues, viz:

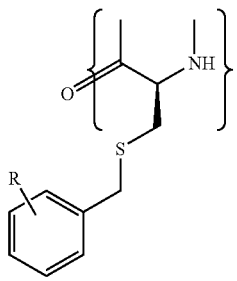

A significant feature of this approach is that cysteine residues that one does not wish to modify in the reacting segments be side chain protected, e.g. as Cys(Acm), to prevent chemical modification of Cys residues other than the one(s) at the ligation site(s), or that any other Cys residues in the reacting segments be intended for the simultaneous formation of identical 'pseudo amino acids' by the chemical modification reaction after ligation. It will be appreciated that the same principles apply to the use of homocysteine at the ligation site. It will also be appreciated that selenocysteine can be employed at a ligation site through selenocysteine-mediated native chemical ligation, and converted by similar alkylation reactions to generate pseudo amino acids of the invention, where a selenoether group replaces the thioether group.

As used herein, the symbol φ denotes a benzyl group; IM denotes an imidazole group, and IN denotes an indole group; PG denotes a protecting group. Below is a summary of $R_{aa}$ side groups that may be used to synthesize peptides containing pseudo-amino acid residues in accordance with the present invention (where X is a halogen (I, Br, Cl, F, with I and Br preferred for most, and F preferred for φ attachment):

Basic Amino Acids:
Lys (no extra atoms)
—$CH_2$—SH+X—$CH_2$—$CH_2$—NH-PG, followed by deprotection gives —$CH_2$—S—$CH_2$—$CH_2$—$NH_2$
Arg (no extra atoms)
—$CH_2$—SH+X—$CH_2$—NH—C(($NH_2$)(=$NH_2$+)) gives —$CH_2$—S—$CH_2$—NH—C(($NH_2$)(=$NH_2$+))
His (2 extra atoms)
—$CH_2$—SH+X—$CH_2$-IM-PG, followed by deprotection gives —$CH_2$—S—$CH_2$-IM Acidic Amino Acids:
Asp (2 extra atoms)
—$CH_2$—SH+X—$CH_2$—COOH gives —$CH_2$—S—$CH_2$—COOH
Glu (1 extra atom)
—$CH_2$—SH+X—$CH_2$—COOH gives —$CH_2$—S—$CH_2$—COOH Uncharged Polar Amino Acids:
Tyr (no or 1 extra atom)
—$CH_2$—SH+F-φ-pOH gives —$CH_2$—S-φ-pOH (no extra atoms, same geometry
—$CH_2$—SH+Br/I—$CH_2$-φ-pOH gives —$CH_2$—S—$CH_2$-φ-pOH (1 extra atom)
Gln (1 extra atom)
—$CH_2$—SH+X—$CH_2$—C(O)($NH_2$) gives —$CH_2$—S—$CH_2$—C(O)($NH_2$)
Asn (2 extra atoms)
—$CH_2$—SH+X—$CH_2$—C(O)($NH_2$) gives —$CH_2$—S—$CH_2$—C(O)($NH_2$)
Ser (2 or 3 extra atoms)
—$CH_2$—SH+X—$CH_2$OH gives —$CH_2$—S—$CH_2$OH (2 extra atoms)
—$CH_2$—SH+X—$CH_2$—$CH_2$OH) gives —$CH_2$—S—$CH_2$—$CH_2$OH (3 extra atoms)
Thr (2 or 3 extra atoms, missing beta branching)
—$CH_2$—SH+X—CH(($CH_3$)(O-PG)) followed by removal of PG gives —$CH_2$—S—CH(($CH_3$)(OH)) (2 extra atom)
—$CH_2$—SH+X—$CH_2$—CH(($CH_3$)(O-PG)) followed by removal of PG gives —$CH_2$—S—$CH_2$—CH(($CH_3$)(OH)) (3 extra atoms)

Non-Polar Amino Acids:
Leu (1 or 2 extra atoms)
—$CH_2$—SH+X—CH(($CH_3$)($CH_3$)) gives —$CH_2$—S—CH(($CH_3$)($CH_3$)) (1 extra atom)
—$CH_2$—SH+X—$CH_2$—CH(($CH_3$)($CH_3$)) gives —$CH_2$—S—$CH_2$—CH(($CH_3$)($CH_3$)) (2 extra atoms)
Ile (2 or 3 extra atoms, missing beta branching)
—$CH_2$—SH+X—CH($CH_3$)—$CH_2$—$CH_3$ gives —$CH_2$—S—CH($CH_3$)—$CH_2$—$CH_3$ (2 extra atoms)
—$CH_2$—SH+X—$CH_2$—CH($CH_3$)—$CH_2$—$CH_3$ gives —$CH_2$—S—$CH_2$—CH($CH_3$)—$CH_2$—$CH_3$ (3 extra atoms)
Phe (1 or 2 extra atoms)
—$CH_2$—SH+F-φ gives —$CH_2$—S-φ (1 extra atom)
—$CH_2$—SH+Br/I—$CH_2$-φ gives —$CH_2$—S—$CH_2$-φ (2 extra atoms)
Met (no extra atoms)
—$CH_2$—SH+I—$CH_2$—$CH_3$ gives —$CH_2$—S—$CH_2$—$CH_3$
Trp (1 extra atom)
—$CH_2$—SH+F-IN gives —$CH_2$—S-IN The general pseudo chemical ligation reaction is illustrated in FIG. 1. Preferred $R_{aa}$ and X groups that can be used to form preferred pseudo-amino acids are shown in Table I. Residues are shown as uncharged, however, it will be appreciated that ionizable groups such as $NH_2$ or COOH may be in their charged form, or provided as salts. All reactions except that used to form pseudo-lysine are aqueous and are conducted at a pH of 8–9, where the stochiometry and optimization of the reactions can be adjusted following standard protocols. Pseudo-lysine is formed in an aqueous reaction conducted at pH 8–9, followed by reaction in piperidine/$H_2O$ (trifluoracetic acid (TFA)).

TABLE I

| Raa-X Reagent | Product of Reaction | Pseudo-Amino Acid | Mimics or Replaces |
|---|---|---|---|
| X—CH$_2$COOH (X = I, Br) | —Cys— with side chain —CH$_2$—S—CH$_2$COOH | Pseudo-Asp (+2 atoms) <br> Pseudo-Glu (+1 atom) | Aspartic Acid <br> Glutamic Acid |
| X—(CH$_2$)$_2$COOH (X = I, Br) | —Cys— with side chain —CH$_2$—S—(CH$_2$)$_2$COOH | Pseudo-Glu (+2 atoms) | Glutamic Acid |
| X—(CH$_2$)—C(O)NH$_2$ (X = I, Br) | —Cys— with side chain —CH$_2$—S—CH$_2$—C(=O)NH$_2$ | Pseudo-Gln (+1 atom) <br> Pseudo-Asn (+2 atoms) | Glutamine <br><br> Asparagine |
| X—CH$_2$OH (X = I, Br) | —Cys— with side chain —CH$_2$—S—CH$_2$OH | Pseudo-Ser (+2 atoms) | Serine |
| X—CHOHCH$_3$ (X = I, Br) | —Cys— with side chain —CH$_2$—S—CHOH—CH$_3$ | Pseudo-Thr (+2 atoms) | Threonine |
| X—CH$_2$CHOHCH$_3$ (X = I, Br) | —Cys— with side chain —CH$_2$—S—CH$_2$—CHOH—CH$_3$ | Pseudo-Thr (+3 atoms) | Threonine |
| X—CH$_2$CH$_2$OH (X = I, Br) | —Cys— with side chain —CH$_2$—S—CH$_2$CH$_2$OH | Pseudo-Ser (+3 atoms) | Serine |
| X—(CH$_2$)$_2$NH—PG (X = I, Br) | —Cys— with side chain —CH$_2$—S—CH$_2$CH$_2$—NH$_2$ | Pseudo-Lys | Lysine |
| X—CH$_2$NH—C(NH$_2$)$_2$ (X = I, Br) | —Cys— with side chain —CH$_2$—S—CH$_2$—NH—C(=NH)NH$_2$ | Pseudo-Arg | Arginine |
| X—(CH$_2$)$_2$NH—C(NH$_2$)$_2$ (X = I, Br) | —Cys— with side chain —CH$_2$—S—CH$_2$CH$_2$—NH—C(=NH)NH$_2$ | Pseudo-Arg (+1 atom) | Arginine |
| X—CH$_2$CH$_3$ (X = I, Br) | —Cys— with side chain —CH$_2$—S—CH$_2$CH$_3$ | Pseudo-Met | Methionine |

TABLE I-continued

| Raa-X Reagent | Product of Reaction | Pseudo-Amino Acid | Mimics or Replaces |
|---|---|---|---|
| X-ψ<br>(X = F) | —Cys— with —S—phenyl | Pseudo-Phe<br>(+1 atoms) | Phenyl-alanine |
| X—CH$_2$ψ<br>(X = I, Br) | —Cys— with —S—CH$_2$—phenyl | Pseudo-Phe<br>(+2 atoms) | Phenyl-alanine |
| X-ψ-OH<br>(para)<br>(X = I, Br) | —Cys— with —S—(p-hydroxyphenyl) | Pseudo-Tyr | Tyrosine |
| X—CH$_2$ψ-OH<br>(para)<br>(X = I, Br) | —Cys— with —S—CH$_2$—(p-hydroxyphenyl) | Pseudo-Tyr<br>(+1 atoms) | Tyrosine |
| X—CH$_2$ψ-OPO$_3$<br>(para)<br>(X = I, Br) | —Cys— with —S—CH$_2$—(p-phosphophenyl) | Pseudo-Phospho-tyr | Phospho-tyrosine |
| X—CH$_2$ψ-(OH)$_2$<br>(meta para)<br>(X = I, Br) | —Cys— with —S—CH$_2$—(3,4-dihydroxyphenyl) | Pseudo-Dopa | Dopamine |
| X—CH(COOH)$_2$<br>(X = I, Br) | —Cys— with —S—CH(COOH)$_2$ | Pseudo-Gla | γ-carboxy Glutamic Acid |
| X—CH$_2$-IM-PG<br>(X = I, Br) | —Cys— with —S—CH$_2$-imidazole | Pseudo-His | Histidine |
| X—CH$_2$-IN<br>(X = F, I, Br) | —Cys— with —S—CH$_2$-indole | Pseudo-Trp | Tryptophan |
| X—CH—(CH$_3$)$_2$<br>(X = I, Br) | —Cys— with —S—CH(CH$_3$)$_2$ | Pseudo-Leu<br>(+1 atoms)<br>Pseudo-Val<br>(+2 atoms) | Leucine<br><br>Valine |

TABLE I-continued

| Raa-X Reagent | Product of Reaction | Pseudo-Amino Acid | Mimics or Replaces |
|---|---|---|---|
| X—CH$_2$CH—(CH$_3$)$_2$ (X = I, Br) | —Cys— CH$_2$—S—CH$_2$—CH(CH$_3$)$_2$ | Pseudo-Leu (+2 atoms) | Leucine |
| X—CH(CH$_3$)—CH$_2$—CH$_3$ (X = I, Br) | —Cys— CH$_2$—S—CH(CH$_3$)—CH$_2$CH$_3$ | Pseudo-Ile (+2 atoms) | Isoleucine |
| X—CH$_2$—CH(CH$_3$)—CH$_2$—CH$_3$ (X = I, Br) | —Cys— CH$_2$—S—CH$_2$—CH(CH$_3$)—CH$_3$ | Pseudo-Ile (+3 atoms) | Isoleucine |
| X—(CH$_2$)$_2$NH—C(O)CF$_3$ (X = I, Br) | —Cys— CH$_2$—S—(CH$_2$)$_2$—NH—C(O)—CF$_3$ | Pseudo-N-(ethyl) trifluoroacetamide | N-(ethyl) trifluoroacetamide |
| X-ammonium 4-chloro-7-sulfobenzofurazan (X-SBF) (X = I, Br) | —Cys— CH$_2$—S—[benzofurazan]—SO$_3^-$NH$_4^+$ | Pseudo-SBF | Ammonium 4-chloro-7-sulfobenzofurazan (SBF) (Pierce Chemical Company) |
| X—CH$_2$-ammonium 4-chloro-7-sulfobenzofurazan (X-SBF) (X = I, Br) | —Cys— CH$_2$—S—CH$_2$—[benzofurazan]—SO$_3^-$NH$_4^+$ | Pseudo-methyl-SBF | Ammonium 4-chloro-7-sulfobenzofurazan (SBF) (Pierce Chemical Company) |

In a further embodiment of the present invention, the thiol group of the cysteine residue can be oxidized (—SH→—SO$_3^-$), or replaced with oxygen to form serine (—SH→—OH). Such replacement can be accomplished by reacting the cysteine with tosyl-Cl (Tos-Cl) thereby converting the thiol group, —SH, into an —S— Tos group. In the presence of strong base, OH replaces the Tos substituent, thereby forming the desired —OH group.

Additionally, the thiol group of the cysteine can be modified through a Michael addition reaction, as shown below: where R is H, alkyl, aryl, alkylaryl, amino, or is a polymer molecule, which may be branched or unbranched, random or block.

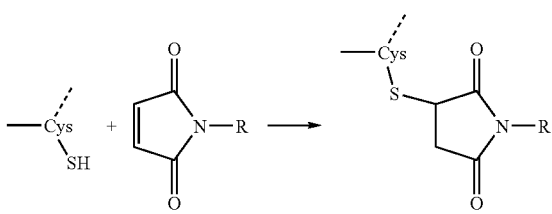

A further aspect of the present invention is directed to the use of a peptide fragment whose amino terminal cysteine residue has been modified to contain an alkylamino (and preferably a methylamino) moiety:

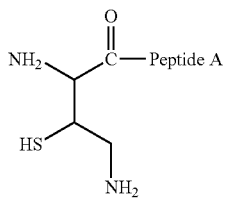

By protecting the amino group of the alkylamino moiety, one can ligate the Pentide A to a second peptide having the general formula: Peptide B-αCOSR. Upon removal of the protecting group, an additional Peptide having the general formula: Peptide C-αCOSR can be ligated to the previously ligated peptides, to form a branched peptide complex:

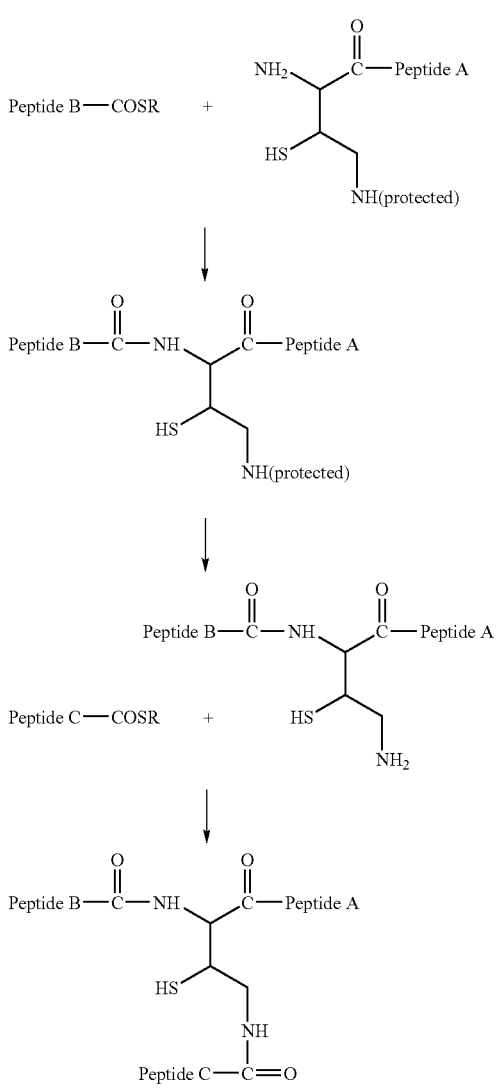

Since the branched protein still contains the thiol group of the cysteine, it will react with an $R_{aa}$—X molecule in the manner described above, to thereby permit further modifications of the side chain. In particular, by using an alkylamide as the R substituent, an additional amino group can be introduced into the molecule, thereby permitting further branching, or further ligation reactions:

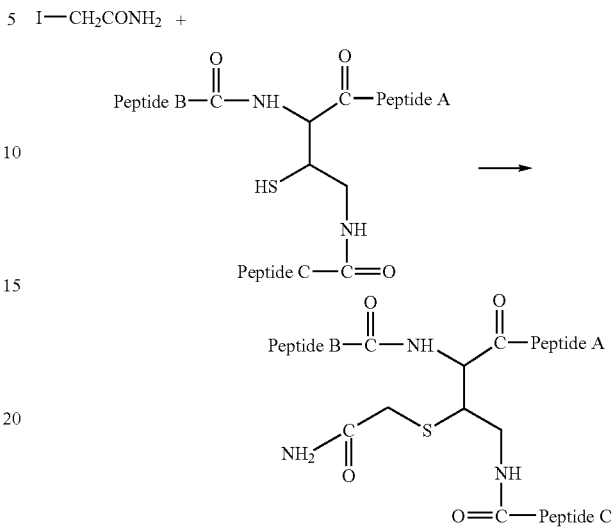

In a further embodiment of the present invention, the modification of the cysteine side chain can be used to introduce any of a variety of labels or binding molecules. For example, labels detectable by electron spin resonance, fluorescence (e.g., ammonium 4-chloro-7-sulfobenzo-furazan (SBF) Pierce Chemical Co.) or magnetic imaging may be employed. Such labeling is useful in the diagnosis of diseases and conditions, as well as in the analysis of molecular interactions (e.g., for measuring distances in integral membrane proteins). The methodology of the present invention has several salient advantages with respect to the use of labels and binding molecules. Such substituents can be incorporated in a site specific, non-random manner. Additionally, the label moiety need only be stable to subsequent chemical ligation steps (if any). Such reactions are generally conducted under very mild conditions (such as those employed in native chemical ligation; removal of Acm or other protecting groups that may optionally be used to protect the thiol groups of other cysteine residues (as with $Hg(CH_2COOH)_2$); and reverse phase HPLC purification). Protection of such additional thiol groups prevents oxidative polymerization of Cys-containing peptides and thus facilitates their purification and handling.

B. Extended Native Chemical Ligation

As indicated above, where the sequence of a natural protein does not contain a suitable cysteine residue, and it is either inconvenient or undesirable to modify a natural protein sequence so as to introduce a cysteine residue at the N-terminus of a polypeptide, the method of "Extended Native Chemical Ligation" may be used to ligate polypeptides whose N-terminus has been modified to contain an N-substituted, and preferably, Nα-substituted, 2 or 3 carbon chain amino alkyl or aryl thiol, and thereby permit the principles of native chemical ligation to be employed with polypeptides lacking cysteine residues (see, U.S. patent application Ser. No. 60/231,339, herein incorporated by reference).

The method of "Extended Native Chemical Ligation" involves ligating a first component comprising a carboxyl thioester, and more preferably, an α-carboxyl thioester with a second component comprising an acid stable N-substituted, and preferably, Nα-substituted, 2 or 3 carbon chain amino alkyl or aryl thiol. Chemoselective reaction between the carboxythioester of the first component and the thiol of the N-substituted 2 or 3 carbon chain alkyl or aryl thiol of the second component proceeds through a thioester-linked intermediate, and resolves into an initial ligation product. More specifically, the thiol exchange occurring between the COSR thioester component and the amino alkyl thiol component generates a thioester-linked intermediate ligation product that after spontaneous rearrangement generates an amide-linked first ligation product through a 5-membered or 6-membered ring intermediate depending upon whether the amino alkyl thiol component has formula I or II, respectively:

J1-C(O)—N(C1(R1)-C2-SH)-J2      I

J1-C(O)—N(C1(R1)-C2(R2)-C3(R3)-SH)-J2      II where J1 is a peptide or polypeptide having one or more optionally protected amino acid side chains, or a moiety of such peptide or polypeptide, a polymer, a dye, a suitably functionalized surface, a linker or detectable marker, or any other chemical moiety compatible with chemical peptide synthesis or extended native chemical ligation; R1, R2 and R3 are independently H or an electron donating group conjugated to C1; with the proviso that at least one of R1, R2 and R3 comprises an electron donating group conjugated to C1; and J2 is a peptide or polypeptide having one or more optionally protected amino acid side chains, or a moiety of such peptide or polypeptide, a polymer, a dye, a suitably functionalized surface, a linker or detectable marker; or any other chemical moiety compatible with chemical peptide synthesis or extended native chemical ligation.

The N-substituted 2 or 3 carbon chain alkyl or aryl thiol [HS—C2-C1(R1)-] or [HS—(C3(R3)-C2(R2)-C1(R1)-] at the ligation site is amenable to being removed, under peptide-compatible conditions, without damage to the product, to generate a final ligation product of formula III, having a native amide bond at the ligation site:

J1-C(O)—HN-J2      III where J1, J2, R1, R2, and R3 are as defined above.

The R1, R2 and R3 groups are selected to facilitate cleavage of the N—C1 bond under peptide compatible cleavage conditions. For example, electron donating groups, particularly if conjugated to C1, can be used to form a resonance stabilized cation at C1 that facilitates cleavage. The chemical ligation reaction preferably includes as an excipient a thiol catalyst, and is carried out around neutral pH conditions in aqueous or mixed organic-aqueous conditions. Chemical ligation of the first and second components may proceed through a five or six member ring that undergoes spontaneous rearrangement to yield an N-substituted amide linked ligation product. Where the first and second components are peptides or polypeptides, the N-substituted amide linked ligation product has formula IV or V:

J1-C(O)—Nα(C1(R1)-C2-HS)—CH(Z2)-C(O)-J2      IV

J1-C(O)—Nα(C1(R1)-C2(R2)-C3(R3)-HS)—CH(Z2)-C(O)-J2      V where J1, J2 and R1, R2, R3 are as defined above and Z2 is an amino acid side chain or a derivative of such side chain..

The conjugated electron donating groups R1, R2 or R3 of the N-substituted amide bonded ligation product facilitate cleavage of the N—C1 bond and removal of the 2 or 3 carbon chain alkyl or aryl thiol from the N-substituted amide-linked ligation product. Removal of the alklyl or aryl thiol chain of the N under peptide-compatible cleavage conditions generates a ligation product having a native amide bond at the ligation site. Where the first and second components are peptides or polypeptides, the ligation product will have the formula:

J1-CONαH—CH(Z2)-C(O)-J2      X

Exemplary R1 subtituents for Formula I are depicted in Table II.

TABLE II

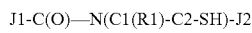

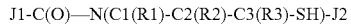

R1 Substituent Groups for Formula I (C1 included for reference)

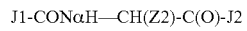

Exemplary R1, R2 and R3 substituents for Formula II are depicted in Table III.

TABLE III

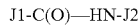

R1, R2 and R3 Substituents (C1 included for reference)

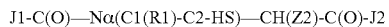

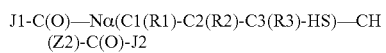

As with the N-substituted 2 carbon chain compounds, positioning of the benzyl and picolyl electron-donating substituents R1', R3' and R5' in the ortho or para positions is necessary to maintain electronic conjugation to the C1 carbon for robust cleavage of the Nα-C1 bond following ligation. However, when R2 and R3 form a benzyl group with C2 and C3, at least one of R1' and R3' comprises a strong electron donating group, where R1' or R3' is selected from methoxy (—OCH3), thiol (—SH), hydroxyl (—OH), and thiomethyl (—SCH3). For the N-substituted 3 carbon chain thiols in which R2 and R3 are hydrogens, R1 comprises a benzyl or picolyl group in which R1', R3' and R5' include either strong or moderate electron-donating groups, or a combination thereof. As with the N-substituted 2 carbon chain alkyl or aryl thiols, the strong electron-donating groups enhance the sensitivity of the 3 carbon chain alkyl or aryl thiol to cleavage following ligation. Thus a particular electron-donating group or combination thereof can be selected accordingly.

Similar to the N-substituted 2 carbon chain compounds, the N-substituted 3 carbon chain compounds of the present invention may include a thiol as a substituent of R1 in the R1' and R5' positions when available for substitution in a construct of interest. Here again the electron-donating thiol group is conjugated to C1 and its introduction at these locations enables the compounds to have two routes for the 6-member ring forming ligation event. It also increases the local concentration of available thiols for reacting with the α-carboxy thioester, and provides for additional conformations in terms of structural constraints that can improve ligation.

Synthesis of the N-terminal N-substituted 2 or 3 carbon chain alkyl or aryl thiol amino acids of the invention can carried out as described herein, for example, in Scheme I and Scheme II, and in accordance with standard organic chemistry techniques known in the art. See, e.g., "Advanced Organic Chemistry, Reactions, Mechanisms, and Structure," 4$^{th}$ Edition, J. March (Ed.), John Wiley & Sons, New York, N.Y., 1992; "Comprehensive Organic Transformations, A Guide to Functional Group Preparations," R. Larock (Ed.), VCH Publishers, New York, N.Y., 1989. They may be synthesized in solution, by polymer-supported synthesis, or a combination thereof. The preferred approach employs N alpha protected N alkylated S-protected amino alkyl- or aryl-thiol amino acid precursors. The reagents utilized for synthesis can be obtained from any number of commercial sources. Also, it will be well understood that the starting components and various intermediates, such as the individual amino acid derivatives can be stored for later use, provided in kits and the like.

In preparing the N-terminal Nα-substituted 2 or 3 carbon chain alkyl or aryl thiol amino acids of the invention, protecting group strategies are employed. The preferred protecting groups (PG) utilized in the various synthesis strategies in general are compatible with Solid Phase Peptide Synthesis ("SPPS"). In some instances, it also is necessary to utilize orthogonal protecting groups that are removable under different conditions. Many such protecting groups are known and suitable for this purpose (See, e.g., "Protecting Groups in Organic Synthesis", 3rd Edition, T. W. Greene and P. G. M. Wuts, Eds., John Wiley & Sons, Inc., 1999; NovaBiochem Catalog 2000; "Synthetic Peptides, A User's Guide," G. A. Grant, Ed., W. H. Freeman & Company, New York, N.Y., 1992; "Advanced Chemtech Handbook of Combinatorial & Solid Phase Organic Chemistry," W. D., Bennet, J. W. Christensen, L. K. Hamaker, M. L. Peterson, M. R. Rhodes, and H. H. Saneii, Eds., Advanced Chemtech, 1998; "Priciples of Peptide Synthesis, 2nd ed.," M. Bodanszky, Ed., Springer-Verlag, 1993; "The Practice of Peptide Synthesis, 2nd ed.," M. Bodanszky and A. Bodanszky, Eds., Springer-Verlag, 1994; and "Protecting Groups," P. J. Kocienski, Ed., Georg Thieme Verlag, Stuttgart, Germany, 1994). Examples include benzyloxycarbonyl (Z), Boc, Bpoc, Trt, Nps, FmocCl—Z, Br—Z; NSC; MSC, Dde, etc. For sulfur moieties, examples of suitable protecting groups include, but are not limited to, benzyl, 4-methylbenzyl, 4-methoxybenzyl, trityl, ACM, TACAM, xanthyl, disulfide derivatives, picolyl, and phenacyl.

More particularly, the Nα-substituted 2 or 3 carbon chain alkyl or aryl thiols can be prepared in accordance with Scheme I (Solid-Phase preparation of the Nα-substituted precursor), Scheme II (Solution-Phase preparation of the Nα-substituted precursor ). In Scheme I, Nα-substituted 2 or 3 carbon chain alkyl or aryl thiols are assembled directly on the solid phase using standard methods of polymer-supported organic synthesis, while the Nα-protected, N-alkylated, S-protected, aminoalkyl or arylthiol amino acid precursor of Scheme II are coupled to the resin using standard coupling protocols. Where racemic or diastereomeric products are produced, it may be necessary to separate these by standard methods before use in extended native chemical ligation.

Scheme I
Solid-Phase Synthesis Of ECL Auxiliary Derivatized Molecules

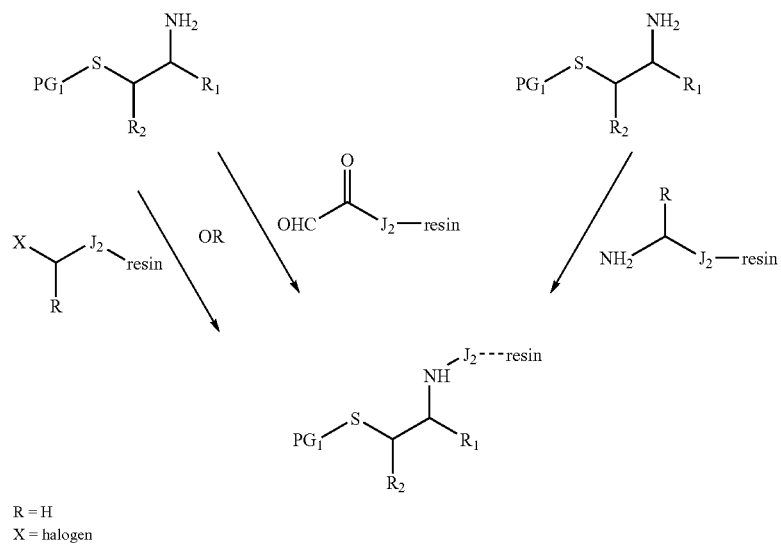

R = H
X = halogen

Scheme II

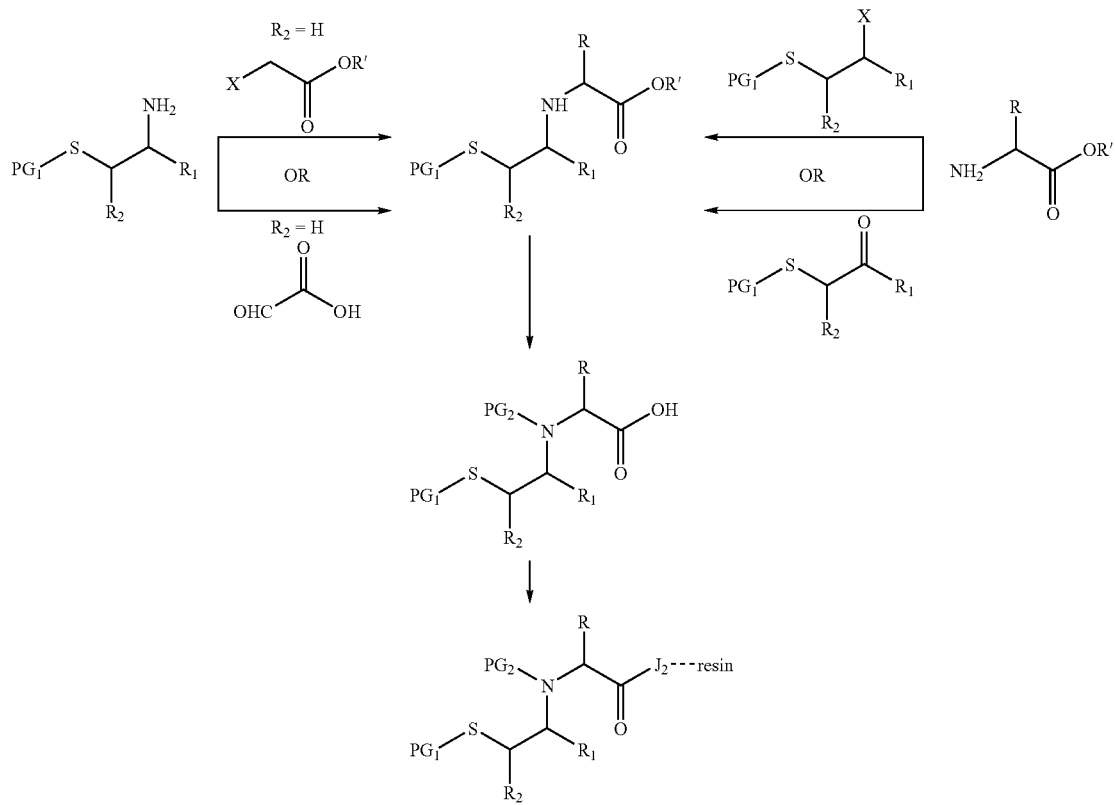

The α-carboxythioesters can be generated by chemical or biological methods following standard techniques known in the art, such as those described herein, including the Examples. For chemical synthesis, α-carboxythioester peptides can be synthesized in solution or from thioester-generating resins, which techniques are well known (See, e.g., Dawson et al., supra; Canne et al., supra; Hackeng et al., supra, Aimoto et al.). For instance, chemically synthesized thioester peptides can be made from the corresponding peptide α-thioacids, which in turn, can be synthesized on a thioester-resin or in solution, although the resin approach is preferred. The peptide-α-thioacids can be converted to the corresponding 3-carboxy-4-nitrophenyl thioesters, to the corresponding benzyl ester, or to any of a variety of alkyl thioesters. All of these thioesters provide satisfactory leaving groups for the ligation reactions, with the 3-carboxy-4-nitrophenyl thioesters demonstrating a somewhat faster reaction rate than the corresponding benzyl thioesters, which in turn may be more reactive than the alkyl thioesters. As another example, a trityl-associated mercaptoproprionic acid leucine thioester-generating resin can be utilized for constructing C-terminal thioesters (Hackeng et al., supra). C-terminal thioester synthesis also can be accomplished using a 3-carboxypropanesulfonamide safety-catch linker by activation with diazomethane or iodoacetonitrile followed by displacement with a suitable thiol (Ingenito et al., supra; Bertozzi et al.).

Ligation of the N-substituted 2 or 3 carbon chain alkyl or aryl thiol components of the invention with the first carboxythioester component generates a ligation product having an N-substituted amide bond at the ligation site. The ligation conditions of the reaction are chosen to maintain the selective reactivity of the thioester with the N-substituted 2 or 3 carbon chain alkyl or aryl thiol moiety. In a preferred embodiment, the ligation reaction is carried out in a buffer solution having pH 6–8, with the preferred pH range being 6.5–7.5. The buffer solution may be aqueous, organic or a mixture thereof. The ligation reaction also may include one or more catalysts and/or one or more reducing agents, lipids, detergents, other denaturants or solubilizing reagents and the like. Examples of preferred catalysts are thiol and phosphine containing moieties, such as thiophenol, benzylmercaptan, TCEP and alkyl phosphines. Examples of denaturing and/or solubilizing agents include guanidinium, urea in water or organic solvents such as TFE, HFIP, DMF, NMP, acetonitrile admixed with water, or with guanidinium and urea in water. The temperature also may be utilized to regulate the rate of the ligation reaction, which is usually between 5° C. and 55° C., with the preferred temperature being between 15° C. and 40° C. As an example, the ligation reactions proceed well in a reaction system having 2% thiophenol in 6M guanidinium at a pH between 6.8 and 7.8.

For the N-substituted 2 carbon chain alkyl or aryl thiols, the ligation event results from a thiol exchange that occurs between the COSR thioester component and the amino alkyl thiol component. The exchange generates a thioester-linked intermediate ligation product that after spontaneous rearrangement through a 5-membered ring intermediate generates a first ligation product of the formula J1-HN—CH(Z1)-C(O)—Nα(C1(R1)-C2-SH)—CH(Z2)-J2 having a removable N-substituted 2 carbon chain alkyl or aryl thiol [HS—C2-C1(R1)-] at the ligation site, where the substituents are as defined above. The N-substituted 2 carbon chain alkyl or aryl thiol [HS—C2-C1(R1)-] at the ligation site is amenable to being removed, under peptide-compatible conditions, to generate a final ligation product of the formula J1-HN—CH(Z1)-CO—NH—CH(Z2)-CO-J2 having a native amide bond at the ligation site.

For the N-substituted 3 carbon chain aryl or alkyl thiols, the thiol exchange between the COSR thioester component and the amino alkyl thiol component generates a thioester-linked intermediate ligation product that after spontaneous rearrangement through a 6-membered ring intermediate generates a first ligation product of the formula J1-HN—CH(Z1)-C(O)—Nα(C1-C2(R2)-C3(R3)-SH)—CH(Z2)-J2 having a removable N-substituted 3 carbon chain alkyl or aryl thiol [HS—C3(R3)-C2(R2)-C1(R1)-] at the ligation site. The N-substituted 3 carbon chain aryl thiol [HS—C3(R3)-C2(R2)-C1(R1)-] at the ligation site is amenable to being removed, under peptide-compatible conditions, to generate a final ligation product of the formula J1-HN—CH(Z1)-CO—NH—CH(Z2)-CO-J2 having a native amide bond at the ligation site.

Removal of the N-substituted alkyl or aryl thiol group is preferably performed in acidic conditions to facilitate cleavage of the N—C1 bond, yielding a stabilized, unsubstituted amide bond at the ligation site. By "peptide-compatible cleavage conditions" is intended physical-chemical conditions compatible with peptides and suitable for cleavage of the alkyl or aryl thiol moiety from the ligation product. Peptide-compatible cleavage conditions in general are selected depending on the α-substituted compound employed, which can be readily deduced through routine and well known approaches (See, e.g., "Protecting Groups in Organic Synthesis", 3rd Edition, T. W. Greene and P. G. M. Wuts, Eds., John Wiley & Sons, Inc., 1999; NovaBiochem Catalog 2000; "Synthetic Peptides, A User's Guide," G. A. Grant, Ed., W. H. Freeman & Company, New York, N.Y., 1992; "Advanced Chemtech Handbook of Combinatorial & Solid Phase Organic Chemistry," W. D.. Bennet, J. W. Christensen, L. K. Hamaker, M. L. Peterson, M. R. Rhodes, and H. H. Saneii, Eds., Advanced Chemtech, 1998; "Principles of Peptide Synthesis, 2nd ed.," M. Bodanszky, Ed., Springer-Verlag, 1993; "The Practice of Peptide Synthesis, 2nd ed.," M. Bodanszky and A. Bodanszky, Eds., Springer-Verlag, 1994; and "Protecting Groups," P. J. Kocienski, Ed., Georg Thieme Verlag, Stuttgart, Germany, 1994).

For example, where the R1, R2 or R3 substituents comprises a methoxy, hydroxyl, thiol or thiomethyl, methyl and the like, the more universal method for removal involves acidic cleavage conditions typical for peptide synthesis chemistries. This includes cleavage of the N—C1 bond under strong acidic conditions or water-acidic conditions, with or without reducing reagents and/or scavenger systems (e.g., acid such as anhydrous hydrogen fluoride (HF), triflouroacetic acid (TFA), or trimethylsulfonyl flouroacetic acid (TMSFA) and the like). More specific acidic cleavage systems can be chosen to optimize cleavage of the Nα-C1 bond to remove the aryl or alkyl thiol moiety for a given construct. Such conditions are well known and compatible with maintaining the integrity of peptides. A thiol scavenger may be included, particularly where tryptophans are present in a peptide or polypeptide sequence to avoid reaction of the tryptophan side chain with the liberated aryl or alkyl thiol moiety. Examples of thiol scavengers include ethanediol, cysteine, beta-mercaptoethanol and thiocresol.

Other specialized cleavage conditions include light or reductive-cleavage conditions when the picolyl group is the substituent. As an example, when the R1, or R2 and R3 substituents comprise a picolyl moiety, photolysis (e.g., ultraviolet light), zinc/acetic acid or electrolytic reduction may be used for cleavage following standard protocols. Where R1 of the N-substituted 2 carbon chain thiol comprises a thiomethane at R1, the mercury or HF cleavages can be used. The cleavage system also can be used for simultaneous cleavage from a solid support and/or as a deprotection reagent when the first or second ligation components comprise other protecting groups.

In one embodiment of the present invention Nα-substituted 2 or 3 chain alkyl or aryl thiols are employed in the peptide synthesis step (particularly in automated peptide synthesis and orthogonal and convergent ligation strategies) to yield properly N-terminally derivatized polypeptides that can be used as substrates for extended chemical ligation to yield synthetic bioactive proteins. Such compounds comprise a fully protected, partially protected or fully unprotected acid stable Nα-substituted 2 or 3 carbon chain amino alkyl or aryl thiol of the formula (PG1)S—C2–C1(R1)-Nα(PG2)-CH(Z2)-C(O)-J2 or (PG1)S—C3 (R3)-C2(R2)-C1 (R1)-Nα(PG2)-CH(Z2)-C(O)-J2, which are depicted below in Table IV and Table V. In particular, one or more of R1, R2 and R3 comprises an electron donating group conjugated to C1 that, following conversion of the Nα-substituted amino alkyl or aryl thiol to an Nα-substituted amide alkyl or aryl thiol, is capable of forming a resonance stabilized cation at C1 that facilitates cleavage of the Nα-C1 bond under peptide compatible cleavage conditions. PG1 and PG2 are protecting groups that are present individually or in combination or are absent and can be the same or different, where Z2 is any chemical moiety compatible with chemical peptide synthesis or extended native chemical ligation, and where J2 is any chemical moiety compatible with chemical peptide synthesis or extended native chemical ligation. PG1 (or X1) is a group for protecting the amine. PG2 (or X2) is a group for protecting the thiol. Many such protecting groups are known and suitable for this purpose (See, e.g., "Protecting Groups in Organic Synthesis", 3rd Edition, T. W. Greene and P. G. M. Wuts, Eds., John Wiley & Sons, Inc., 1999; NovaBiochem Catalog 2000; "Synthetic Peptides, A User's Guide," G. A. Grant, Ed., W. H. Freeman & Company, New York, N.Y.,1992; "Advanced Chemtech Handbook of Combinatorial & Solid Phase Organic Chemistry," W. D.. Bennet, J. W. Christensen, L. K. Hamaker, M. L. Peterson, M. R. Rhodes, and H. H. Saneii, Eds., Advanced Chemtech, 1998; "Principles of Peptide Synthesis, 2nd ed.," M. Bodanszky, Ed., Springer-Verlag, 1993; "The Practice of Peptide Synthesis, 2nd ed.," M. Bodanszky and A. Bodanszky, Eds., Springer-Verlag, 1994; and "Protecting Groups," P. J. Kocienski, Ed., Georg Thieme Verlag, Stuttgart, Germany, 1994).

TABLE IV

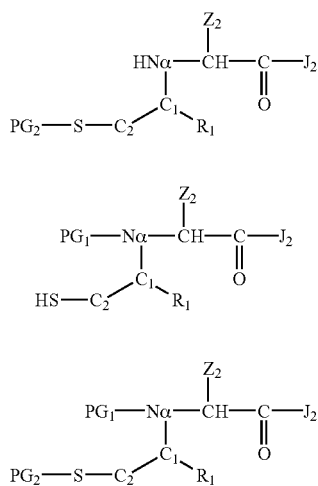

Examples of preferred protecting groups for PG1 and X1 include, but are not limited to [Boc(t-Butylcarbamate), Troc (2,2,2,-Trichloroethylcarbamate), Fmoc(9-Fluorenylmethylcarbamate), Br-Z or Cl-Z(Br- or Cl-Benzylcarbamate), Dde (4,4,-dimethyl-2,6-dioxocycloexl-ylidene), MsZ(4-Methylsulfinylbenzylcarbamate), Msc (2-Methylsulfoethylcarbamate) Nsc(4-nitrophenylethylsulfonyl-ethyloxy-carbonyl]. Preferred PG1 and X1 protecting groups are selected from "Protective Groups in Organic Synthesis," Green and Wuts, Third Edition,Wiley-Interscience, (1999) with the most preferred being Fmoc and Nsc. Examples of preferred protecting groups for PG2 include, but are not limited to [Acm(acetamidomethyl), MeoBzl or Mob(p-Methoxybenzyl), Meb(p-Methylbenzyl), Trt(Trityl),Xan(Xanthenyl),tButhio(s-t-butyl),Mmt(p-Methoxytrityl),2 or 4 Picolyl(2 or 4 pyridyl)),Fm(9-Fluorenylmethyl),tbut(t-Butyl),Tacam(Trimethylacetamidomethyl)]. Preferred protecting groups PG2 and X2 are selected from "Protective Groups in Organic Synthesis," Green and Wuts, Third Edition,Wiley-Interscience, (1999), with the most preferred being Acm, Mob, MeB, Picolyl.

TABLE V

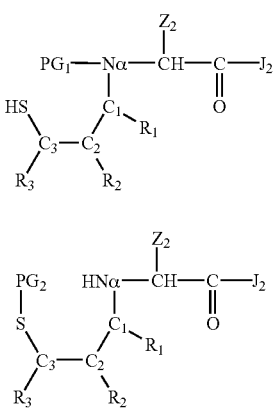

TABLE V-continued

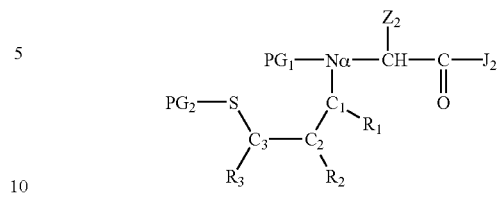

The protected forms of the Nα-substituted 2 or 3 chain alkyl or aryl thiols of the invention can be prepared as in Schemes I and II above.

The compounds of the present invention may be produced by any of a variety of means, including halogen-mediated amino alkylation, reductive amination, and by the preparation of Nα-protected, N-alkylated, S-protected, amino alkyl- or aryl-thiol amino acid precursors compatible with solid phase amino acid synthesis methods. When desirable, resolution of the racemates or diastereomers produced to give compounds of acceptable chiral purity can be called out by standard methods.

II. The Bioactive Peptides and Proteins of the Present Invention

A. Synthetic Bioactive Proteins

The above-described methods can be used to synthesize synthetic bioactive peptides and proteins. As used herein, a bioactive protein is said to be "synthetic" if non-recombinant technology has been employed to polymerize some, and most preferably all, of its amino acid residues. The term "non-recombinant technology" is intended to distinguish technologies that involve organic chemistry and other synthetic polymerization approaches from technologies involving the translation of RNA into protein, either in vivo or in vitro. Most preferably, the synthetic bioactive proteins of the present invention will be produced in vitro using the principles of organic chemistry, and in particular the methods of "native chemical ligation" and "extended native chemical ligation," as discussed herein. Such chemical synthesis will preferably be conducted using a convergent synthetic approach in which polypeptide fragments will be synthesized and then ligated to one another to form the synthetic bioactive protein. Alternatively, the synthetic bioactive proteins of the present invention may be synthesized in a single non-convergent synthesis.

As indicated above, the synthetic bioactive proteins of the present invention has substantial molecular weight, preferably being greater than about 25 kDa. For the purposes of the present invention, such determinations of molecular weight are to be made by denaturing SDS polyacrylamide electrophoresis. The term "monomer molecular weight" is intended to refer to the molecular weight of a monomer synthetic protein, as distinguished from synthetic proteins that may possess multiple copies of a protein or polypeptide.

As used herein, a synthetic protein is said to have "biological activity" if it possesses a discernible bioactivity that is dependent upon the synthetic protein's structure or amino acid sequence, such the variation in such structure or sequence enhances, modifies, or attenuates the protein's bioactivity. Without limitation, such "biological activity" includes the capacity of the protein to mediate a catalytic, signaling or inducing reaction. As used herein, a protein is said to "mediate a catalytic reaction" by converting a substrate into a product without itself being consumed or permanently modified. A protein is said to "mediate a signaling or inducing reaction" if its presence causes an organism, or its tissues or cells, to initiate, continue, enhance, modify, or attenuate gene expression, cellular differentiation, or cellular proliferation. Examples on such signaling or inducing reactions include inducing cytokine expression or a response to cytokine expression, inducing erythropoiesis, inducing or attenuating inflammation and/or an inflammatory process, initiating angiogenesis or vascularization, inducing apoptosis, affecting the cell cycle, etc.

The bioactivity of the synthetic bioactive proteins of the present invention also includes the capacity of the protein to bind specifically to a receptor, ligand or antibody. As used herein, the term "specific" binding is intended to refer to a structurally-based binding interaction, such as that existing between a hormone and its receptor, or an antibody and an antigenic epitope, as distinguished from "non-specific" binding based upon charge, solubility, hydrophobicity, etc.

The synthetic bioactive proteins of the present invention are preferably synthesized by the condensation of amino acid residues. Such amino acid residues may be the nucleic acid encoded, ribosomally installed amino acids: alanine, arginine, asparagine, aspartate, cysteine, glutamate, glutamine, glycine, histidine, isoleucine, leucine,, lysine, methionine, phenylalanine, proline, serine, threonine, tryptophan, tyrosine and valine. In one embodiment, the amino acid sequence selected for a particular desired synthetic bioactive protein would be the native, or natural sequence of that protein. In an alternative embodiment, the selected amino acid sequence will be composed of, all constructed from polypeptide fragments that may contain an N-terminal cysteine residue in place of the amino acid residues present in the native or natural sequence of that protein. The inclusion of such a residue permits the polypeptide to be ligated to another polypeptide (modified to contain a carboxy thioester group) using the principles of native chemical ligation described here and, and as such, facilitates the use of convergent synthesis to produce synthetic bioactive proteins.

In a further embodiment, the synthetic bioactive proteins of the present invention may contain "irregular" amino acid residues. As used herein, the term "irregular amino acid residues is intended to refer to amino acids that are not encoded by RNA and are not ribosomally installed. In this regard, the present invention permits wide selectability and flexibility in the design and/or construction of synthetic bioactive proteins. Examples of non-ribosomally installed amino acids that may be used in accordance with a present invention include: D-amino acids, β-amino acids, pseudo-glutamate, γ-aminobutyrate, ornithine, homocysteine, N-substituted amino acids (R. Simon et al., Proc. Natl. Acad. Sci. U.S.A. (1992) 89: 9367–71; WO 91/19735 (Bartlett et al.), U.S. Pat. No. 5,646,285 (Baindur), α-aminomethyleneoxy acetic acids (an amino acid-Gly dipeptide isostere), and α-aminooxy acids, etc. Peptide analogs containing thioamide, vinylogous amide, hydrazino, methyleneoxy, thiomethylene, phosphonamides, oxyamide, hydroxyethylene, reduced amide and substituted reduced amide isosteres and β-sulfonamide(s) may be employed.

In particular, the use of pseudo-glutamate is advantageous since the R chain modification permits attachment of polymer adducts to the synthesized protein. Likewise, N-terminal Nα-substituted 2 or 3 carbon chain alkyl or aryl thiol amino acids may be employed. Such residues (where present at the end terminus or polypeptide) can be advantageously used to ligate that polypeptide to a polypeptide having a carboxy thioester moiety, in accordance with the methods of extended native chemical ligation described herein.

In one embodiment, all of the amino acid residues of the synthetic bioactive protein may be joined together by a peptide bond (i.e., an amide bond). Alternatively, two amino acid residues (or the C-terminal and N-terminal residues of two polypeptides) may be linked to one another by a non-amide bond (such as a thioester bond, an oxime bond, a thioether bond, a directed disulfide bond, a thiozolidine bond, etc.) (Schnölzer, M. and Kent, S. B. H., Science (1992) 256:221–225; Rose, K., J. Amer. Chem Soc. (1994) 116:30–33; Englebretsen, D. R. et al., Tetrahedron Lett. 36:8871–8874; Baca, M. et al., J. Amer. Chem Soc. (1995) 117:1881–1887; Liu, C. F. et al., J. Amer. Chem Soc. (1994) 116:4149–4153; Liu, C. F. et al., J. Amer. Chem Soc. (1996) 118:307–312; Dawson, P. E. et al. (1994) Science 266: 776–779). The invention thus permits a variety of peptide bond modifications, surrogates and isosteric replacements to be exploited in the preparation of bioactive proteins.

The synthetic bioactive proteins of the present invention may be designed to possess a bioactivity that mimics a bioactivity associated with a mammalian (including human, simian, bovine, murine, porcine, ovine, equine, etc.), avian, or piscine protein. As used herein, a first protein is said to mimic a second protein if the first protein possesses a bioactivity that is modified, enhanced, or attenuated with respect to the bioactivity of the second protein. A bioactivity is said to be "associated" with the protein if its presence is directly or indirectly dependent upon the amino acid sequence of the protein.

In alternative embodiment, the bioactive proteins of the present invention may be wholly or partly engineered, without reference to any corresponding natural bioactive counterpart. Preferred synthetic bioactive proteins of the present invention include receptors, protein receptor ligands. Examples of such proteins include adrenocorticotropic hormone receptor and its bioactive fragments, angiotensin receptor, atrial natriuretic receptor, bradykininin receptor, growth hormone receptor, chemotatic receptor, dynorphin receptor, endorphin receptor, the receptor for β-lipotropin and its bioactive fragments, enkephalin receptor, enzyme inhibitor receptors, the receptor for fibronectin and its bioactive fragments, gastrointestinal- and growth hormone-releasing peptide receptors, the receptor for luteinizing hormone releasing peptide, the receptor for melanocyte stimulating hormone, neurotensin receptor, opioid receptor, oxytocin receptor, vasopressin receptor, vasotocin receptor, the receptor for parathyroid hormone and fragments, protein kinase receptor, somatostatin receptor, substance P receptor.

The synthetic bioactive proteins of the present invention they also include enzymes, and structural molecules, such as chitin or collagen, etc.

In a further embodiment, the synthetic bioactive proteins of the present invention include cytokines. Cytokines are small proteins or biological factors (in the range of 5–20 kDa) that are released by cells and mediate specific effects on cell-cell interaction, communication and on the behavior of other cells. As used herein, the term "cytokine" is intended to include the interleukins ("IL) (such as IL-1, IL-2, EL-3, L-4, IL-5, IL-6, L-7, IL-8, IL-9, IL-10, IL-11, IL-12, IL-13, IL14, etc.); lymphokines and signaling molecules such as erythropoiesis stimulating proteins (e.g., erythropoietin (EPO)), tumor necrosis factor (TNF), interferons, etc., growth factors, such as transforming growth factor, nerve growth factor, brain derived growth factor, neurotrophin-3, neurotrophin-4, heptaocyte growth factor, T-cell Growth Factor (TGF, TGF-β1, TGF-β2, TGF-β3, etc.), Colony Stimulating Factors (G-CSF, GM-CSF, M-CSF etc.), Epidermal Growth Factor (EGF, LIF, KGF, OSM, PDGF, IGF-I, etc.), Fibroblast Growth Factor (αFGF, βFGF, etc.), and hormones, particularly single peptide hormones, such as growth hormone).

Cytokines, and particularly chemotactic cytokines, also comprise particularly preferred examples of proteins whose amino acid sequence can be used to aid in the design of synthetic bioactive proteins within the ambit of the present invention. Cytokines participate in innate and acquired immune responses by either directly or indirectly mediating leukocyte recruitment, or by serving as important signals in the activation of leukocytes that have accumulated at specific sites of microbial invasion. The pro-inflammatory cytokines, interleukin-1 β(IL-1 β) and interleukin-6, (IL-6) and mediators reflect neutrophil recruitment and activation, including soluble intercellular adhesion molecule, interleukin-8 (IL-8) (Kotecha S., *European Journal of Pediatrics* (1996) 155 Suppl 2:S14–17). Interleukin-6 is a multifunctional cytokine primarily involved in the acute-phase response, B cell differentiation, and antibody production. (Akira S, et al: Interleukin-6 in biology and medicine. Adv Immunol (1993) 54:1–78). This cytokine is synthesized and secreted by many different cells, including monocytes, macrophages, T and B cells, endothelial cells, and fibroblasts. IL-6 is often induced with the proinflammatory cytokines TNFalpha and IL-1 in many alarm conditions, and circulating IL-6 plays an important role in the induction of acute phase reactions. (Xing Z, et al., J. Clin. Invest. (1998) 101(2):311–20) Cytokines that directly or indirectly influence both leukocyte recruitment and activation include TNF-alpha, granulocyte-colony-stimulating factor (G-CSF), granulocyte-macrophage-colony-stimulating factor (GM-CSF), and members of the chemokine family. Cytokines that predominantly regulate the state of leukocyte activation include interferon-gamma (IFN-gamma), interleukin-10 (IL-10), and interleukin-12 (IL-12). Cytokines can also influence microbial clearance by inducing or regulating the expression of other effector molecules, which can occur in either an autocrine or paracrine fashion.

Colony-stimulating factors are cytokines produced by a variety of myeloid and stromal cells that are required for the proliferation and maturation of hematopoietic stem cells. Additionally, studies show that these factors augment the effector cell activities of mature leukocyte populations. Specifically, G-CSF prolongs neutrophil survival in vitro, augments neutrophil phagocytic activity, and enhances neutrophil respiratory burst. (Standiford T J, et al., J. Invest. Med. (19097) 45:335–345). In contrast, GM-CSF promotes the proliferation and maturation of both neutrophils and macrophages; the activating properties of this cytokine are primarily directed toward mature macrophage populations. (Chen G H, et al, J Immunol (1994) 152:724–734).

Six closely related subfamilies of chemotactic cytokines, referred to as chemokines, have now been characterized. Of these, members of at least two subfamilies contribute to pulmonary antimicrobial host defense (Mandujano J, et al., Amer. J. Respir. Crit. Care Med. (1995) 151:1233–1238); Baggiolini M, et al., Ann. Rev. Immunol. (1997) 15:675–705). Members of the C—X—C chemokine family, which include IL-8, MIP (macrophage inflammatory protein)-2, KC, ENA-78, and NAP-2, have predominant neutrophil stimulatory and chemotactic activities, whereas the C—C family, which includes MCP (monocyte chemoattractant protein)-1, MCP-2, MCP-3, RANTES, MIP-1 alpha, and MIP-1 beta, exerts predominant chemotactic and/or activating effects on macrophages, lymphocytes, and eosinophils. (Huffnagle G B, et al., The Role Of Chemokines In Pneumonia, in Koch A, Strieter R, eds. Chemokines in Disease. Texas: R. G. Landis Co; 1996:151–168)

Interferon-gamma is a cytokine produced by T cells (both alpha beta- and gamma delta-T cells) and NK cells that is instrumental in cell-mediated immunity against a broad spectrum of pulmonary pathogens. This cytokine activates several macrophage effector cell functions, including stimulation of respiratory burst, the ability to present antigen, priming of macrophage-derived TNF release, and enhanced in vitro macrophage antimicrobial activity against bacterial, fungal, and mycobacterial organisms.

Interleukin-12 is a cytokine that promotes Th1-type immune responses, while inhibiting Th2-type immune responses. Specifically, IL-12 stimulates the development of Th1 T cells and NK cells, and increases the cytolytic activity of CD8+ cells and NK cells. Most important, IL-12 serves as the major inducer of IFN-gamma from T cells and NK cells.

In contrast to IL-12, IL-10 promotes the development of Th2-type immune responses, while inhibiting cell-mediated (Th1-type) immunity. (Howard M, et al, J. Clin. Immunol. (1992) 12:239–247). This cytokine was shown to exert potent anti-inflammatory. properties, in part by directly de-activating neutrophils and macrophages, and by down-regulating the expression of TNF, IFN-gamma, and members of both the C—X—C and C—C chemokine families. IL-10 is instrumental in attenuating undesired production of proinflammatory cytokines in states of systemic immune cell activation.

EPO is a particularly preferred example of a protein whose amino acid sequence can be used to aid in the design of a synthetic bioactive protein having erythropoieis-stimulating activity. EPO is the principal factor responsible for the regulation of red blood cell production during steady-state conditions and for accelerating recovery of red blood cell mass following hemorrhage (Jelkmann, W. (1992) Physiol. Reviews 72:449; Krantz, S. B. (1991) Blood 77:419; Porter, D. L. and M. A. Goldberg (1993) Exp. Hematol. 21:399; Nissenson, A. R. (1994) Blood Purif. 12:6). The circulating form of human EPO is a 165 amino acid (aa) glycoprotein with a molecular weight of approximately 30,000 (Sawyer, S. T. et al. (1994) Hematol. Oncol. Clinics NA 8:895; Jacobs, K. J. et al. Nature (1985) 313:806; Lin, F-K. et al. Proc. Natl. Acad. Sci. USA (1985) 82:7580). Although the cDNA for EPO predicts a molecule with 166 amino acid residues, the carboxy-terminal arginine is removed in a post-translational modification (12). There are three potential sites for N-linked glycosylation and all are filled. One O-linked carbohydrate moiety is also present (13). The effects of glycosylation are complex. Although unglycosylated *E. coli*-derived EPO shows full biological activity in vitro, glycosylation is apparently necessary for full activity in vivo. Thus, *E. coli*-produced and deglycosylated, naturally derived EPO show very low activity in animal studies (Krantz, S. B. (1991) Blood 77:419; Sasaki, H. et al. (1987) J. Biol. Chem. 262:12059; Lowy, P. H. et al. (1960) Nature 185:102; Wojchowski, D. M. et al. Biochem. Biophys. Acta 910:224; Dordal, M. S. et al. (1985) Endocrinology 116: 2293), Consistent with the above, variable glycosylation patterns show variable effects. For example, desialyated EPO exhibits both enhanced in vitro and decreased in vivo activity, an effect attributed to the exposure of galactose residues which are recognized, bound, and cleared by hepatocytes (Spivak, J. L. and B. B. Hogans (1989) Blood 73v:90; Goldwasser, E. et al. (1974) J. Biol. Chem. 249:4202). The branching pattern of fully sialyated EPO also makes a difference in biological activity. Predominantly tetra-antennary branched EPO shows activity equivalent to "standard" EPO, while predominantly bi-anternnary branched EPO shows three-fold more activity in vitro but only 15% of normal activity in vivo (Takeuchi, M. et al. (1989) Proc. Natl. Acad. Sci. USA 86:7819). Studies have indicated that only N-linked, and not O-linked sugars, are important in EPO functioning (Higuchi, M. et al. (1992) J. Biol. Chem. 267:770319).

Colony-stimulating factors and RANTES also comprise particularly preferred examples of proteins whose amino acid sequence can be used to aid in the design of a synthetic bioactive protein within the ambit of the present invention.

B. Polymer-Modified Proteins and Polypeptides

A second attribute of the present invention concerns the ability to modify a protein or polypeptide to contain one or more structurally defined polymer adducts at preselected positions. Although polymer-modified proteins have been previously described, the nature and manner of the possible polymer-modifications of the present invention markedly differ from such prior efforts.

Since the synthetic bioactive proteins of the present invention are chemically synthesized, in whole or part, it is possible to synthesize such proteins in a manner that will permit one to covalently bond polymers (such as polymers or sugar, polyethylene glycol, glycols, hyaluronic acid, etc.) to one or more particular, user-selected and user-defined sites in a polypeptide a protein backbone. Moreover, the synthetic production of the proteins in the present invention permits one to ensure that such modifications are present at each of the user-selected and user-defined sites of every molecule in a preparation. Such uniformity and control of synthesis markedly distinguishes the present invention from the random modifications permitted to the use of the methods of the prior art. Significantly, the present invention permits one to design a synthetic protein in which any non-critical residue may be derivatized to contain a polymer adduct. Moreover, for each such user-selected and user-defined site, the user may define the precise linkage (amide, thioester, thioether, oxime, etc.) through which such adducts will be bonded to the polypeptide or protein backbone. Additionally, the particular polymer adducts desired to be present at a particular site may be varied and controlled, such that a final preparation is obtained in which every protein or polypeptide present contains precisely the same derivatized adducts at precisely the same derivatized sites. Thus, the present invention permits the formation of homogeneous preparations of polymer-modified polypeptide and proteins.

In addition to providing a means for varying the position and number of attachment sites to which polymer can be bound, the present invention permits one to vary the nature of the bound polymer. The polymer adducts that may be incorporated into any particular user-selected and user-defined site can be of any defined length. Likewise, consistent with the methods of present invention, it is possible to employ polymers of different lengths at different sites. Thus, in one embodiment, the synthetic bioactive proteins of the present invention may be either mono-modified, or poly-modified, with a polymer adduct. Where more than one polymer adducts introduced into a particular polypeptide or protein, the employ polymers may be "mono-speciated," "poly-speciated," "uniformly speciated," or to "diversely speciated in." As used herein, the term "mono-speciated" is intended to refer to a polypeptide or protein that has been modified by a single species of polymer. In contrast, the term "poly-speciated" is intended to refer to a polypeptide or protein that has been modified by more than a single polymer species. Such poly-speciated polypeptide or protein are said to be "uniformly-speciated" if, at each modified site of the polypeptide or protein, the same, single species of polymer is present. In contrast, a poly-speciated polypeptide or protein is said to be "diversely-speciated" if, the modified sites of the polypeptide or protein are modified with different species of polymer.

Moreover, it is possible to vary the extent of linearity or branchedness of the polymer adduct at each of the user-selected in user-defined sites. Thus the polymer adducts may be linear, branched, or uniformly branched. The term "uniformly branched" is intended to mean that all branches of a polymer at a particular site have the same structure and length. As we appreciate, the present invention permits one to independently vary both the length of any individual branch, as well as the structure of the polymer present at such branchpoint.

In sum, the present invention permits one to define (1) the location and (2) frequency of polymer-modified, user-selected and user-defined sites in a polypeptide or protein backbone, as well as to control the (3) length, (4) species, and (5) degree of branching present at each such site. Additionally, with respect to polypeptide and proteins having multiple polymer modifications, the present invention permits one to independently define each of the above-identified five variables for each site. Moreover, with respect to polypeptides and proteins having branched polymer modifications, the present invention permits one to independently define each of the above-identified five variables for each branchpoint. Thus, the present invention provides substantial flexibility of polymer modification C. Protein and Peptide Delivery The optionally polymer-modified synthetic bioactive polypeptides and proteins of the present invention may be employed as pharmaceutical agents to effect the treatment of diseases and conditions. Most preferably, when administered to a patient or individual in need of therapy, such synthetic bioactive polypeptides and/or proteins will be administered using a drug delivery system. The uses such a system enables a drug to be presented to the patient in a manner that makes it acceptable for them and enhances the effectiveness of the desired bioactivity. The purposes of the present invention, preferred drug delivery systems include systems capable of administering polypeptides or proteins buyout oral, nasal, or inhalation routes, or intramuscularly, subcutaneously, transdermally, intravenously, intraurally or intraocularly.

Such drug delivery systems may include formulations that provide site-specific release, or that enhance protection for the intestinal mucosa. Suitable formulations include: dry powder formulations, delivery via viral particle encapsulation, liposome encapsulation, transdermal patches, electrically aided transport (electroporation therapy) and polymer/niazone conjugation.

In a preferred embodiment, such drug delivery devices will respond to changes in the biological environment and deliver—or cease to deliver—drugs based on these changes. A range of materials have been employed to control the release of drugs and other active agents.: poly(urethanes), poly(siloxanes), poly(methyl methacrylate), poly(vinyl alcohol) for hydrophilicity and strength, poly(ethylene), poly(vinyl pyrrolidone), poly(2-hydroxy ethyl methacrylate), poly(n-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), etc. In a further preferred embodiment, biodegradeable polymers will be employed to facilitate drug delivery. Such polymers include polylactides (PLA), polyglycolides (PGA), poly(lactide-co-glycolides) (PLGA), polyanhydrides, and polyorthoesters. Drug delivery devices, and methods for their use are described in U.S. Pat. Nos.; 6,072,041; 6,041,253; 6,018,678; 6,017,318; 6,002,961; 5,879,712; 5,849,331; 5,792,451; 5,783,212; 5,766,633; 5,759,566; 5,690,954; 5,681,811; 5,654,000; 5,641,511; 5,438,040; 4,810,499; and 4,659,558.

III. The Production of Synthetic Bioactive Proteins

Figure 2:
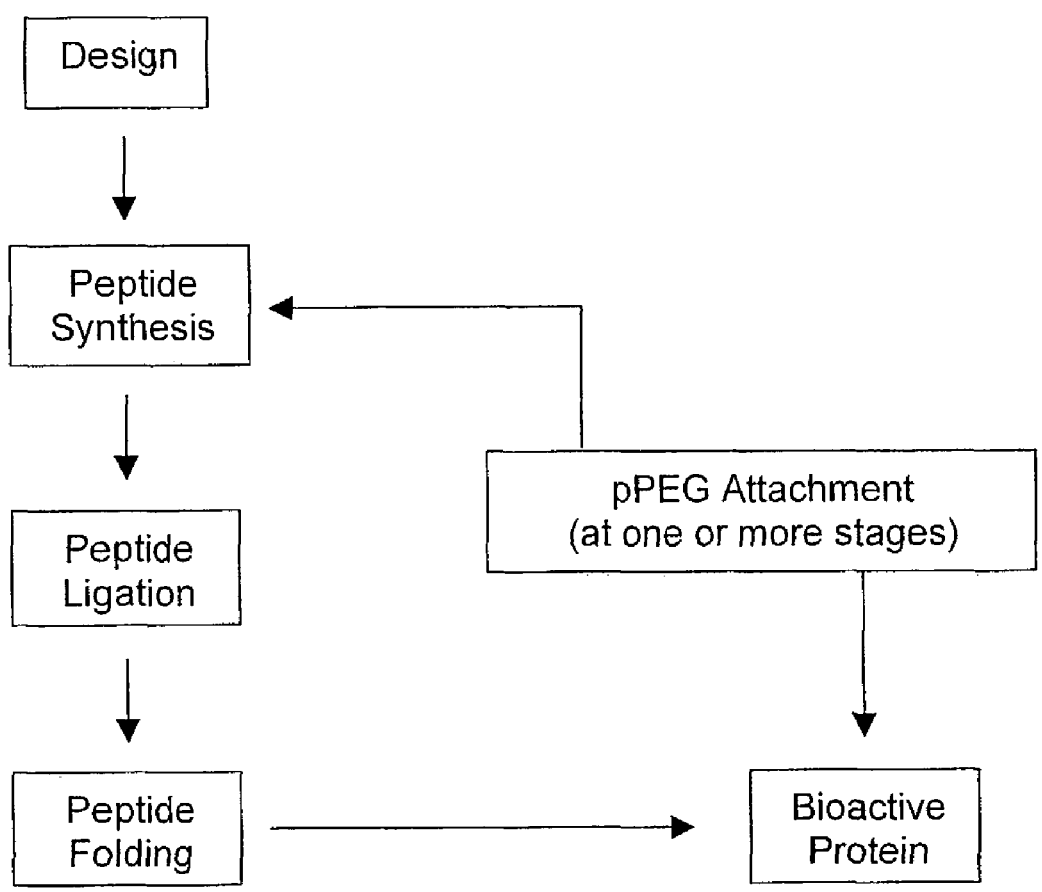
FIG. 2 illustrates the overall process of preparing the synthetic bioactive proteins of the present invention.

The production of the synthetic bioactive proteins of the present invention can be envisioned as having the following steps or components: design, synthesis, peptide ligation, protein folding, assessment of bioactivity, polymer modification of the polypeptide backbone (FIG. 2).

A. The Design of Preferred Synthetic Bioactive Proteins

In a particularly preferred embodiment, the synthetic bioactive proteins of the a present invention will be an erythropoiesis stimulating protein. As used herein, an erythropoiesis stimulating protein is a protein that mediates the production of red blood cells. The erythropoiesis stimulating bioactivity of a protein may be determined by any of a variety of means, such as by following erythropoiesis after in vivo administration, by assaying the capacity of the protein to mediate the proliferation of EPO-dependent cell lines, etc.

A preferred erythropoiesis stimulating protein is mammalian, most preferably human, EPO and its analogs. Erythropoietin is predominantly synthesized and secreted by tubular and juxtatubular capillary endothelial and interstitial cells of the kidney. Chronical kidney disease causes the destruction of EPO-producing cells in the kidney. The resulting lack of EPO frequently induces anemias. The main clinical use of EPO is therefore the treatment of patients with severe kidney insufficiency (hematocrit below 0.3) who usually also receive transfusions as well as the treatment of anemic patients following chemotherapy. Typically, EPO is synthesized recombinantly in hamster ovary cells for clinical use. EPO is a relative heat- and pH-stable acidic (pI=4.5) protein of 165 amino acid residues in its mature form. EPO conveys its activity through the EPO-receptor. Approximately 40 percent of the molecular mass of EPO is due to its glycosylation. Glycosylation is an important factor determining the pharmacokinetic behavior of EPO in vivo. Non-glycosylated EPO has an extremely short biological half-life. It still binds to its receptor and may even have a higher specific activity in vitro. However, recent experiments have shown that PEGylation of EPO significantly enhances its lifetime, but to significantly decrease EPO activity in a cell-based assay system.

The synthetic erythropoiesis stimulating proteins ("SEPs") of the present invention are preferably chemically modified synthetic analogs of human urinary EPO. In a preferred embodiment, they contain one or more polymer moieties (most preferably pPEG moieties) attached to one or more peptide residue(s) through a thioether, oxime, amide or other linkage. In a highly preferred embodiment, such linkages will be at one or more of the positions that are naturally glycosylated in human urinary EPO (i.e., positions 24, 38, 83 and 126). Most preferably, the SEP molecules will have pPEG moieties at two or more of such positions. In an alternative embodiment, other protein residues may be modified by polymer moieties. The positions of modification for the synthetic bioactive proteins of the present invention include residues located in a disordered loop, region or domain of the protein, or at or near sites of potential protease cleavage. For example, polymer modifications may be introduced at one or more positions of 9, 69 and/or 125 of EPO. The total molecular weight of the SEP molecules of the present invention may vary from about 25 to about 150 kDa, and more preferably from about 30 to about 80 kDa. The molecular weight can be controlled by increasing or decreasing the number and structure of the polymer (such as pPEG) utilized for modification of a given analog. The pPEG mediated hydrodynamic MW for the larger constructs is greater than about 100 kDa. In vitro assays in cells expressing the human EPO receptor indicate that SEPs of the present invention have an ED50 that is equivalent to that of recombinantly produced glycosylated human EPO.

Figure 3:
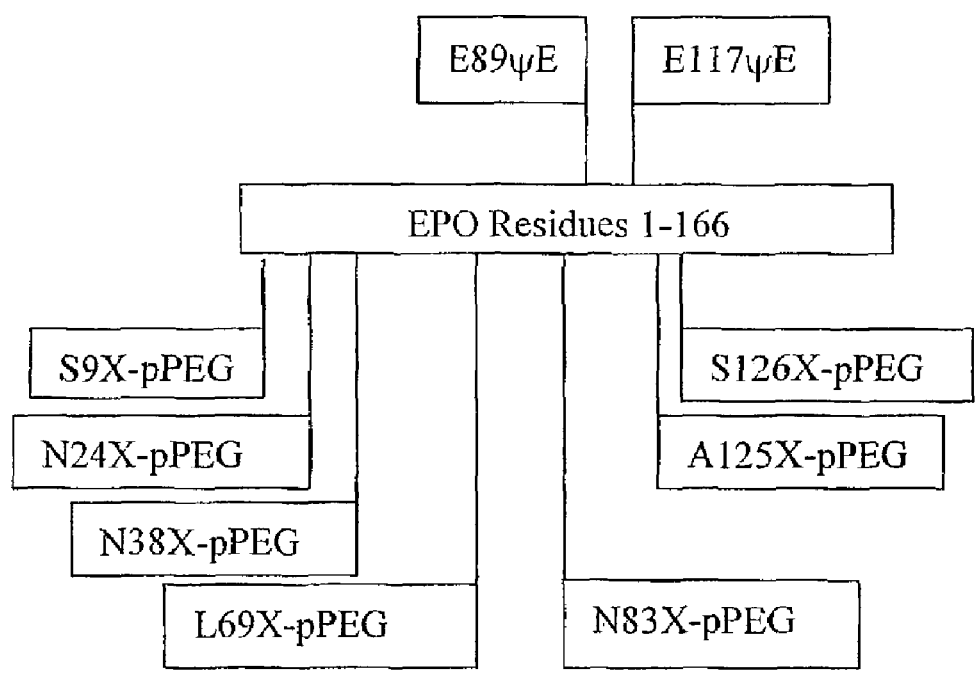
FIG. 3 depicts the basic structure of a preferred type of synthetic erythropoiesis stimulating proteins.

Oxime-linked pPEG analogs are preferably constructed by attaching an aminooxy, ketone or aldehyde functionalized pPEG to the SEP protein at a non-naturally encoded amino acid bearing a side chain aminooxy, ketone or aldehyde functionality. For example, positions 89 and 117 of SEP-0 and 1 contain pseudo glutamates (a non-naturally encoded amino acid bearing a side chain of the formula —CH$\alpha$-CH$_2$—S—COOH (as compared to glutamate side chain —CH$\alpha$-CH$_2$—CH$_2$—COOH)). SEP analogs utilizing thioether linkages are preferably constructed to contain a thiol functionality provided by a cysteine or unnatural amino acid with a side chain bearing the thiol. FIG. 3 depicts the basic structure of one type of preferred synthetic erythropoiesis stimulating proteins.

In an alternative embodiment, the SEP molecules of the present invention may comprise "circularly permuted" EPO analogs in which the natural amino and carboxy terminus of EPO have been relocated. Most preferably, such relocation will move the amino and carboxy termini to positions of low structural constraint, such as to disordered loops, etc. The disordered loop around positions 125 and 126 (relative to the native EPO residue numbering system) is an example of such a relocation site. Most preferably, such SEPs will be disulfide free, and will be chemically modified to contain polymer moieties at preselected residues.

Alternatively, the SEP molecules may have amino and carboxy termini relocated to a naturally occurring glycosylation site, or to other sites amenable to glycosylation, such as position 126 and 125. The SEP molecules may also include modifications of the amino and carboxy termini to eliminate or modify charge (such as by carboxy amidation, etc.).

Figure 4:
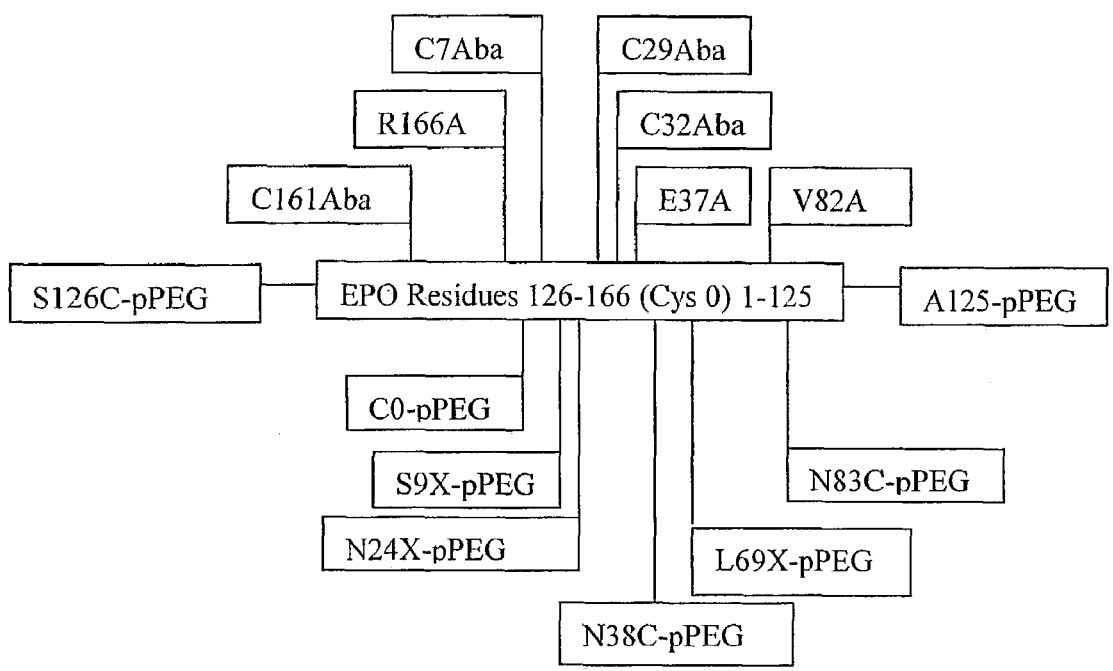
FIG. 4 shows the general structure of circularly permuted SEP analogs having no free amino or carboxy terminus. The pPEG ("precision PEG" as described herein) attachment sites are positionally the same relative to the SEP analogs. The SEP analogs are circularized by an oxime linkage between the new N-/C-terminal positions, such as P126C and A125X. The total molecular weight of the SEP analogs will range from about 50–80 kDa, depending on the pPEG utilized for modification of a given analog, with the pPEG mediated hydrodynamic MW estimated to be greater than about 100 kDa.

In a preferred example of such circularly permuted molecules, new N- and C-termini are provided by positions 126 and 125, respectively. The natural disulfide-forming cysteines at positions 7, 29, 32 and 161 are preferably replaced by the non-naturally encoded amino acid, L-$\alpha$-N-butyric acid (Aba), which cannot form disulfide bridges. Residues R166, E37 and V82 are preferably replaced with alanines to improve production. Also, an additional cysteine is preferably inserted between positions 1 and 166 relative to the native EPO number scheme, which is numbered below as '0'. The resulting molecule contains four cysteines (at positions 126, 0, 38, and 83 (as read in the N- to C-terminal direction)), which are utilized as (1) ligation sites and (2) thioether-forming pPEG attachment sites. Optionally, a cysteine may replace A125 to provide an additional pPEG attachment site. The total molecular weight of such SEP molecules of the present invention may vary from about 25 to about 150 kDa, and more preferably from about 30 to about 80 kDa. The molecular weight can be controlled by increasing or decreasing the number and structure of the polymer (such as pPEG) utilized for modification of a given analog. The pPEG mediated hydrodynamic MW for the larger constructs is greater than 100 kDa. Optional pPEG attachment sites are located at positions 125, 9, and 24 (as read in the N- to C-terminal direction). Additional SEP analog designs have alternative N- and C-termini in the disordered loop region, and/or truncate residues from the new N- and/or C-termini. The basic structure of preferred circularly permuted molecules is shown in FIG. 4.

In an alternative embodiment, the synthetic bioactive proteins of the present invention are a mammalian, most preferably human C-GSF. G-CSF induces the rapid proliferation and release of neutrophilic granulocytes to the blood stream, and thereby provides therapeutic effect in fighting infection. The human GCSF protein is 174 amino acids in length (Patent: EP 0459630 (Camble,R. et al.), and variants of its sequence have been isolated. The protein has four cysteine residues and an O-glycosylation site at threonine position 133.

In one embodiment of such a synthetic GCSF molecules, the amino acid sequence of the molecule will be altered, relative to the sequence of native GCSF, so as to contain natural, or more preferably, non-naturally encoded, hydrophobic residues at one or more of positions 1, 2 or 3. Optionally, such molecules will be further modified to contain an additional natural, or more preferably, non-naturally encoded, hydrophobic residues at position 5 of GCSF, and/or at positions 173 and/or 174.

In a further preferred embodiment the synthetic GCSF molecules will be polymer-modified (preferably pPEG) at one or more of positions 63, 64 and/or 133 and/or at one or more of positions 1 and 174. The pPEG polymers may be linear or branched, charged, uncharged, or mixed; and may have a molecular weight range of from about 5 to about 80 kDa, and more preferably, from about 40 to about 70 kDa pPEG total MW contribution depending on the number and structure of pPEGs utilized for modification. The hydrodynamic radius exhibits a larger MW effect in vivo (for example, a 10 kDa branched pPEG exhibits an effective MW of about 55 kDa). The estimated pPEG mediated hydrodynamic MW is greater than 100 kDa.

For analogs utilizing oxime linkage, the pPEG is preferably attached to non-naturally encoded residues bearing a side chain aminooxy, ketone or aldehyde functionality. For analogs utilizing thioether linkage, the pPEG is preferably attached to a cysteine or unnatural amino acid with a side chain bearing a thiol. For analogs utilizing amide linkage, the pPEG is attached to a natural or unnatural amino acid bearing a reactive side chain amine.

Figure 5:
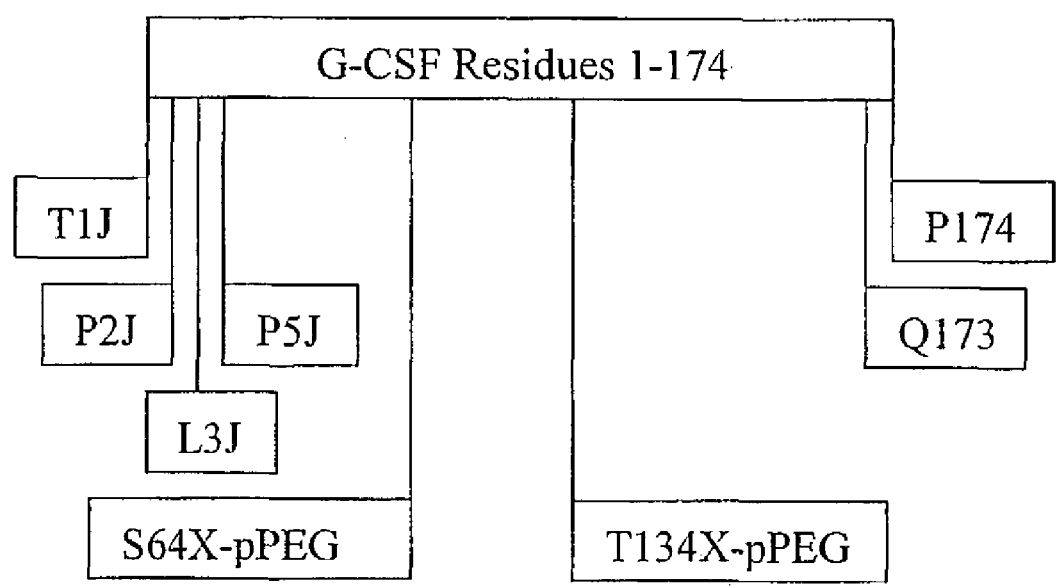
FIG. 5 shows the basic structure of synthetic bioactive GCSF proteins. In the figure, "J" designates a non-naturally encoded residue having a hydrophobic side chain.

The basic structure of the synthetic bioactive GCSF proteins is shown in FIG. 5. In the figure, "J" designates a non-naturally encoded residue having a hydrophobic side chain.

The bioactivity of such synthetic bioactive GCSF proteins may be assayed by conventional means, such as by assaying for their capacity to mediate the proliferation of a factor-dependent human or mouse cell line (e.g., NFS60 cell line), or by measuring neutrophil stimulation, half-life, and immunogenicity in vivo, either with or without a delivery system targeting >20 day half-life/release).

In an alternative embodiment, the synthetic bioactive proteins of the present invention are a mammalian, most preferably human chemokine, RANTES. RANTES blocks entry of M-tropic HIV strains through the primary receptor CCR5, and also down-modulates inflammation pathways involved in asthma, transplant rejection and wound healing (Kalinkovich A, et al., Immunol Lett. (1999) 68:281–287). The synthetic RANTES molecules of the present invention preferably differ from the RANTES chemokine in being chemically modified such that: (1) the N-terminal serine found at position 1 of RANTES 1–68 is substituted with an n-nonanoyl ("NNY") group; and (2) the tyrosine at position 3 is substituted with a non-naturally encoded amino acid having a hydrophobic side chain. Such compounds have been found to be extremely potent, possessing ED50 in the pM range, compared to the mM range for recombinant "Met-RANTES 1–68".

Potent RANTES analogs have been created having one or more additional changes to those noted above, such as replacement of the proline at position 2 with a non-naturally encoded amino acid having a hydrophobic side chain, and by the attachment of a fatty acid to the C-terminus of the molecule. Receptor specificity has been improved in combination with potency by modifications to the N-loop region corresponding to RANTES residues 12–20. In a further preferred embodiment, the synthetic RANTES molecules of the invention incorporate a polymer moiety (such as pPEG, or nonanoy ("NNY") or Y3X at their N- or C-terminus to improve inter alia in vivo half-life. The pPEG moiety is preferably attached through an oxime linkage to a non-naturally encoded amino acid that is introduced at position 66, 67, 68 or linker at position 68, with preference to position 67. The fatty acid is preferably attached through an oxime linkage (preferably through a linker) to residue 68, such as an amino-oxy modified amino acid di- or tri-peptide linker. Other attachment chemistries may alternatively be employed. The molecular weight of the larger constructs of such synthetic RANTES analogs ranges from about 25 kDa to about 45 kDa depending upon the nature and structure of the pPEG attachment, and for the larger constructs have a pPEG mediated hydrodynamic MW of greater than 60 kDa. The structure of preferred synthetic RANTES analogs is shown in FIG. 6.

B. Defined and Specific Polymer Modification of the Synthetic Bioactive Proteins and Peptides A further aspect of the present invention relates to chemical moieties and polymers, in particular water-soluble polymers, and their use to modify proteins so as to yield protein drugs with improved properties relative to the unmodified protein. The anticipated beneficial effects of such modification include but are not limited to (a) improved potency (b) longer lifetime of the protein drug in the circulation due to increased proteolytic stability and reduced clearance rates (c) reduced immunogenicity and (d) possibly differential targeting compared to the unmodified molecule.

As discussed above, although polyethylene glycol has been employed to modify proteins (see, for example, U.S. Pat. No. 6,027,720, Kuga et al., which relates to the modification of lysine residues of G-CSF to permit the attachment of polyethylene glycol molecules via reactive amine groups), such modifications are associated with molecular heterogeneity, and molecular diversity.

As used herein, the term "molecular heterogeneity" is intended to refer to a variation in the number of polymer molecules attached to each protein of a protein preparation. The term "molecular diversity" is intended to refer to (a) a variation in the site(s) of the protein that are modified by the polymer, (b) a variation in the length of the polymer adducts of different sites of the same protein, or of the same site(s) in different proteins of a protein preparation, or (c) a variation in the extent and/or nature of any branching of the polymer adducts of different sites of the same protein, or of the same site(s) in different proteins of a protein preparation. As used herein, the term "molecularly homogeneous" is intended to refer to a preparation of a protein in which all of the protein molecules contain the amino acid sequence and the same polymer modifications at the same positions. A mixture of two or more "molecularly homogeneous" protein preparations is referred to herein as a "molecularly defined" preparation.

In accordance with this aspect of the invention, a solution to the above-identified problems of polymer heterogeneity, diversity, and unsuitability involves the production of a new class of biocompatible polymers which combine the advantages of both polypeptides (precise length, convenient synthesis) and "pPEG" ("precision PEG"), a flexible, amphiphilic, non-immunogenic, polymer not susceptible to proteases) Rose, K. et al. (U.S. patent application Ser. No. 09/379,297, herein incorporated by reference). This new class of biocompatible polymer has the formula:

—[CO—X—CO—NH—Y—NH]$_n$— n is an integer, preferably from 1–100 and more preferably from 2–100, where X and Y are biocompatible repeat elements of precise structure linked by an amide bond. Preferably, X and Y will be divalent organic radicals lacking reactive functional groups or are absent and are the same or different, and can vary independently with each repeating unit (n). Preferably, when n=2, at least one of X or Y will be selected from the group consisting of a substituted, unsubstituted, branched and linear aliphatic and aromatic group. More preferably, at least one of X or Y the divalent organic radicals will be selected from the group consisting of phenyl, a $C_1$–$C_{10}$ alkylene moiety, a $C_1$–$C_{10}$ alkyl group, a heteroatom-containing phenyl, a heteroatom-containing $C_1$–$C_{10}$ alkylene moiety, a heteroatom-containing $C_1$–$C_{10}$ alkyl group, and a combination thereof.

Particularly preferred pPEG moieties have the formulae:

—{CO—(CH$_2$)$_2$—CO—NH—(CH$_2$)$_3$—(OCH$_2$CH$_2$)$_3$—CH$_2$—NH}$_n$— where n preferably varies from 1–100 and more preferably from 2–100; or

—{—CO—(CH$_2$)$_2$—CO—NH—(CH$_2$)$_6$—NH—CO—(CH$_2$)$_2$—CO—NH—(CH$_2$)$_3$—(OCH$_2$CH$_2$)$_3$—CH$_2$—NH—}$_n$—, where n preferably varies from 1–50 and more preferably from 2–50.

Such pPEG moieties can be synthesized in any of a variety of ways. Such moieties are, however, preferably produced using a solid phase stepwise chain assembly of units, rather than a polymerization process. The use of such an assembly process permits the moieties of a preparation to have a defined and homogeneous structure, as to their length, the nature of their X and Y substituents, the position(s) (if any) of branch points, and the length, X and Y substituents, and position(s) of any branches.

Preferably, such moieties will be synthesized by steps such as:
(a) acylating the amino or hydroxyl group of a compound of the formula Z—Q-support with a molar excess of a derivative of a diacid having the formula, HOOC—X—COOH, where Z is H$_2$N— or HO—; Q is a linker or a target molecule; and the support is a solid phase, matrix or surface;
(b) activating the free carboxyl group of the product of step(a);
(c) aminolysing the product of step (b) with a molar excess of a diamine having the formula, NH$_2$—Y—NH$_2$; and
(d) optionally repeating steps (a)–(c) using HOOC—X—COOH and NH2-Y—NH2, where said X and Y are divalent organic radicals or are absent and are the same or different, and can vary independently with each of said optionally repeated units, and are the same or different from the X and Y substituents used in any of the previous acylating and aminolysing steps.

In preferred embodiments, 6-mers, 12-mers, 18-mers and 32-mers of above repeat unit are employed. Where desired, the repeat unit can be used, for example, in conjunction with the amino group of lysine to form branched pPEG structures. The pPEG may be attached to the synthetic proteins of the present invention by a variety of chemistries, including thioether, oxime and amide linkage formation.

In one embodiment, the solid phase stepwise chain assembly of units comprises:

Step 1: Couple protected or unprotected diacid to amino on resin to generate amide bond at linkage site (where PG is a protecting group that is present or absent depending on diacid employed):

PG-OOC—X—COOH+NH$_2$—Y—NH-Resin

Step 2: Remove protecting group (PG) on resin, if present

HOOC—X—CO—NH—Y—NH-Resin

Step 3: Couple protected or unprotected diamino to carboxy on resin to generate amide bond at linkage site (where PG is present or absent depending on diamino employed)

PG-NH—Y—NH+HOOC—X—CO—NH—Y—NH-Resin

Step 4: Remove protecting group (PG) on resin, if present

—NH—Y—NH—OC—X—CO—NH—Y—NH-Resin

Step 5: Repeat steps 1–4 'n' times to add 'n' units then cleave from resin

—[CO—X—CO—NH—Y—NH]—[CO—X—CO—NH—Y—NH]—[CO—X—CO—NH—Y—NH]—[CO—X—CO—NH—Y—NH]—

As discussed, linear and branched pPEG constructs are preferred water-soluble polymers for attachment to the synthetic bioactive molecules of the invention. The pPEGs employed bear pendant groups that are charged or neutral under physiological conditions, and can be made to vary in attachment chemistry, length, branching and solubility depending on the pPEG structure one employs. As noted above, preferred pPEGs of the invention comprise a water-soluble polyamide having the repeat unit —CO—X—CO—NH—Y—NH—, where one or both of X and Y comprises a water-soluble repeat unit, and most preferably a 'PEG'-based repeat unit. Although oligoureas are in principle accessible using a simple two-step solid phase procedure, as shown below for the case of an amino resin, NH$_2$-Resin, and a symmetrical diamine, NH$_2$—Y—NH$_2$:

Activation with carbonyldiimidazole→im-CO—NH-Resin

Aminolysis with diamine NH$_2$—Y—NH$_2$→NH$_2$—Y—NH—CO—NH-Resin where these two steps may be repeated a number of times to give an oligourea with repeat unit —NH—Y—NH—CO—, this approach is less preferred. This is because the yields of the above steps may be non-quantitative at room temperature, even with very large excesses of reagents and long reaction times. Accordingly, it is preferable to use a three-step solid phase procedure, shown below for the case of an amino resin, NH$_2$-Resin, to form a polyamide. The Reagents HO$_2$C—X—CO$_2$H and NH$_2$—Y—NH$_2$ should be symmetrical in order to avoid isomeric products.

Acylation with diacid HO$_2$C—X—CO$_2$H→HO—
   CO—X—CO—NH-Resin

Activation with carbonyldiimidazole→im-CO—
   OCO—X—CO—NH-Resin

Aminolysis with diamine NH$_2$—Y—NH$_2$→NH$_2$—
   Y—NH—CO—X—CO—NH-Resin

These three steps may be repeated in sequence a number of times to give a polyamide with repeat unit —NH—Y—NH—CO—X—CO—. The polymer contains a precise number of monomer units, X and Y can be varied independently at each step, and end-groups can be chosen at will. For example, by using succinic anhydride ("Succ") for the acylation step and 4,7,10-trioxa-1,13-tridecanediamine (also referred to as "EDA" or "TTD") for the aminolysis step, 'PEG'-based polyamides are formed wherein X is —CH$_2$CH$_2$—, Y is —NH—CH$_2$CH$_2$CH$_2$—(OCH$_2$CH$_2$)$_3$—CH$_2$—NH— and the repeat unit is —NH—CH$_2$CH$_2$CH$_2$—(OCH$_2$CH$_2$)$_3$—CH$_2$—NH—COCH$_2$CH$_2$CO—. In spite of the fact that the procedure involves divalent reagents with no protecting groups, cross-linking is not a problem when standard commercial peptide synthesis resins are used (Rose et al., (U.S. patent application Ser. No. 09/379,297); and Rose et al., *J. Am. Chem. Soc.* (1999) 121:7034), except as noted below for the case of branched Lys cores for making branched constructs.

For example, branched pPEG constructs can be made in a similar manner as for the "chemobody" constructs described in Rose et al., U.S. Pat. No. 6,552,167) and Rose, K. and Vizzavona, J. (*J. Am. Chem. Soc.* (1999) 121:7034). Thus, branched pPEG constructs can be made to have a branching core such as a lysine branching core, which is coupled through oxime linkers to a preferred water-soluble polyamide such as—(COCH$_2$CH$_2$CO—NH—CH$_2$CH$_2$CH$_2$—(OCH$_2$CH$_2$)$_3$—CH$_2$—NH)$_n$—. For instance, oxime bonds can readily formed between an aminooxyacetyl group on a Lys side chain at the other extremity of the polyamide, and glyoxylyl groups on a lysine core, for example the tetrameric core (O=CHCO)$_4$Lys$_2$Lys-. Thus an oxime linker off of each lysine branch point can be prepared as the structure -Lys(COCH$_2$ON=CHCO—)amide-. An alternative construction can place the oxime bond between the polyamide and the free pendant group of the polyamide, preferably using a monoprotected diamine and deprotection after coupling the polyamide, to generate a tetravalent branched constructed depicted below.

Figure 7:
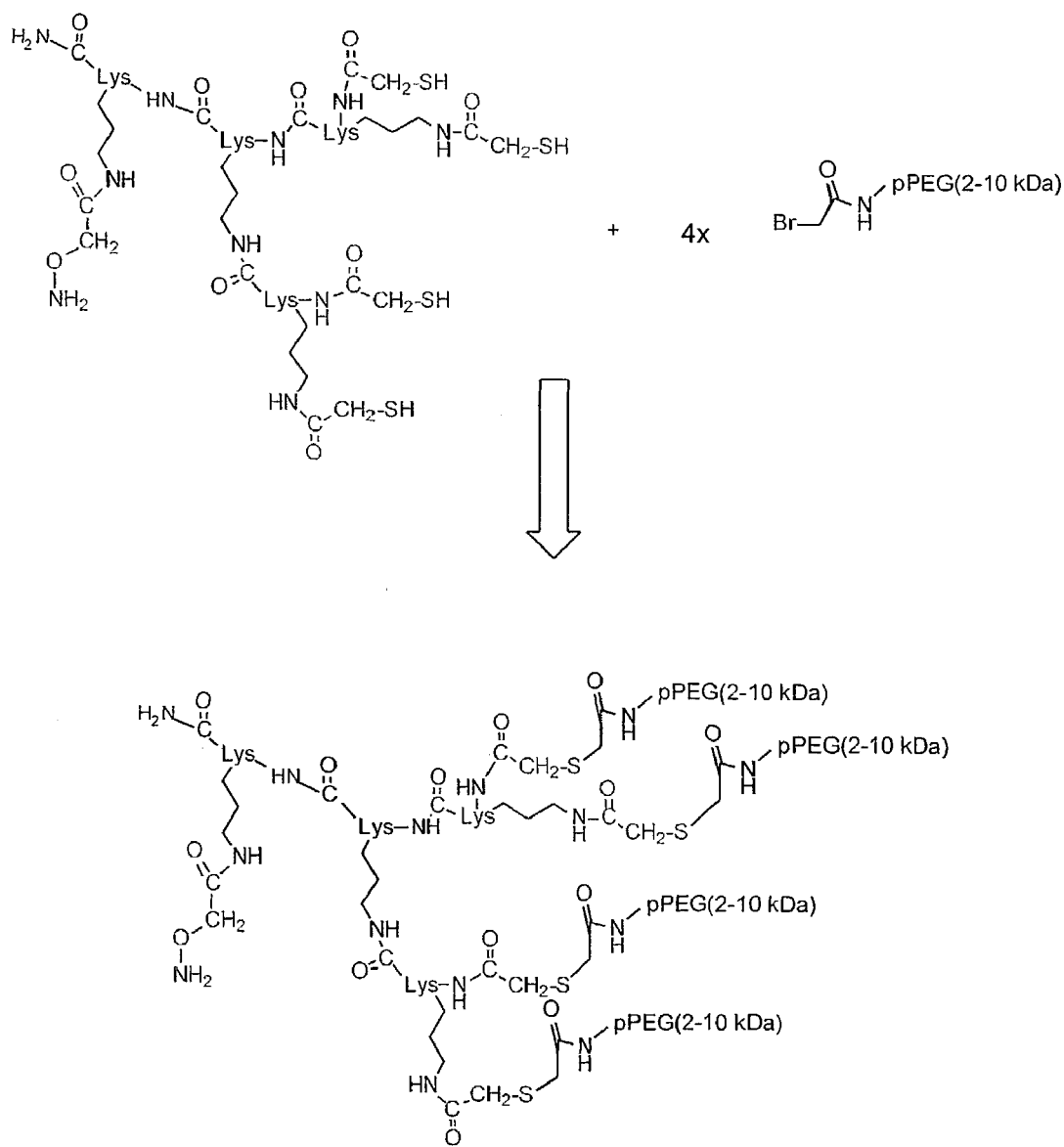
FIG. 7 depicts schematically the formation of branched-chain pPEG polymer.

Oxime chemistry can be used in making not only dimeric and tetrameric branched constructs, but it also suitable for assembling octameric branched constructs (Rose, K., J. Am. Chem. Soc. (1994) 116:30; Rose, K. et al., Bioconj. Chem. (1996) 7:552). It is, of course, possible to use other chemistries for such purposes when using such pPEG polyamides (See, e.g., FIG. 7). Moreover, polyamide formation may be incorporated into a synthetic scheme for peptide synthesis involving Boc or Fmoc chemistry, but when elaborating such schemes it must be borne in mind that the aminolysis step will remove the Fmoc group, and will remove formyl protection of indole if Boc chemistry is to be used.

Accordingly, such pPEGs can be made to have various branching cores (e.g., Lysine branching core etc.) linked through a bond of choice (e.g., amide, thioether, oxime etc.) to a linear water-soluble polyamide (e.g., -(Succ-TTD)$_n$-, etc.), where the free end of each linear water-soluble polyamide can each be capped with a desired pendant group (e.g., carboxylate, amino, amide etc.) to provide a desired charge. Moreover the linear and branched pPEGs of the present invention can be made to comprise a unique functional group for attachment to a synthetic protein bearing one or more unique and mutually reactive functional groups, and the pendant groups of the pPEGs will preferably be non-antigenic (See, e.g., FIG. 7).

All publications and patent applications mentioned in this specification are herein incorporated by reference to the same extent as if each individual publication or patent application was specifically and individually indicated to be incorporated by reference. The discussion of the background to the invention herein is included to explain the context of the invention. This is not to be taken as an admission that any of the material referred to was published, known, or part of the prior art or common general knowledge anywhere in the world as of the priority date of any of the claims. Having now generally described the invention, the same will be more readily understood through reference to the following examples, which are provided by way of illustration, and are not intended to be limiting of the present invention, unless specified.

EXAMPLE 1

Synthesis of Synthetic Erythropoiesis Stimulating Protein SEP-0

A synthetic erythropoiesis stimulating protein (SEP) was synthesized. The sequence of the full-length synthesized protein (designated "SEP-0 (1–166)" is:

```
                                               (SEQ ID NO:1)
APPRLTCDSR VLERYLLEAK EAEKITTGCA EHCSLNEKIT

VPDTKVNFYA WKRMEVGQQA VEVWQCLALL SEAVLRGQAL

LVKSSQPWψP LQLHVDKAVS GLRSLTTLLR ALGAQKψAIS

PPDAASAAPL RTITADTFRK LFRVYSNFLR GKLKLYTGEA

CRTGDR
``` where Ψ denotes a non-native amino acid residue consisting of a cysteine that is carboxymethylated at the sulfhydryl group. The SEP-0 protein was synthesized in solution from four polypeptide segments:

```
Segment SEP-0:1 (GRFN 1711; composed of residues 1–32 of SEQ ID NO:1):
APPRLICDSR VLERYLLEAK EAEKITTGCA EH-thioester Segment SEP-0:2 (GRFN 1712, composed of residues 33–88 of SEQ ID NO:1):
CSLNEKITVP DTKVNFYAWK RMEVGQQAVE VWQGLALLSE AVLRGQALLV KSSQPW-thioester
(where Cys³³ is Acm protected)

Segment SEP-0:3 (GRFN 1713, composed of residues 89–116 of SEQ ID NO:1):
```

```
                                        -continued
CPLQLHVDKA VSGLRSLTTL LRALGAQK-thioester
(where Cys⁸⁹ is Acm protected)

Segment SEP-0:4 (GRFN 1714, composed of residues 117–166 of SEQ ID NO:1):
CAISPPDAAS AAPLRTITAD TFRKLFRVYS NFLRGKLKLY TGEACRTGDR-carboxylate
(where the C-terminal cysteine (Cys¹⁶¹) carries a picolyl (pico) protecting group)
```

The peptides SEP-0:1 and SEP-0:2 and SEP-0:3 were synthesized on a thioester-generating resin by the in situ neutralization protocol for Boc (tert-butoxycarbonyl) chemistry and stepwise solid phase peptide synthesis (SPPS) using established SPPS, side-chain protection and thioester-resin strategies (Hackeng, et al., PNAS (1999) 96: 10068–10073; and Schnolzer, et al., Int. J. Pept. Prot. Res., (1992) 40: 180–193)) on an ABI433A automated peptide synthesizer or by manual chain assembly, or ordered and acquired from commercial vendors. For instance, a standard set of Boc SPPS protecting groups was used, namely: Arg(Tos); Asp(cHex); Cys(4MeBzl) & Cys(Acm); Glu (cHex); His(DNP); Lys(CIZ); Ser(Bzl); Thr(Bzl); Trp (formyl); Tyr(BrZ); Met, Asn, Gln were side-chain unprotected. Segment SEP-0:4 was synthesized analogously on a —OCH$_2$-Pam-resin. The peptides were deprotected and simultaneously cleaved from the resin support using HF/p-cresol according to standard Boc chemistry procedure; however, for those peptides containing protecting groups not removed in HF/p-cresol, the protecting groups were retained. The peptides were purified by preparative C4 reverse-phase-high pressure liquid chromatography (HPLC). Fractions containing pure peptide were identified using ES-MS (electrospray ionization mass spectrometry), pooled and lyophilized for subsequent ligation.

Step 1: Ligation #1 Segment SEP-0:3 and segment SEP-0:4 were dissolved in TFE at 15 mM concentration. Saturated phosphate buffer (pH 7.9) containing 6 M guanidinium chloride and 1% thiophenol was added, resulting in a clear solution of the peptide segments. After ligation, the ligation mix was added to a solution of 2 ml TFE (trifluoroethanol), 6 ml 6M guanidinium chloride, 100 mM phosphate containing 25% β-mercaptoethanol and incubated for 20 minutes. The solution was acidified with a solution of 15 mg/ml TCEP (tris(2-carboxyethyl)phosphine.HCl) in glacial acetic acid and loaded onto a preparative C4 reverse-phase HPLC column (1 inch diameter). The peptides were then purified by preparative gradient reverse-phase HPLC. Fractions containing the desired ligated product SEP-0:Acm+SEP-0:3+SEP-0:4 were identified by ES-MS and pooled.

Step 2: Acm-removal #1 For Acm removal, the aqueous acetonitrile solution containing the pooled fractions of SEP-0:Acm+SEP-0:3+SEP-0:4 was diluted 1× with HPLC grade water, and solid urea was added for a final concentration of 2 molar. A threefold molar excess (relative to the total expected cysteine concentration) of a 30 mg/ml Hg(acetate)$_2$ solution in 3% aqueous acetic acid was added and the solution is stirred for one hour. The solution was then made 20% in β-mercaptoethanol, loaded onto a semi-preparative reverse-phase HPLC column and purified with a step gradient. Fractions containing the desired product SEP-0:3+SEP-0:4 were identified by ES-MS and lyophilized overnight.

Step 3: Ligation #2 Equal amounts of SEP-0:3+SEP-0:4 and SEP-0:2 were jointly dissolved in neat TFE at 15 mM concentration. 250 mM Phosphate buffer (pH 7.5) containing 6 M guanidinium chloride and 1% thiophenol was added, resulting in a clear solution of the peptide segments. After one day of ligation, the ligation mix was added to a solution of 10 ml TFE, 10 ml β-mercaptoethanol, 10 ml piperidine and 20 ml 6M guanidinium chloride, pH 4, and incubated for 20 minutes to remove any remaining protecting groups. The solution was acidified with a solution of 15 mg/ml TCEP in 20% aqueous acetic acid, loaded onto a preparative reverse-phase HPLC column and purified with a linear gradient. Fractions containing the desired ligated product SEP-0:Acm+SEP-0:2+SEP-0:3+SEP-0:4 were identified by ES-MS and lyophilized overnight.

Step 4: Carboxymethylation SEP-0:Acm+SEP-0:2+SEP-0:3+SEP-0:4 was dissolved in TFE at 15 mM concentration. A two-fold excess (v/v) of 200 mM Phosphate buffer (pH 7.9) containing 6 M guanidinium chloride was added, resulting in a clear solution of the peptide segment. A 25-fold excess of bromo-acetic acid dissolved in a minimum amount of methanol was added, and the solution was allowed to react for two hours. The solution was acidified with a solution of 15 mg/ml TCEP in 20% aqueous acetic acid, loaded onto a preparative reverse-phase HPLC column and purified with a step gradient. Fractions containing the desired carboymethylated product SEP-0:Acm+SEP-0:2+SEP-0:3+SEP-0:4+Et were identified by ES-MS and pooled.

Step 5. Picolyl Removal Zinc dust was activated in 2M HCl for 30 minutes. Peptide SEP-0:Acm+SEP-0:2+SEP-0:3+SEP-0:4+ Et was dissolved in neat TFE at about 10 mg/ml concentration. The solution was diluted with 4× (v/v relative to TFE) 6M guanidinium chloride, 100 mM acetate, pH 4, containing (freshly added) 35 mg/ml L-methionine and 35 mg/ml dodecylsarcosine (i.e. sodium N-dodecanoylsarcosine). The solution was added to the activated Zn powder. The reaction was monitored at ~1 hr intervals and is complete after five hours. After completion, the supernatant was removed and the remaining Zn powder washed twice for five minutes with 6M guanidinium chloride, pH 4, 100 mM acetate containing 35 mg/ml L-methionine and 35 mg/ml dodecylsarcosine containing 20% TFE as well as once with the same solution containing 20% β-mercaptoethanol. The combined product was acidified with a solution of 15 mg/ml TCEP in 20% aqueous acetic acid, loaded onto a preparative reverse-phase HPLC column and purified with a step gradient. Fractions containing the desired modified product SEP-0:Acm+SEP-0:2+SEP-0:3+SEP-0:4+Et-Pico were identified by ES-MS and pooled.

Step 6: Acm-removal #2 The pooled solution of SEP-0:Acm+SEP-0:2+SEP-0:3+SEP-0:4+Et-Pico was diluted 3× with HPLC grade water, and solid urea was added for a final concentration of 2 molar. A threefold molar excess (relative to the total expected cysteine concentration) of a 30 mg/ml Hg(acetate)$_2$ solution in 3% aqueous acetic acid was added and the solution stirred for one hour. The solution was then made 20% in β-mercaptoethanol, loaded onto a semi-preparative reverse-phase HPLC column and purified with a step gradient. Fractions containing the desired product SEP-0:2+SEP-0:3+SEP-0:4+Et-Pico were identified by ES-MS, diluted 2× (v/v) with water containing 2× (w/w relative to peptide mass) DPC (dodecylphosphocholine) and lyophilized overnight.

Step 7: Ligation #3 Equal amounts of SEP-0:2+SEP-0:3+SEP-0:4+Et-Pico and SEP-0:1 were jointly dissolved in neat TFE at 15 mM concentration and 250 mM Phosphate buffer (pH 7.5) containing 6 M guanidinium chloride is added. To the solution 1% thiophenol was added. After one day of ligation, the ligation mix was added to a solution of 10 ml TFE, 10 ml β-mercaptoethanol, 10 ml piperidine and 20 ml 6M guanidinium chloride, pH 4, and incubated for 20 minutes to remove any remaining protecting groups. The solution was acidified with a solution of 15 mg/ml TCEP in 20% aqueous acetic acid, loaded onto a preparative reverse-phase HPLC column and purified with a linear gradient. Fractions containing the desired ligated product SEP-0 (1–166): (SEQ ID NO:1) were identified by electrospray mass spectrometry, diluted 2× (v/v) with water containing 2× (w/w relative to peptide mass) dodecylsarcosine and lyophilized.

Step 8 Folding: Full-length ligated peptide SEP-0 (1–166) was dissolved in 200 mM Tris buffer (pH 8.7) containing 6 M guanidinium chloride and 20% TFE and a ten-fold molar excess (relative to Cys residues in protein) of cysteine. This solution was dialyzed overnight against a solution of 200 mM Tris buffer (pH 8.7) containing 3 M guanidinium chloride at room temperature. The solution was then dialyzed against a solution of 200 mM Tris buffer (pH 8.7) containing 1 M guanidinium chloride at room temperature for 4 hours at 4° C. and finally against 10 mM phosphate buffer (pH 7.0) for 4 hours at 4° C. to yield the final folded product. Folding was verified by electrospray ES-MS and CD (circular dichroism) spectrometry.

Step 9 Purification: The folded polypeptide was concentrated 5× in centricon concentrator vials and loaded on to Resource S cation exchange column equilibrated at 10 mM phosphate, pH 7.0. The folded protein was eluted in a linear salt gradient to 500 mM NaCl in 10 minutes. Fractions containing the desired folded product SEP-0 (1–166) were identified by SDS-polyacrylamide gel electrophoresis (SDS-PAGE), and frozen and stored at −80° C. An analytical reverse-phase HPLC chromatogram and an ES-MS spectrum of the folded protein product as well as a CD spectrum demonstrated the presence of folded protein.

EXAMPLE 2

Synthesis of Synthetic Erythropoiesis Stimulating Protein SEP-1-L30

A second synthetic erythropoiesis stimulating protein (designated SEP-1-L30) was synthesized to contain oxime-forming groups at positions 24 and 126 of SEP-0. These groups were then used to form SEP-1-L30, in which linear (EDA-Succ-)$_{18}$ carboxylate (EDA=(4,7,10)-trioxatridecane-1,13diamine, also called TTD; Succ=—CO—CH$_2$CH$_2$CO—) polymers have been joined to the protein backbone. The sequence of the full-length SEP-1 (1–166) is:

```
                                             (SEQ ID NO:2)
APPRLICDSR VLERYLLEAK EAEK^ox ITTGCA EHCSLNEKIT

VPDTKVNFYA WKRMEVGQQA VEVWQGLALL SEAVLRGQAL

LVKSSQPWψP LQLHVDKAVS GLRSLTTLLR ALGAQKψAIS

PPDAAK^ox AAPL RTITADTFRK LFRVYSNFLR GKLKLYTGEA

CRTGDR
``` where Ψ denotes an non-native amino acid residue consisting of a cysteine that is carboxymethylated at the sulfhydryl group, and where $K^{ox}$ denotes a non-native lysine that is chemically modified at the ε-amino group with an oxime linker group coupled to a designated water-soluble polymer through an oxime bond.

A. Oximation of GRFN1776 and GRFN1711 with GRFNP32

Oxime formation was performed to attach water-soluble polymers bearing an aminooxyacetyl group to peptides carrying a ketone carbonyl group. To accomplish this, the following peptide segments were synthesized:

```
Segment SEP-1:4 (GRFN 1776; composed of residues 117–166 of SEQ ID NO:2):
CAISPPDAAK AAPLRTITAD TFRKLFRVYS NFLRGKLKLY TGEACRTGDR-carboxylate
(where Lys^126 is modified with a levulinic acid residue at the
ε-amino group, and where Cys^117 is Acm protected)

Segment SEP-1:1 (GRFN 1711, composed of residues 1–32 of SEQ ID NO:2):
APPRLICDSR VLERYLLEAK EAEKITTGCA EH-thioester
(where Lys24 is modified with a levulinic acid residue)
```

Segment SEP-1:1 (GRFN 1711) was synthesized on a thioester-generating resin, and Segment SEP-1:4 (GRFN 1776) on a —OCH$_2$-Pam-resin as in Example 1. Lysines 24 and 126 of these two peptide segments were initially protected with an Fmoc group at the ε-amino group. After completion of the chain assembly, the Fmoc-bearing amino groups were deprotected following standard Fmoc deprotection procedures and modified by attachment of levulinic acid to each peptide resin, respectively. The peptides were then deprotected and simultaneously cleaved from the resin support as described in Example 1. The peptides were purified by preparative C4 reverse phase HPLC. Fractions containing pure peptide were identified using ES-MS, pooled and lyophilized for subsequent ligation. GRFNP32 [-(EDA-Succ)$_{18}$ carboxylate] was assembled on a Sasrin carboxyl-generating resin following standard protocols (Rose, K. et al., U.S. Pat. No. 6,552,167; Rose, et al., J Am Chem Soc.(1999) 121: 7034). An aminooxyacetyl (AoA) moiety was attached to the N-terminal amino group of the polymer by coupling a fivefold excess of activated Boc-aminooxyacetic acid. The polymer chain was cleaved from the resin support using classic Fmoc-chemistry procedures. The polymer chain was purified by preparative C4 reverse-phase HPLC. Fractions containing pure polymer were identified using ES-MS, pooled and lyophilized for subsequent ligation.

Segment SEP-1:4 and GRFNP32 were jointly dissolved at an equimolar ratio in 50% aqueous acetonitrile containing 0.1% TFA . The solution was then lyophilized. The dried powder was dissolved and the polymer-modified peptide separated from unmodified peptide and unreacted polymer by preparative gradient C4 reverse-phase HPLC. Fractions containing the desired oximated product SEP-1:4+GP32 were identified by ES-MS and pooled and lyophilized.

Segment SEP-1:1 and GRFNP32 were jointly dissolved at an equimolar ratio in 50% aqueous acetonitrile containing 0.1% TFA. The solution was then lyophilized. The dried powder was dissolved and the polymer-modified peptide separated from unreacted polymer by preparative gradient C4 reverse-phase HPLC. Fractions containing the desired oximated product SEP-1:1+GP32 were identified by ES-MS and pooled and lyophilized.

B. Synthesis of Synthetic Erythropoiesis Stimulating Protein SEP-1-L30

```
                                              (SEQ ID NO:2)
APPRLICDSR VLERYLLEAK EAEK^oxITTGCA EHCSLNEKIT

VPDTKVNFYA WKRMEVGQQA VEVWQGLALL SEAVLRGQAL

LVKSSQPWψP LQLHVDKAVS GLRSLTTLLR ALGAQKψAIS

PPDAAK^oxAAPL RTITADTFRK LFRVYSNFLR GKLKLYTGEA

CRTGDR
``` where Ψ denotes an non-native amino acid residue consisting of a cysteine that is carboxymethylated at the sulfhydryl

```
SEP-1-L30 was synthesized in solution from four polypeptide segments:

Segment SEP-1:1 + GP32 (GRFN 1711 + GRFNP32, corresponding to residues 1-32 of SEQ ID NO:2):
APPRLICDSR VLERYLLEAK EAEK^oxITTGCA EH-thioester
(where Lys^24 is modified at the ε-amino group with a levulinic oxime linker group that is
coupled to GRFNP32 through a levulinic-aminooxyacetyl (Lev-AoA) oxime bond denoted K^ox)

Segment SEP-1:2 (GREN 1712, corresponding to residues 33-88 of SEQ ID NO:2):
CSLNEKTT VPDTKVNFYA WKRMEVGQQA VEVWQGLALL SEAVLRGQAL LVKSSQPW-thioester
(where Cys^33 is Acm protected)

Segment SEP-1:3 (GRFN 1713, corresponding to residues 89-116 of SEQ ID NO:2):
CP LQLHVDKAVS GLRSLTTLLR ALGAQK-thioester
(where Cys^89 is Acm protected)

Segment SEP:1:4 + GP32 (GRFN 1776 + GRFNP32, corresponding to residues 117-166 of SEQ ID NO:2):
CAIS PPDAAK^oxAAPL RTITADTFRK LFRVYSNFLR GKLKLYTGEA CRTGDR-carboxylate
(where Lys^126 is modified at the ε-amino group with a levulinic oxime linker group that is
coupled to GRFNP32 through a levulinic-aminooxycetyl (Lev-AoA) oxime bond denoted K^ox, and
where the C-terminal cysteine carries a picolyl (pico) protecting group)
```

Synthesis of additional peptides, ligation reactions, carboxymethylation, protecting group removal reactions, folding and purification were performed as described in Example 1 to yield full-length, folded SEP-1-L30. An analytical reverse-phase HPLC chromatogram and an ES-MS spectrum of the folded protein product as well as a CD spectrum demonstrated the presence of folded protein

EXAMPLE 3

Synthesis of Synthetic Erythropoiesis Stimulating Protein SEP-1-L26

A third synthetic erythropoiesis stimulating protein (designated SEP-1-L26) was synthesized to contain oxime-forming groups at positions 24 and 126 of SEP-0. These groups were then used to form SEP-1-L26, in which the linear polymers (EDA-Succ)$_{18}$ carboxylate and (EDA-Succ)$_6$-amide have been joined to the protein backbone through oxime linkages at positions 24 and 126, respectively. The sequence of the full-length SEP-1 (1-166) is:

group, and where K$^{ox}$ denotes a non-native lysine that is chemically modified at the ε-amino group with an oxime linker group coupled to a designated water-soluble polymer through an oxime bond.

In contrast to SEP-1-L30, the SEP-1-L26 construct was designed to bear a smaller and uncharged water-soluble polymer attached at position 126. The polymer attached at position 24 was the same as in SEP-1-L30. Assembly of the full-length product was as described in Example 2.

A. Oximation of GRFN1776 with GRFANP6 and Oximation of GRFN1711 with GRFNP32

Oxime formation was performed to attach water-soluble polymers bearing an aminooxyacetyl group to peptides carrying a ketone carbonyl group. To accomplish this, the following peptide segments were synthesized:

```
Segment SEP-1:4 (GRFN 1776; composed of residues 117-166 of SEQ ID NO:2):
CAISPPDAAK AAPLRTITAD TFRKLFRVYS NFLRGKLKLY TGEACRTGDR-carboxylate
(where Lys^126 is modified with a levulinic acid residue at the ε-amino
group, and where Cys^117 is Acm protected)

Segment SEP-1:1 (GRFN 1711, composed of residues 1-32 of SEQ ID NO:2):
APPRLICDSR VLERYLLEAK EAEKITTGCA EH-thioester
(where Lys^24 is modified with a levulinic acid residue)
```

Segment SEP-1:1 (GRFN 1711) was synthesized on a thioester-generating resin, and Segment SEP-1:4 (GRFN 1776) on a —OCH$_2$-Pam-resin as in Example 1. Lysines 24 and 126 of these two peptide segments were initially protected with an Fmoc group at the ε-amino group. After completion of the chain assembly, the Fmoc-bearing amino groups were deprotected following standard Fmoc deprotection procedures and modified by attachment of levulinic acid to each peptide resin, respectively, following standard coupling protocols. The peptides were then deprotected and simultaneously cleaved from the resin support according to standard Boc-chemistry procedures as in Example 1. The peptides were separately purified by preparative C4 reverse-phase HPLC. For each peptide, fractions containing pure peptide were identified using ES-MS, pooled and lyophilized for subsequent ligation.

The water soluble polymer (EDA-Succ)$_{18}$ carboxylate (GRFNP32) was assembled on a Sasrin carboxy-generating resin following standard protocols (Rose, K. et al., U.S. patent application Ser. No. 09/379,297; Rose, et al., *J Am Chem Soc.*(1 999) 121: 7034). The water soluble polymer (EDA-Succ)$_6$-amide (GRFNP6) was assembled on a Sieber amide-generating resin following standard protocols (Rose, K. et al., U.S. Pat. No. 6,552,167; Rose, et al., *J Am Chem Soc.* (1999) 121: 7034). An aminooxyacetyl (AoA) moiety was attached to the N-terminal amino group of each resin-bound polymer by coupling a fivefold excess of activated Boc-aminooxyacetic acid. The two polymer chains were separately cleaved from the respective resin supports using classic Fmoc—chemistry procedures. Each polymer chain was purified by preparative reverse phase HPLC. For each polymer, fractions containing pure polymer were identified using ES-MS, pooled and lyophilized for subsequent ligation.

Segment SEP-1:4 and GRFNP6 were jointly dissolved at an equimolar ratio in 50% aqueous acetonitrile containing 0.1% TFA. The solution was then lyophilized. The dried powder was dissolved and the polymer-modified peptide separated from unmodified peptide and unreacted polymer by preparative gradient C4 reverse-phase HPLC. Fractions containing the desired oximated product SEP-1:4+GP6 were identified by ES-MS and pooled and lyophilized.

Segment SEP-1:1 and GRFNP32 were jointly dissolved at an equimolar ratio in 50% aqueous acetonitrile containing 0.1% TFA. The solution was then lyophilized. The dried powder was dissolved and the polymer-modified peptide separated from unreacted polymer by preparative gradient C4 reverse-phase HPLC. Fractions containing the desired oximated product SEP-1:1+GP32 were identified by ES-MS and pooled and lyophilized.

B. Synthesis of Synthetic Erythropoiesis Stimulating Protein SEP-1-L26

Synthesis of additional peptides, ligation reactions, carboxymethylation, protecting group removal reactions, folding and purification were performed as described in Examples 1 and 2 to yield full-length, folded SEP-1-L26. An analytical C4 reverse-phase HPLC chromatogram and an ES-MS spectrum of the folded protein product as well as a CD spectrum demonstrated the presence of folded protein.

EXAMPLE 4

Synthesis of Synthetic Erythropoiesis Stimulating Protein SEP-1-B50

A fourth synthetic erythropoiesis stimulating protein (designated SEP-1-B50) was synthesized. The amino acid sequence of the full-length SEP-1-B50 is the same as that of SEP-1-L30:

(SEQ ID NO:2)
APPRLICDSR VLERYLLEAK EAEK$^{ox}$ITTGCA EHCSLNEKIT

VPDTKVNFYA WKRMEVGQQA VEVWQGLALL SEAVLRGQAL

LVKSSQPWψP LQLHVDKAVS GLRSLTTLLR ALGAQKψAIS

PPDAAK$^{ox}$AAPL RTITADTFRK LFRVYSNFLR GKLKLYTGEA

CRTGDR where Ψ denotes an non-native amino acid residue consisting of a cysteine that is carboxymethylated at the sulfhydryl group, and where K$^{ox}$ denotes a non-native lysine that is chemically modified at the ε-amino group with an oxime linker group coupled to a designated water-soluble polymer through an oxime bond.

However, the protein was derivatized with a branched polymer construct having four linear (Succ-EDA)$_{12}$ moieties rather than the linear (Succ-EDA)$_{18}$ polymer of SEP-1-L30. Derivatization was accomplished via oxime linkages. Assembly of the full-length product was as described in Example 2.

A. Synthesis of Template GR-FNP17 Carrying Multiple Thiol Groups

The template GRFNP17 was synthesized manually on an amide generating (4-methyl)benzhydrylamine(MBHA)-resin on a 0.4 mmol scale. Fmoc-Lys(Boc)-OH was coupled using standard coupling protocols (Schnölzer, M., *Int J Pept Protein Res.* (1992) 40:180–93). 2.1 mmol amino acid, 10%

```
SEP-1-L26 was synthesized in solution from four polypeptide segments:

Segment SEP:1:1 + GP32 (GRFN 1711 + GRFNP32, corresponding to residues 1–32 of SEQ ID NO:2):
APPRLICDSR VLERYLLEAK EAEK$^{ox}$ITTGCA EH-thioester
(where Lys$^{24}$ is modified at the ε-amino group with a levulinic oxime linker group that is
coupled to GRFNP32 through a levulinic-aminooxyacetyl (Lev-AoA) oxime bond denoted K$^{ox}$)

Segment SEP-1:2 (GRFN 1712, corresponding to residues 33–88 of SEQ ID NO:2):
CSLNEKIT VPDTKVNFYA WKRMEVGQQA VEVWQGLALL SEAVLRGQAL LVKSSQPW-thioester
(where Cys$^{33}$ is Acm protected)

Segment SEP-1:3 (GRFN 1713, corresponding to residues 89–116 of SEQ ID NO:2):
CP LQLHVDKAVS GLRSLTTLLR ALGAQK-thioester
(where Cys$^{89}$ is Acm protected)

Segment SEP:1:4 + GP6 (GREN 1776 + GRFNP6, corresponding to residues 117–166 of SEQ ID NO:2):
CAIS PPDAAK$^{ox}$AAPL RTITADTFRK LFRVYSNFLR GKLKLYTGEA CRTGDR-carboxylate
(where Lys$^{126}$ is modified at the ε-amino group with a levulinic oxime linker group that
is coupled to GRFNP6 through a levulinic-aminooxyacetyl (Lev-AoA) oxime bond denoted K$^{ox}$,
and where the C-terminal cysteine [i.e. Cys$^{161}$] carries a picolyl (pico) protecting group)
```

DREA in 3.8 ml 0.5M HBTU was used; i.e. 5-fold excess of amino acid. After removal of the Fmoc protecting group, Fmoc-Lys(Fmoc)-OH was coupled using standard amino acid coupling protocols (2.1 mmol amino acid, 10% DEA in 3.8 ml 0.5M HBTU; i.e. 5-fold excess amino acid). After a second Fmoc removal step, Fmoc-Lys(Fmoc)-OH was coupled using standard amino acid coupling protocols (4.2 mmol amino acid, 10% DIEA in 7.6 ml 0.5M HBTU; i.e. 5-fold excess amino acid relative to free amine). After a final Fmoc deprotection step, a five-fold excess (relative to free amines) of S-acetyl thioglycolic acid pentafluorophenyl ester (SAMA-oPfp) in DMF was coupled for 30 minutes. The Boc protecting group of the side chain of the C-terminal lysyl residue was removed by two times one minute batch washes with neat TFA, followed by neutralization of the resin by washing with 10% DIEA in DMF. 2 mmol Boc-aminooxyacetic acid and 2 mmol N-hydroxysuccinimide (NHS) were dissolved in 3 ml DMF. After addition of 2 mmol DIC (diisopropylcarbodiimide), the acid was activated for 30–60 minutes. The solution was added to the neutralized resin and coupled 1 hr. Finally, the S-linked acetyl groups were removed with 20% piperidine in DMF for 30 minutes. The template was deprotected and simultaneously cleaved from the resin support using HF/p-cresol according to standard Boc-chemistry procedures in the presence of cysteine as a scavenger for free aldehyde (Schnölzer, M., *Int J Pept Protein Res*. (1992) 40:180–93). The recovered polyamide in 50% B [i.e. 50% aqueous acetonitrile containing 0.1% TFA] (aldehyde free) was frozen and lyophilized. For purification, the template crude product was dissolved in 2 ml 50% B, and 100 ml 100% A [i.e. 0.1% TFA in water] was added to dilute the sample (Avoid guanidinium chloride or acetate addition, since the addition of aldehyde is guaranteed). The template was loaded onto a C4 preparative reverse-phase HPLC column equilibrated at T=40° C. at 3% B. Salts were eluted isocratically and the desired template, GRFNP17 purified in a linear gradient. Fractions containing the desired product were identified by ES-MS, pooled and lyophilized.

B. Synthesis of Branched Water-Soluble Polymer GRNP29

GRFNP29, a branched (EDA-Succ)$_2$ polymer of 15 kDa molecular weight was synthesized by thioether-generating ligation of purified thiol-containing template GRFNP17 and a linear polymer GRFNP31, Br-acetyl-(EDA-Succ)$_{12}$ carboxylate, where GRFNP31 was synthesized on a Sasrin carboxy-generating resin following standard protocols (Rose, K. et al., U.S. Pat. No. 6,552,167; Rose, et al., *J Am Chem Soc*.(1999) 121: 7034).

A 1.3× molar excess (over total thiols) of the purified GRFNP31, Br-acetylated (EDA-Succ)$_{12}$, and purified thiol-containing template GRFNP17 were jointly dissolved 0.1 M Tris-HCl/6 M guanidinium chloride, pH 8.7 at ~10 mM concentration. After dissolution, the solution was diluted threefold (v/v) with 0.1 M Tris-HCl, pH 8.7 buffer. The ligation mixture was stirred at room temperature and the reaction monitored by reversed-phase HPLC and ES/MS. Additional GRFNP31 reactant was added on an as-needed basis until the desired reaction product was the major product. For workup, 3× (v/v to ligation mix) 0.1M acetate/6 M guanidinium chloride, pH 4 was added, and the solution was loaded onto a preparative C4 reverse-phase HPLC column, and purified with a linear gradient. Fractions containing pure GRFNP29 construct were identified using ES-MS, pooled and lyophilized.

C. Oximation of GRFN1776 and GRFN1711 with GRFNP29

Segments SEP-1:4, and Segment SEP-1:1 were synthesized as described in Example 2. Segment SEP-1:4 and GRFNP29 were jointly dissolved at an equimolar ratio in 50% aqueous acetonitrile containing 0.1% TFA . The solution was lyophilized. The dried powder was loaded onto a preparative reverse-phase HPLC column (1 inch diameter). The polymer-modified peptide was separated from unmodified peptide and unreacted polymer by preparative gradient C4 reverse-phase HPLC. Fractions containing the desired oximated product SEP:1:4+GP29 were identified by ES-MS and pooled.

Segment SEP-1:1 and GRFNP29 were jointly dissolved at an equimolar ratio in 50% aqueous acetonitrile containing 0.1% TFA. The solution was frozen and lyophilized. The dried powder was dissolved in 50% aqueous acetonitrile containing 0.1% TFA and loaded onto a preparative GPC (gel permeation chromatography) column (1 inch diameter). The polymer-modified peptide was separated from unmodified peptide and unreacted polymer by isocratic elution. Fractions containing the desired oximated product SEP-1:1+GP29 were identified by ES-MS and pooled.

D. Synthesis Of Synthetic Erythropoiesis Stimulating Protein SEP-1-B50

```
SEP-1-B50 (SEQ ID NO:2) was synthesized in solution from four polypeptide segments:

Segment SEP-1:1 + GP29 (GRFN 1711 + GRFNP29, corresponding to residues 1-32 of SEQ ID NO:2):
APPRLICDSR VLERYLLEAK EAEK^OX ITTGCA EH-thioester
(where Lys^24 is modified at the ε-amino group with a levulinic oxime linker group that is
coupled to GRFNP29 through a levulinic-aminooxyacetyl (Lev-AoA) oxime bond denoted K^ox)

Segment SEP-1:2 (GRFN 1712, corresponding to residues 33-88 of SEQ ID NO:2):
CSLNEKIT VPDTKVNFYA WKRMEVGQQA VEVWQGLALL SEAVLRGQAL LVKSSQPW-thioester
(where Cys^33 is Acm protected)

Segment SEP-1:3 (GRFN 1713, corresponding to residues 89-116 of SEQ ID NO:2):
CP LQLHVDKAVS GLRSLTTLLR ALGAQK-thioester
(where Cys^89 is Acm protected)

Segment SEP11:4 + GP29 (GRFN 1776 + GRFNP29, corresponding to residues 117-166 of SEQ ID NO:2):
CAIS PPDAAK^OX AAPL RTITADTFRK LFRVYSNFLR GKLKLYTGEA CRTGDR-carboxylate
(where Lys^126 is modified at the ε-amino group with a levulinic oxime linker group that is
coupled to GRFNP29 through a levulinic-aminooxyacetyl (Lev-AoA) oxime bond denoted K^ox, and
where the C-terminal cysteine carries a picolyl (pico) protecting group)
```

Synthesis of additional peptides, ligation reactions, carboxymethylation, protecting group removal reactions, folding and purification were performed as described in Examples 1 and 2, except that purification was on a Resource Q column, to yield full-length, folded SEP-1-B50 (SEQ ID NO: 2). An analytical C4 reverse-phase HPLC chromatogram and an ES-MS spectrum of the folded protein product SEP-1-B50 as well as a CD spectrum demonstrated the presence of folded protein.

EXAMPLE 5

Synthesis of Synthetic Erythropoiesis Stimulating Protein SEP-3-L42

A fifth synthetic erythropoiesis stimulating protein (designated SEP-3-L42) was synthesized. The amino acid sequence of the full-length SEP-3 protein is:

```
                                        (SEQ ID NO:3)
APPRLICDSR VLERYLLEAK EAECITTGCA EHCSLNECIT

VPDTKVNFYA WKRMEVGQQA VEVWQGLALL SEAVLRGQAL

LACSSQPWEP LQLHVDKAVS GLRSLTTLLR ALGAQKEAIS

PPDAACAAPL RTITADTFRK LFRVYSNFLR GRLKLYTGEA

CRTGDR
```

The cysteine residues in positions: 24, 38, 83, and 126 were modified with maleimide-functionalized (EDA-Succ)$_{18}$ (GRFNP32) polymer units (via a Michael addition reaction) to form SEP-3-L42.

mM phosphate containing 25% β-mercaptoethanol} and incubated for 20 minutes. The solution was acidified with a solution of 15 mg/ml TCEP in glacial acetic acid, loaded onto a preparative C4 reverse-phase HPLC column and purified with a linear gradient. Fractions containing the desired ligated product SEP-3:Acm+SEP-3:3+SEP-3:4 were identified by ES-MS and pooled.

Step 2:Acm-removal #1 For Acm removal, the aqueous acetonitrile solution containing the pooled fractions of SEP-3:Acm+SEP-3:3+SEP-3:4 was diluted 1× with HPLC grade water, and solid urea was added for a final concentration of 2 molar. A threefold molar excess (relative to the total expected cysteine concentration) of a 30 mg/ml Hg(acetate)$_2$ solution in 3% aqueous acetic acid was added and the solution was stirred for one hour. The solution was then made 20% in β-mercaptoethanol, loaded onto a semi-preparative C4 reverse-phase HPLC column and purified with a step gradient. Fractions containing the desired ligated product SEP-3:3+SEP-3:4 were identified by ES-MS and lyophilized overnight.

Step 3: Ligation #2 Equal amounts of SEP-3:3+SEP-3:4 and SEP-3.2 were jointly dissolved in neat TFE trifluoroethanol at 15 mM concentration. 250 mM Phosphate buffer (pH 7.5) containing 6 M guanidinium and 1% thiophenol was added, resulting in a clear solution of the peptide segments. After one day of ligation, the ligation mix (defined as 1 volume) was added to 2 volumes of a solution of 10 ml

```
In detail, SEP-3 was synthesized in solution from four polypeptide segments:

Segment SEP-3:1 (GRFN 1747, corresponding to residues 1-37 of SEQ ID NO:3):
APPRLICDSR VLERYLLEAK EAECITTGCA EHCSLNE-thioester
(where Cys⁷, Cys²⁹, and Cys³³ are Acm protected)

Segment SEP-3:2 (GRFN 1774, corresponding to residues 38-82 of SEQ ID NO:3):
CIT VPDTKVNFYA WKRMEVGQQA VEVWQGLALL SEAVLRGQAL LA-thioester
(where Cys³⁸ is side chain protected with the Acm group)

Segment SEP-3:3 (GRFN 1749, corresponding to residues 83-125 of SEQ ID NO:3):
CSSQPWEP LQLHVDKAVS GLRSLTTLLR ALGAQKEAIS PPDAA-thioester
(where Cys⁸³ is side chain protected with the Acm group)

Segment SEP-3:4 (GRFN 1750, corresponding to residues 126-166 of SEQ ID NO:3):
CAAPL RTITADTFRK LFRVYSNFLR GKLKLYTGEA CRTGDR-carboxylate
(where Cys¹⁶¹ is Pbo [i.e., 4-(CH₃S(O)-)benzyl-] protected)
```

Peptide synthesis. The peptides SEP-3:1 and SEP-3:2 and SEP-3:3 were synthesized on a thioester-generating resin by the in situ neutralization protocol for Boc chemistry SPPS, using established side-chain protection strategies as described in Example 1, with changes in protecting group strategy as noted in the specific peptides above. Segment SEP-3:4 was synthesized analogously on a —OCH$_2$-Pam-resin. The peptides were deprotected and simultaneously cleaved from the resin support as described in Example 1. The resulting peptides described above were purified by preparative RP-HPLC. Fractions containing pure peptide were identified using ES-MS, pooled and lyophilized for subsequent ligation.

Step 1: Ligation #1. Segment SEP-3:4 and segment SEP-3:3 were dissolved in TFE at 15 mM concentration. Saturated phosphate buffer (pH 7.5) containing 6 M guanidinium chloride and 1% thiophenol was added, resulting in a clear solution of the peptide segments. After ligation, the ligation mix (defined as 1 volume) was added to 2 volumes of a solution of {2 ml TFE, 6 ml 6 M guanidinium chloride, 100

TFE, 10 ml β-mercaptoethanol, 10 ml piperidine and 20 ml 6M guanidinium, pH 4, and incubated for 20 minutes to remove any remaining protecting groups. The solution was acidified with a solution of 15 mg/ml TCEP in 20% aqueous acetic acid, loaded onto a preparative C4 reverse-phase HPLC column and purified with a linear gradient. Fractions containing the desired ligated product SEP-3:Acm+SEP-3:2+SEP-3:3+SEP-3:4 were identified by ES-MS and lyophilized overnight.

Step 4 Acm removal For Acm removal, the aqueous acetonitrile solution containing the pooled fractions of SEP-3:Acm+SEP-3:2+SEP-3:3+SEP-3:4 was diluted 1× with HPLC grade water, and solid urea added for a final concentration of 2 molar. A threefold molar excess (relative to the total expected cysteine concentration) of a 30 mg/ml Hg(acetate)$_2$ solution in 3% aqueous acetic acid was added and the solution stirred for one hour. The solution was then made 20% in β-mercaptoethanol, loaded onto a C4 semi-preparative reverse-phase HPLC column and purified with a step gradient. Fractions containing the desired ligated product SEP-3:2+SEP-3:3+SEP-3:4 were identified by ES-MS and lyophilized overnight.

Step 5: Ligation #3 Equal amounts of SEP-3:2+SEP-3:3+SEP-3:4 and SEP:3:1 were jointly dissolved in neat TFE at 15 mM concentration. 250 mM Phosphate buffer (pH 7.5) containing 6 M guanidinium and 1% thiophenol was added, resulting in a clear solution of the peptide segments. After one day of ligation, the ligation mix (defined as 1 volume) was added to 2 volumes of a solution of 10 ml TFE, 10 ml β-mercaptoethanol, 10 ml piperidine and 20 ml 6M guanidinium, pH 4, and incubated for 20 minutes to remove any remaining protecting groups. The solution was acidified with a solution of 15 mg/ml TCEP in 20% aqueous acetic acid, loaded onto a preparative C4 reverse-phase HPLC column and purified with a linear gradient. Fractions containing the desired ligated product SEP-3:1+SEP-3:2+SEP-3:3+SEP-3:4 were identified by ES-MS and lyophilized overnight.

Step 6: Attachment of the Polymer GRFNP32. A maleimide-functionalized linear (EDA-Succ)$_{18}$ polymer called GRFNP32-maleimide was prepared by functionalizing GRFNP32 with BMPS (3-maleimide propionic acid NHS ester, Pierce, USA) following the manufacturers protocols to form a maleimide-functionalized (EDA-Succ)$_{18}$ polymer [i.e., maleimide-(EDA-Succ)$_{18}$]. SEP-3:1+SEP-3:2+SEP-3:3+SEP-3:4 was dissolved in the minimum amount of TFE required. A threefold excess of GRFNP32-maleimide was dissolved in 6M guanidinium chloride, 100 mM phosphate, pH 7.5 and added to the TFE solution. The progress of the Michael addition reaction was followed by analytical reverse-phase HPLC. After the reaction was complete, the solution was loaded onto a preparative C4 reverse-phase HPLC column and purified with a linear gradient. Fractions containing the desired polymer-modified product SEP3:Acm+SEP-3:1+SEP-3:2+SEP-3:3+SEP-3:4+pPEG [i.e. the ligated full-length 166 residue polypeptide chain with four copies of GRFNP32 attached to the side chain thiols of Cys$^{24}$, Cys$^{38}$, Cys$^{83}$ and Cys$^{126}$, and thus also called SEP3:Acm+SEP-3:1+SEP-3:2+SEP-3:3+SEP-3:4+GP32], were identified by ES-MS and lyophilized overnight.

Step 7: Pbo removal For Pbo reduction, the lyophilized powder of SEP3:Acm+SEP-3:1+SEP-3:2+SEP-3:3+SEP-3:4+GP32 was dissolved in neat TFA containing 5% ethanedithiol. The Pbo group was then cleaved by addition of 10% thioanisole and 15% bromotrimethylsilane for 30 minutes. The solution was dried in a rotator-evaporator and taken up in aqueous acetonitrile containing 0.1% TFA. The resulting solution was loaded onto a semi-preparative reverse-phase HPLC column and purified with a step gradient. Fractions containing the desired Cys$^{161}$-deprotected product SEP3:Acm+SEP-3:1+SEP-3:2+SEP-3:3+SEP-3:4+GP32-Pbo were identified by ES-MS and lyophilized overnight.

Step 8: Acm removal For final Acm removal from the side chains of Cys$^7$, Cys$^{29}$, and Cys$^{33}$, the aqueous acetonitrile solution containing the pooled fractions of SEP3:Acm+SEP-3:1+SEP-3:2+SEP-3:3+SEP-3:4+GP32-Pbo was diluted 1× with HPLC grade water, and solid urea was added for a final concentration of 2 molar. A threefold molar excess (relative to the total expected cysteine concentration) of a 30 mg/ml Hg(acetate)$_2$ solution in 3% aqueous acetic acid was added and the solution was stirred for one hour. The solution was then made 20% in β-mercaptoethanol, loaded onto a semi-preparative C4 reverse-phase HPLC column and purified with a step gradient. Fractions containing the desired ligated, polymer-modified product SEP-3 (1–166) were identified by ES-MS and lyophilized overnight.

Step 9 Folding: Full-length ligated, polymer-modified peptide SEP-3 (1–166) was dissolved in 200 mM Tris buffer (pH 8.7) containing 6 M guanidinium chloride and 20% TFE and a ten-fold molar excess (relative to Cys residues in SEP-3) of cysteine. This solution was dialyzed overnight against a solution of 200 mM Tris buffer (pH 8.7) containing 3 M guanidinium chloride at room temperature. The solution was then dialyzed against a solution of 200 mM Tris buffer (pH 8.7) containing 1 M guanidinium chloride for 4 hours at 4° C. and finally against 10 mM phosphate buffer (pH 7.0) for 4 hours at 4° C. to yield the final folded product. Folding was verified by electrospray ES-MS and CD spectrometry.

Step 10 Purification: The folded polypeptide was concentrated 5× in centricon concentrator vials and loaded on to Resource S cation exchange column equilibrated at 10 mM phosphate, pH 7.0. The folded protein was eluted in a linear salt gradient to 500 mM NaCl in 10 minutes. Fractions containing the desired folded product SEP-3-L42 were identified by SDS-PAGE, and frozen and stored at –80 ° C.

EXAMPLE 6

Bioactivity Assay of Synthetic Erythropoiesis Stimulating Proteins

The bioactivity of folded synthetic erythropoiesis stimulating proteins, SEP-0, SEP-1-L26, SEP-1-L30, SEP-1-B50, and SEP-3-L42 was determined using UT/7 and 32D 103197 cell lines, in factor-dependent cell-line proliferation assays using commercial recombinant erythropoietin as a control standard. UT-7 is a human megakaryoblastic leukemia cell line with absolute dependence on one of interleukin-3, granulocyte-macrophage colony-stimulating factor (GM-CSF), or erythropoietin (EPO) for growth and survival (Miura Y, et al., Acta Haematol (1998) 99:180–184); Komatsu N, et al., Cancer Res. (1991) 51:341–8). 32D 103197 is a murine hemopoietic cell line (Metcalf, D. Int J Cell Cloning (1992) 10:116–25).

Stock-solutions of the SEP constructs were made in Iscove's modified Dulbecco's medium (IMDM), 10% FBS (Fetal bovine serum), glutamine and Penstrep, and serial 2× dilutions of these stock solutions were added to multi-well plates to which human UT/7 EPO cells at a concentration of 5000 cells/50 µl were added. The plates were incubated at 37° C. in the presence of 5% $CO_2$ and monitored daily for growth. After four days, 20 µl 2.5 mg/ml MTT (methylthiazol tetrazolium) in PBS (phosphate buffered saline) was added and the plates were incubated for four hours. 150 µl IPA was added and the absorbance of each well was read at 562 nm. The ED50 (effective dose to reach 50% of maximum effect) values for the SEP compounds was determined and compared to that of CHO (Chinese hamster ovary)—cell produced rhEPO (recombinant human erythropoietin). The results from these experiments demonstrated that all of the synthetic erythropoiesis stimulating proteins exhibited bioactivity. ED50 results for SEP-0, SEP-1-L26, SEP-1-L30, and SEP-1-B50 are shown in Table VI.

TABLE VI

| Erythropoiesis Stimulating Protein | In Vitro ED50 Values (pM) | |
|---|---|---|
| | UT-7 (Human) Cells | 32D 103197 (Mouse) Cells |
| SEP-0 | 1,570 | 863 |
| SEP-1-L26 | 46.5 | 100.8 |
| SEP-1-L30 | 71.5 | 182.5 |
| SEP-1-B50 | 182 | 6200 |
| rh EPO | 32.5 | 136.3 |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for synthesizing a desired polypeptide of formula:

$$aa_{NH_2}\text{-}Q\text{-}aa_x\text{-}aa_y\text{-}W\text{-}aa_{COOH}$$

wherein Q and W each denote the optional presence of one or more additional amino acid residues, $aa_{NH_2}$ denotes the N-terminal amino acid residue of the polypeptide; $aa_x$ and $aa_y$ denote internal adjacent amino acid residues, having side chains x and y, respectively, and wherein $aa_y$ is a non-ribosomally synthesized amino acid residue and $aa_{COOH}$ denotes the C-terminal amino acid residue of the polypeptide;

said method comprising:

(A) ligating a first peptide having the formula: $aa_{NH_2}$-Q-$aa_x$-COSR, wherein R is any group compatible with the thioester group, to a second peptide having the formula: Cys-W-$aa_{COOH}$ to thereby form the polypeptide: $aa_{NH_2}$-Q-$aa_x$-Cys-W-$aa_{COOH}$; and (B) incubating said polypeptide in the presence of a reagent $R_{aa}$-X, where $R_{aa}$ is a group whose structure comprises the side chain of amino acid residue $aa_y$; and X is a good leaving group; said incubation being under conditions sufficient to form said desired polypeptide.

2. The method of claim 1, wherein X is a halogen.

3. The method of claim 2, wherein said halogen is F, I or Br.

4. The method of claim 1, wherein said amino acid residue $aa_y$ is selected from the group consisting of a pseudo-arginine; a pseudo-asparagine; a pseudo-aspartate; a pseudo-dopamine; a pseudo-glutamate; a pseudo-glutamine; a pseudo-histidine; a pseudo-isoleucine; a pseudo-leucine; a pseudo-lysine; a pseudo-methionine; a pseudo-phenylalanine; a pseudo-serine; a pseudo-threonine; a pseudo-tryptophan; a pseudo-tyrosine; and a pseudo-valine.

5. The method of claim 1, wherein R is an aryl, benzyl, or alkyl group.

* * * * *

SEQUENCE LISTING

```
<160> NUMBER OF SEQ ID NOS: 3

<210> SEQ ID NO 1
<211> LENGTH: 166
<212> TYPE: PRT
<213> ORGANISM: Homo sapiens

<400> SEQUENCE: 1

Ala Pro Pro Arg Leu Ile Cys Asp Ser Arg Val Leu Glu Arg Tyr Leu
 1               5                  10                  15

Leu Glu Ala Lys Glu Ala Glu Lys Ile Thr Thr Gly Cys Ala Glu His
             20                  25                  30

Cys Ser Leu Asn Glu Lys Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Lys Ser Ser Gln Pro Trp Cys Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Cys Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 2
<211> LENGTH: 166
<212> TYPE: PRT
<213> ORGANISM: Homo sapiens

<400> SEQUENCE: 2

Ala Pro Pro Arg Leu Ile Cys Asp Ser Arg Val Leu Glu Arg Tyr Leu
 1               5                  10                  15

Leu Glu Ala Lys Glu Ala Glu Lys Ile Thr Thr Gly Cys Ala Glu His
             20                  25                  30

Cys Ser Leu Asn Glu Lys Ile Thr Val Pro Asp Thr Lys Val Asn Phe
         35                  40                  45
```

```
Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Lys Ser Ser Gln Pro Trp Cys Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Cys Ala Ile Ser Pro Pro Asp Ala Ala Lys Ala Ala
                115                 120                 125

Pro Leu Arg Thr Ile Thr Ala Asp Thr Phe Arg Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 3
<211> LENGTH: 166
<212> TYPE: PRT
<213> ORGANISM: Homo sapiens

<400> SEQUENCE: 3

Ala Pro Pro Arg Leu Ile Cys Asp Ser Arg Val Leu Glu Arg Tyr Leu
 1               5                  10                  15

Leu Glu Ala Lys Glu Ala Glu Cys Ile Thr Thr Gly Cys Ala Glu His
                 20                  25                  30

Cys Ser Leu Asn Glu Cys Ile Thr Val Pro Asp Thr Lys Val Asn Phe
             35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Ala Cys Ser Ser Gln Pro Trp Cys Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Cys Ala Ile Ser Pro Pro Asp Ala Ala Cys Ala Ala
                115                 120                 125

Pro Leu Arg Thr Ile Thr Ala Asp Thr Phe Arg Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```